(12) United States Patent
Bulsen et al.

(10) Patent No.: US 9,616,224 B2
(45) Date of Patent: Apr. 11, 2017

(54) METHOD FOR FUNCTIONAL ELECTRICAL STIMULATION THERAPY

(71) Applicant: Simple Systems Inc., Mississauga, Ontario (CA)

(72) Inventors: Abudulkadir Bulsen, Scarborough (CA); Naaz Ankur Desai, Etobicoke (CA); Milos Popovic, Mississauga (CA)

(73) Assignee: MyndTec Inc., Mississauga, Ontario ( * ) Notice: Subject to any disclaimer, the term of this patent is extended or adjusted under 35 U.S.C. 154(b) by 0 days.

(21) Appl. No.: 14/411,200

(22) PCT Filed: Jun. 26, 2013

(86) PCT No.: PCT/CA2013/050499
§ 371 (c)(1),
(2) Date: Dec. 24, 2014

(87) PCT Pub. No.: WO2014/000107
PCT Pub. Date: Jan. 3, 2014

(65) Prior Publication Data
US 2015/0148866 A1   May 28, 2015

Related U.S. Application Data

(60) Provisional application No. 61/664,306, filed on Jun. 26, 2012.

(51) Int. Cl.
A61N 1/36     (2006.01)
A61N 1/04     (2006.01)

(52) U.S. Cl.
CPC ....... *A61N 1/36003* (2013.01); *A61N 1/0452* (2013.01); *A61N 1/0492* (2013.01); *A61N 1/36014* (2013.01)

(58) Field of Classification Search
CPC ............ A61N 1/36003; A61N 1/36014; A61N 1/0452; A61N 1/0492
See application file for complete search history.

(56) References Cited

U.S. PATENT DOCUMENTS

| 5,330,516 | A |   | 7/1994 | Nathan |
| 6,094,599 | A | * | 7/2000 | Bingham ........... A61N 1/36014 607/149 |
| 8,165,685 | B1 |  | 4/2012 | Knutson et al. |
| 2004/0082979 | A1 |  | 4/2004 | Tong et al. |
| 2009/0326607 | A1 |  | 12/2009 | Castel et al. |
| 2010/0161003 | A1 |  | 6/2010 | Malmberg et al. |

OTHER PUBLICATIONS

International Search Report for corresponding patent application No. PCT/CA2013/050499 dated Sep. 13, 2013.
European Search Report and Written Opinion mailed May 4, 2016 for corresponding Patent Application No. EP13809036.0.
(Continued)

*Primary Examiner* — Rex R Holmes
(74) *Attorney, Agent, or Firm* — Renner, Otto, Boisselle & Sklar, LLP

(57) ABSTRACT

A functional electrical stimulation method for rehabilitating, treating, retraining, and/or otherwise improving upper extremity mobility and control in persons having impaired or disabled upper extremities due to stroke or spinal cord injury, comprising stimulation of the lumbricalis muscles.

11 Claims, 63 Drawing Sheets

(56) References Cited

OTHER PUBLICATIONS

Ying-Han C. et al.: "A digital signal processor based functional electrical stimulation system with its user interface design", Engineering in Medicine and Biology, 2002, 24th Annual Conference and the Annual Fall Meeting of the Biomedical Engineering Society EMBS/BMES Conference, 2002, Proceedings of the Second Joint, vol. 3, Oct. 23, 2002 (Oct. 23, 2002), pp. 2384-2385, XP10618491.
Hoshimiya, N. et al.: "Multi-channel Portable Functional Electrical Stimulation (FES) System for Clinical Usage", Engineering in Medicine and Biology Society, vol. 13, Oct. 31, 1991 (Oct. 31, 1991), p. 931, XP010102476.

\* cited by examiner

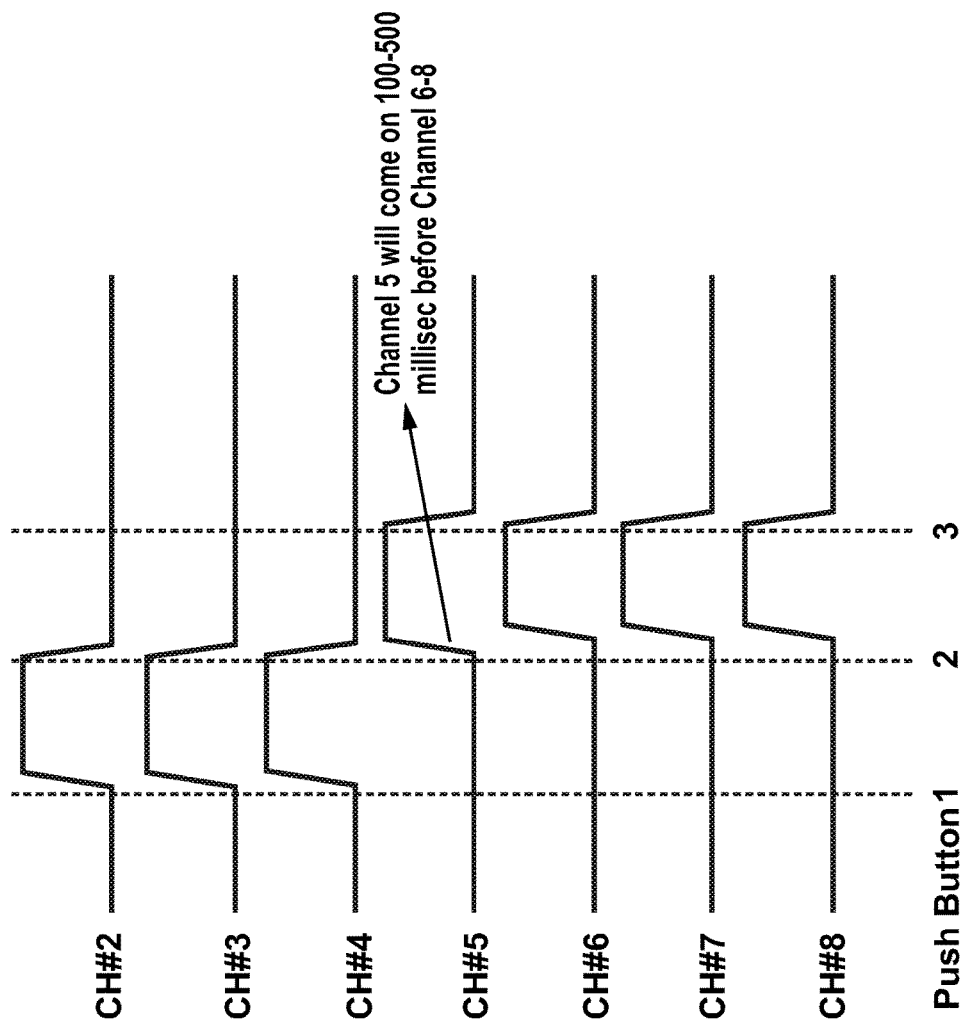

METHOD FOR FUNCTIONAL ELECTRICAL STIMULATION THERAPY

RELATED APPLICATIONS

This application U.S. national stage application claiming priority to International Application No. PCT/CA2013/050499 filed Jun. 26, 2013, which claims the benefit of U.S. Provisional Application No. 61/664,306, each of which is hereby incorporated herein by reference in their respective entireties.

FIELD OF THE INVENTION

The invention relates to a method for rehabilitating, treating, retraining, and/or otherwise improving upper extremity mobility and control in persons having impaired or disabled upper extremities due to stroke or spinal cord injury.

BACKGROUND OF THE INVENTION

It has been estimated that 55% of stroke survivors have a nonfunctional (paralyzed) upper extremity following their stroke. A further 30% have partial use of their upper extremities, with limited range of motion and strength. Most victims of stroke are unable to perform their activities of daily living in the same manner as before the stroke, due to these limitations on motion and strength. Accordingly, one of the most common symptoms in a stroke survivor is mild to severe paresis of an upper extremity.

Likewise, one of the more common effects of spinal cord injury is nonfunctional or limited function to the upper extremities. It has been estimated that 50% of the spinal cord injured individuals have some level of upper extremity impairment.

Treatment options, especially for those with severe paralysis of the upper extremity, are extremely limited. Constraint-induced movement therapy has been shown to be effective in recovering upper limb function, but only for mild paresis, for example, where patients are able to independently extend the fingers and wrist to some extent. Other new therapies are being explored, including robot-assisted therapy, biofeedback therapy, and virtual reality training. However, to date, these therapies have shown promise for individuals with mild paresis only.

Functional electrical stimulation (FES) therapy has been tested as interventions for acute and chronic stroke. For example, the NESS Handmasterm™ (also know as Bioness™ H200 system) is a multichannel neuroprosthesis, worn by the patient. Training with the device led to gains in small randomized trials, as an intervention for grasping impairment in both chronic hemiparesis and subacute hemiparesis due to stroke. In these studies, the device was used for 12 weeks, and positive results were seen as an increase in volitional hand tests for the FES group in contrast to a control group that performed task-oriented training without FES. Other studies have implemented FES therapy, and have demonstrated modest improvements in terms of upper extremity function and spasticity following 6 weeks and 18 weeks of use, both in home-based programs, and in clinical settings under the supervision of a trained FES practitioner.

Several stimulation systems in addition to the NESS Handmaster are known; most use several surface electrodes, a multi-channel stimulator and a pre-programmed sequence of stimulation that can be triggered by a switch, several switches, or signals from a sensor. Other stimulation systems use implantable electrodes, or fully implantable systems that use a pre-programmed stimulation that is controlled by a switch or sensory signal in an open- or closed-loop control scheme.

Most of the prior art stimulation systems comprise stimulation of more than one muscle group in patients with mild paresis. One of the more complex prior art systems is described in US 2004/0147975 A1 (incorporated herein by reference in its entirety) which describes electrical stimulation of neural pathways using a stimulation pattern that mimics natural flow of neural activities to the impaired upper extremity; generating the missing components of a functional movement in parallel with the voluntary exercising of the same functional movement based on the said patterned stimulation of the efferent neural pathways time-synchronized with volitional movement; and enhancing the afferent input by the said patterned electrical stimulation in time synchrony with the biological afferent activity caused by the functional movement of the limb. The published application teaches that therapy for motor relearning in persons with paresis caused by stroke should support a process of relearning optimally by functionally assisting the user to perform intended activities, which they may only be able to perform poorly or not without assistance. It is taught that the sensory feedback associated with the process of the activities assists with the relearning process of the brain. The publication teaches that the patterned stimulation of the muscles is synchronized with volitional movement or volition of movement (whether or not the patient is capable of any relevant movement without the stimulation); the electrical signals are perceived by the patient, which provides an enhanced afferent input in synchrony with biological afferent activity, i.e. exteroceptive signals as well as proprioceptive signals. The publication also teaches a control algorithm that causes the stimulator to provide stimulation patterns of muscle-inducing electrical signals which mimic the timing and modulation of muscles typically active in able-bodied humans, with signals including non-simultaneous peaks of activation of agonist and antagonist muscles during a single direction of movement, and appropriate coactivation of agonist and antagonist muscles needed for a desired functional movement. The patent teaches stimulation of finger flexors, finger extensors, thumb extension/adduction, and thumb opposition/flexion. Optionally, forearm flexion and extension, as well as forearm supination and pronation are stimulated.

It would be advantageous to provide a stimulation system that provides improved re-training and improved mobility and strength in patients with both mild and severe paralysis of upper extremities, caused by stroke or spinal cord injury.

BRIEF DESCRIPTION OF THE FIGURES

FIGS. 8,10, 13-16, 19, 20,22,23,26,30,31,34,37,38,42-45, 50,51,55,56,60,62 and 63 show, in schematic form, the order of delivery of electricity through electrodes surface attached to various portions of the arm and hand for various protocols of the invention.

SUMMARY OF THE INVENTION

Figure 1:
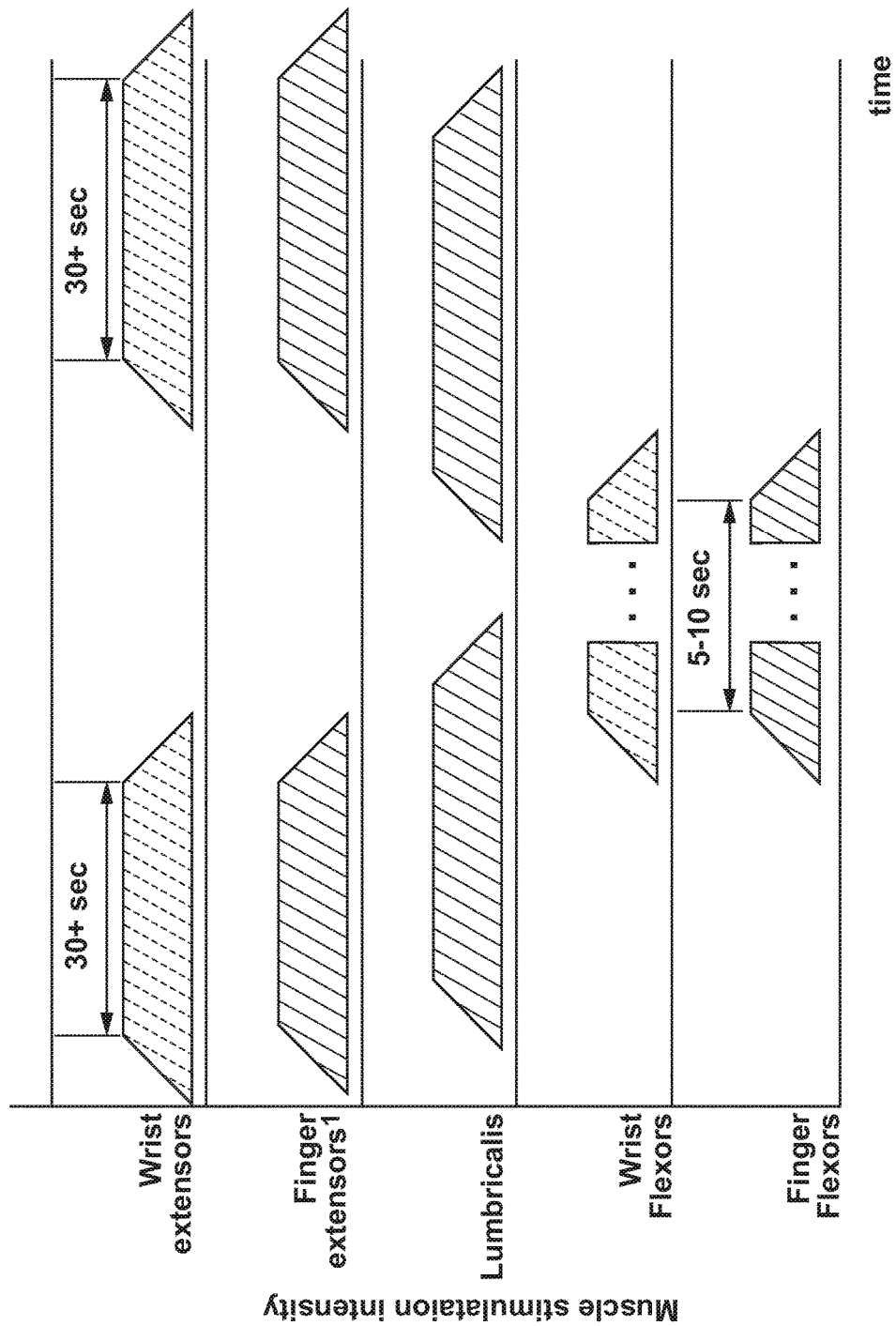
FIG. 1 shows, in schematic form, the order of delivery of electricity through electrodes surface attached to various portions of the arm and hand to provide one exemplification of the presently claimed therapy.

According to one aspect of the present invention is provided a method for functional electrical stimulation therapy comprising a stimulation of at least one lumbricalis muscle in a hand.

In certain embodiments, the method further comprises a stimulation of at least one interossei muscle of the same hand. According to certain embodiments of the present invention, the stimulation of the at least one lumbricalis muscle and the at least one interossei muscle comprises: placing at least one electrode on a proximal phalanx of a finger, proximal to a metacarpopharangeal joint, on said hand (or, alternatively, placing at least one electrode between the metacarpals) placing an anode on the proximal and posterior part of a wrist on said hand; passing an electric current through the at least one electrode to the anode.

According to certain embodiments of the present invention, the electric current has an amplitude of 5-20 mA. However, amplitude may be both device and patient dependent, and with some devices, amplitudes of lower than 5 mA, for example, of 1-2 mA, or even in some cases lower than 1 mA, may be sufficient.

According to certain embodiments of the present invention, the amplitude is about 8-10 mA.

According to certain embodiments of the present invention, the electrical current has a pulse frequency of 16-100 Hz, for example between 20-80 Hz, or about 40 Hz.

According to certain embodiments of the present invention, the electric current has a pulse duration of 150-600 microseconds, for example about 300-450 microseconds or about 400 microseconds. However, pulse duration may be device dependent, and with some devices, pulse duration may be shorter.

According to certain embodiments of the present invention, the method further comprises stimulation of at least one finger extensor muscle of the same hand.

In certain embodiments, the stimulation of the at least one finger extensor muscle is stimulated through an electrical pulse.

In certain embodiments, the electrical pulse has a frequency of 16-100 Hz, for example, 20-80 Hz or about 40 Hz.

In certain embodiments, the electrical pulse has a pulse duration of 150-400 microseconds, for example, about 200-300 microseconds, or 250 microseconds.

In certain embodiments, the electrical pulse has an amplitude of about 10-35 mA, for example, about 15-25 mA or about 18 mA. However, amplitude may be both device and patient dependent, and with some devices, amplitudes of lower than 5 mA, for example, of 3-2 mA, or even in some cases lower than 2 mA, may be sufficient.

According to certain embodiments of the present invention, the amplitude is about 15-25 mA.

In certain embodiments, the stimulation of the at least one finger extensor occurs before the stimulation of the at least one lumbricalis muscle.

In certain embodiments, the stimulation of the at least one finger extensor occurs within 200 milliseconds of the stimulation of the at least one lumbricalis muscle.

In certain embodiments, the method comprises the following steps: (a) Stimulation of the at least one finger extensor muscle; (b) Stimulation of the at least one lumbricalis muscle; (c) Relaxation of the at least one lumbricalis muscle; and (d) relaxation of the at least one finger extensor muscle. In certain embodiments, these steps are repeated between 5 and 30 times.

In certain embodiments, the method comprises the following steps: (a) stimulation of the at least one finger extensor muscle; (b) stimulation of the at least one lumbricalis muscle; (c) Relaxation of the at least one finger extensor muscle; (d) stimulation of the at least one finger extensor muscle; (e) relaxation of the at least one lumbricalis muscle; and (f) relaxation of the at least one finger extensor muscle. In certain embodiments, steps d-e are repeated at between 5 and 30 times.

In certain embodiments, the method comprises the following steps: (a) stimulation of the at least one finger extensor muscle; (b) stimulation of the at least one lumbricalis muscle; (c) relaxation of the at least one finger extensor muscle; (d) stimulation of at least one finger flexor muscle; (e) relaxation of the at least one lumbricalis muscle; and (f) relaxation of the at least one finger flexor muscle. In certain embodiments, steps d-e are repeated at between 5 and 30 times.

In certain embodiments is provided a method for stimulation of a lumbricalis muscle on a hand, comprising: (a) placing at least one electrode on a proximal phalanx of a finger, proximal to a metacarpopharangeal joint, on said hand; (b) placing an anode on the proximal and posterior part of a wrist on said hand; and (c) passing an electric current through the at least one electrode to the anode.

In certain embodiments, the method comprises the following steps: (a) stimulation of the at least one finger extensor muscle; (b) stimulation of the at least one lumbricalis muscle; (c) relaxation of the at least one finger extensor muscle; (d) stimulation of at least one finger flexor muscle; (e) relaxation of the at least one lumbricalis muscle; (f) stimulation of the at least one lumbricalis muscle; (g) relaxation of at least one finger flexor muscle; (h) stimulation of at least one finger extensor muscle; (i) relaxation of the at least one lumbricalis muscle; and (j) relaxation of the at least one finger extensor muscle. In certain embodiments, steps d-e are repeated at between 5 and 30 times.

A further aspect of the invention is an apparatus for providing the method, comprising a multi-channel stimulator having at least 3 channels, for example, at least 10 channels.

In certain embodiments, the apparatus is preprogrammed to, upon activation, automatically provide at least one of the methods herein described, to a patient connected thereto.

In certain embodiments, the apparatus can be preprogrammed to provide a plurality of such methods, upon selection of a desired protocol by a user. For example, the apparatus can be preprogrammed to provide at least three, or four, or twelve of the methods herein described.

In certain embodiments, the methods are preprogrammed at the factory. However, the protocols may be added or modified by the user, by means of an input means on or connected to the apparatus.

In certain embodiments, the protocol is selected by means of a patient input means, such as a USB fob or RFID chip identifying a specific patient, for example, by a confidential patient identification number, or a specific protocol.

Also provided is a kit for performing functional electrical stimulation therapy, comprising an apparatus as herein described, a plurality of electrodes which are capable of functionally attaching thereto; and instructions for use.

DETAILED DESCRIPTION

Described is a new method for rehabilitating patients with impaired or disabled upper extremities due to stroke or spinal cord injury, for example, spinal cord injury at the C3-C7 vertebrae causing bilateral loss of control of wrist and fingers. The method is based on the unique discovery that certain muscle groups, previously never utilized in functional electrical stimulation (FES) therapy, provide dramatic improvement in therapy outcome when utilized. Specifically, it has been found that the stimulation of the lumbricalis muscle groups significantly improve outcomes of FES treatment. It has also been found that FES treatment including stimulation for lumbricalis muscles provides significantly improved outcomes in not only the patients with mild paresis, but also those with severe paresis, including in those previously condemned to complete paralysis of the hand and arm.

In addition to the novel stimulation protocols utilizing the lumbricalis muscle groups, further novel stimulation protocols have been invented which provide improvement in therapy outcome, and which do not utilize the lumbricalis muscle groups.

Accordingly, we have found a new method of treating patients using FES. This method works well with patients with both mild and severe upper extremity paresis. The method relates to improving: a) the palmar grasp, used to hold large, heavy objects such as cans and bottles; b) the lateral pinch grasp, used to hold small, thin objects such as keys and paper between the thumb and the fully flexed index finger; and c) pinch grasp, used to hold small, thin objects such as die and marble between the thumb and the index finger. The method also provides improvement in "at rest" tonality and provides the patient with a significantly more normal posture and resting position for their hands and arms.

The therapy comprises repeated execution of various reaching and grasping tasks. The FES therapy involves electrical stimulation of neural pathways, using a stimulation pattern that mimics natural flow of neural activities to the impaired upper extremity, which includes, in many embodiments, activation/stimulation and release of the lumbricalis muscles. In preferable embodiments, the patient is directed to voluntarily exercise the same functional movement in a time-synchronized manner, enhancing the electrical stimulation input with biological activity, and retraining the nervous system to move the limb; thus the method provides an opportunity for "relearning" by functionally assisting the patient to perform intended activities, which they may only be able to perform poorly or not without assistance. The sensory feedback associated with the process of the activities will assist the relearning process of the brain.

The method is similar to known methods, such as those previously described, in that wrist and/or finger extensors are activated and released, and that, in many exemplifications, task specific exercises, such as arm reaching, opening and grasping of object movements are performed. However, the stimulation and use of the lumbricalis muscles, either alone or as part of an otherwise conventional FES treatment, dramatically improve patient re-training and outcomes. Also described are further novel stimulation protocols, to be used in combination with the lumbricalis-based protocols or alone, which do not specifically activate the lumbricalis muscles.

Thus, in general, in certain embodiments, the method comprises an order of muscle stimulation and release as follows:

1) Stimulating the finger extensor (and, optionally, wrist extensor) muscles;
2) Stimulating the lumbricalis muscles;
3) Releasing the finger extensor (and, optionally, wrist extensor) muscles;
4) Optionally, stimulating the finger flexor muscles (and, optionally, wrist flexors);
5) Optionally, releasing the lumbricalis muscles.
6) Maintaining the finger flexion (and, optionally, wrist flexion) muscles as long as the patient is expected to hold an object.
7) To release the object the lumbricalis muscles are contracted first followed by the relaxation of finger flexor (and, optionally, wrist flexor) muscles which is then followed by the contraction of finger extensor (and, optionally, wrist extensor) muscle to generate hand opening.
8) Once the object is released all muscles are relaxed.

Figure 2:
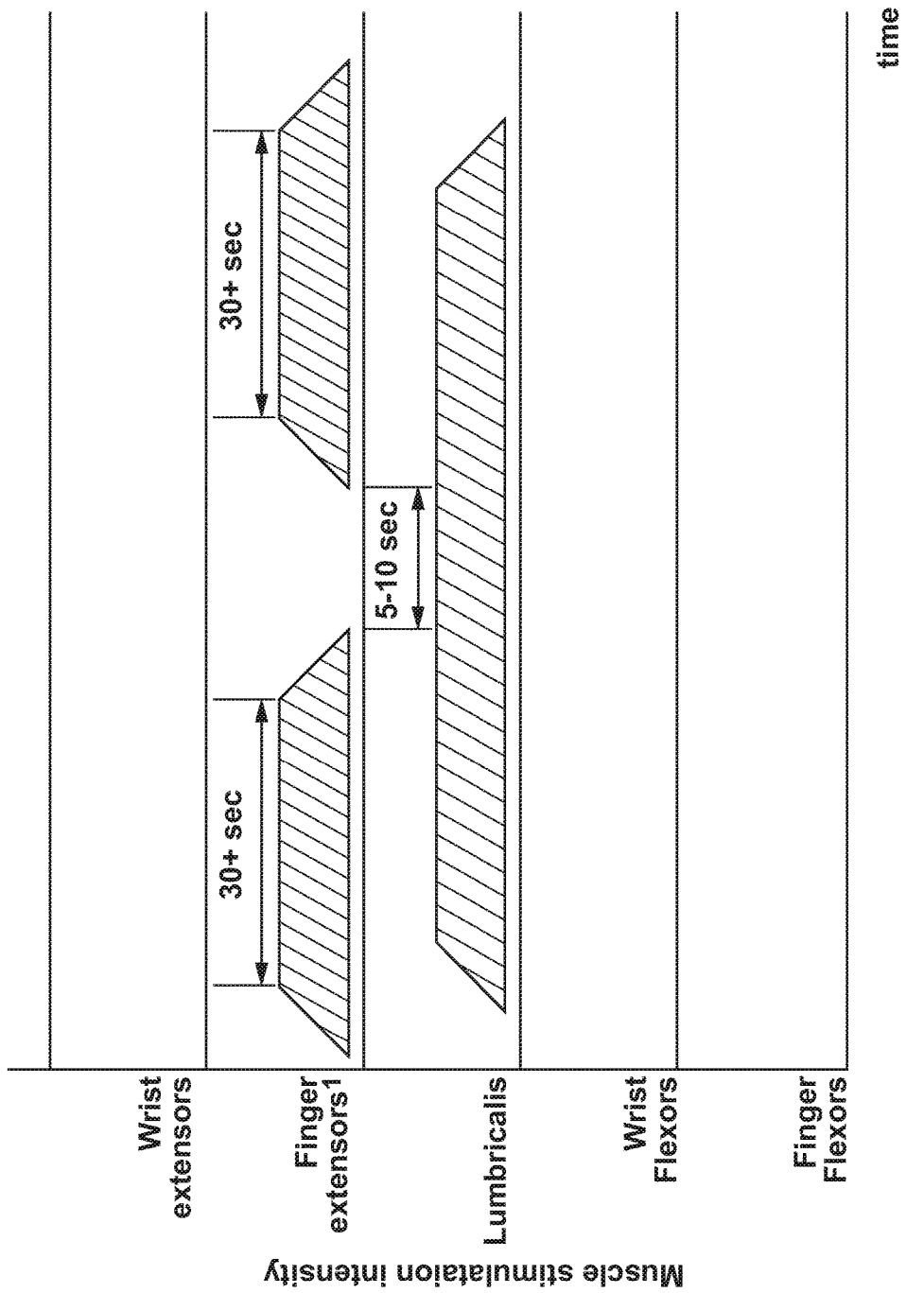
FIG. 2 shows, in schematic form, the order of delivery of electricity through electrodes surface attached to various portions of the arm and hand to provide a further exemplification of the presently claimed therapy.
Figure 3:
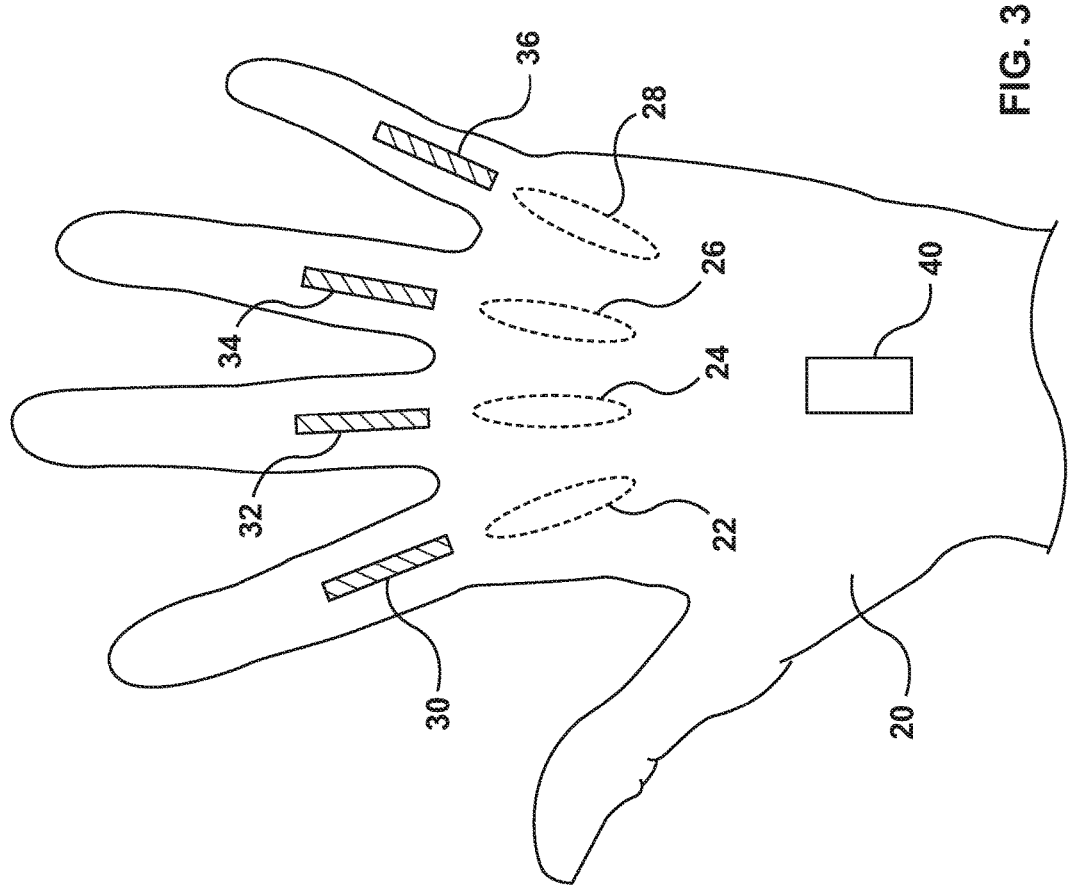
FIG. 3 shows, in schematic form, electrode placement for activation of the interossei and lumbricalis muscles.

Although the order, above, is typical, releasing of the muscles is often done incrementally, by a gradual reduction in the amount of energy imparted through the electrodes. Similarly, stimulation of the muscle groups is not necessarily an "on/off" process; when mimicking the normal activation of muscles when a person grips an object, gradual stimulation through a gradual increase in energy imparted through the electrodes is desirable. Thus, there may be overlaps between, for example, the releasing of the wrist extensor muscles and the releasing of the lumbricalis muscles, or any two or more of the steps described above. A typical stimulation protocol is shown in FIG. 1. We have also found that continuous stimulation of lumbrical muscles coupled with stimulation of finger extensors provides hand opening. The stimulation of the lumbrical muscles using electrode placement in FIG. 3 results in stimulation of the interossei muscles as well. Stimulation of interossei muscles is responsible for "finger fanning" during finger extension. In the case when the lumbrical and interossei muscles are contracted jointly with the finger extensors and the finger extensors are relaxed the fingers go into an "L" shaped flexion. By simply activating and relaxing the finger extensors while the lumbrical and interossei muscles are contracted one can generate finger extension followed by finger flexion (FIG. 2) which also provides improved patent rehabilitation outcomes. In some stroke patients one does not need to generate finger flexion as they my have some voluntary finger flexion and they only need help with finger extension, while they are able to generate finger flexion them selves. It would be understood and contemplated, of course, by a person knowledgeable in this field, that the exercises described herein could be incorporated into otherwise conventional FES therapies, such as task specific exercises, like arm reaching, and opening and grasping of object movements.

Though stimulation of extensor digitorum muscles alone may work reasonably well in spinal cord patients with mild paresis, in patients debilitated by stroke, for example, those with severe paresis, the flexor tone in the finger flexors is so strong that stimulation of extensor digitorum generates metacarpophalangeal joint extension, but the interphalangeals remain flexed. This results in an incomplete, or improper, finger extension. As such, stroke victims with severe paresis cannot actually open their hand using prior art electrical stimulation methodologies. It has been surprisingly found that coordination of stimulation of extensor digitorum muscle groups with stimulation of the lumbricalis muscles, allows for proper hand opening in stroke patients with severe tone. This allows much better hand movement while performing the electrical stimulation, and also provides for a dramatic improvement in re-education and rehabilitation outcomes.

Treatment protocols can be modified for exercising and rehabilitating various grasps, such as the palmar grasp, the lateral pinch grasp and the pinch grasp. For example for the palmar grasp, all of the finger (fingers 2-5) and thumb (finger 1) extensor muscles are stimulated simultaneously to open the hand, and all finger and thumb flexor muscles are stimulated simultaneously to close the hand. For the lateral pinch grasp, all of the finger and thumb extensor muscles are stimulated simultaneously to open the hand, and all finger flexor muscles are stimulated followed by the thumb flexor muscles to close the hand into the lateral pinch grasp posture. Finally, for the pinch grasp all of the finger and thumb extensor muscles are stimulated simultaneously to open the hand, but only index finger (finger 2) and thumb (finger 1) flexors are stimulated simultaneously to generate the pinch grasp.

Though implanted electrodes may be used, in certain, preferable, embodiments, the treatment is performed through the placement and activation of electrodes on the surface of the skin. It has been surprisingly found that stimulation of the lumbricalis muscle groups can be performed quite effectively through placement of electrodes on the surface of the skin, by placing the electrodes not proximal to the lumbricalis muscle groups, but rather by placing the electrodes and the ground such that the lumbricalis muscles are located between the electrodes and the ground. An optimal placement of electrodes for stimulation of lumbricalis muscles is depicted, in schematic form, in FIG. 3. A patient's hand 20 is illustrated, with the approximate position of the lumbricalis muscles 22, 24, 26, 28 shown (As depicted, lumbrical I (22), lumbrical II (24), lumbrical III (26) and lumbrical IV (28). Electrodes 30, 32, 34, 36 are placed on the posterior aspect of the proximal phalanx of fingers, as close as possible to the metacarpopharangeal joint.

The electrodes 30, 32, 34, 36 are cathodes (i.e. electrodes that will generate a negative charge followed by a positive charge). We have found that the size and shape of the electrodes 30, 32, 34, 36 can vary significantly while still providing excellent effect. Preferably, electrodes 30, 32, 34, 36 are configured such that they approximately mirror the length and width of the posterior aspect of the proximal phalanx, for example, for an average sized male, approximately 1×2.5 cm. However, electrodes 30, 32, 34, 36 may be as small as 50% of the skin surface of the posterior aspect of the proximal phalanx and still have excellent effect. In some applications, use of only electrodes 30, 32, 34 or 30, 34 can be used to generate less specific yet in some patients equally effective lumbricalis extension and flexion.

A common grounding anode 40 is placed on the proximal and posterior part of the wrist. We have found that this electrode placement provides excellent stimulation of both the lumbrical and the dorsal interossei muscles. Note that, throughout this specification, when referring to stimulation of the lumbrical or lumbricalis muscles, this refers also to the simultaneous or near simultaneous stimulation of the interossei muscles. Stimulation of the lumbrical muscles provides extension of the interphalangeals (both proximal to medial phalanges and medial to distal phalanges). At the same time, stimulation of the lumbrical muscles also generates flexion of the metacarpophalangeal joints. This results in an "L" shape in the hand. Thus proper finger extension is obtained in combination with stimulation of the extensor digitorum muscles, which extend the phalanges of fingers 2-5. Simultaneous stimulation of the interossei muscles causes finger abduction and adduction, and results in fanning of the fingers during finger extension. This produces excellent finger extension, with all fingers fully extended and fanned. This is in dramatic contrast to the existing stimulation protocols, which do not stimulate the interossei muscles, or even the lumbrical muscles, and thus are unable to deliver the same amount of finger extension and fanning, which is critical for stroke patients, who are typically unable to open the hand and extend fingers.

We have found that stimulation of the lumbrical muscles on their own will not generate the desired finger extension, but, rather, the stimulation must be coupled with the stimulation of extensor digitorum muscles. One of the reasons for this is that, for the presently described method of stimulating the lumbrical muscles, the wrist must be in partial or full extension, so that the electrical field and/or currents actually flow through, and stimulate, the lumbrical muscles. Therefore, it has been found that stimulation of the extensor digitorum muscles must occur before, or at least simultaneously, with the stimulation of the lumbrical muscles to generate the desired finger extension. We have found that stimulation of the extensor digitorum muscles 100 to 500 milliseconds before the stimulation of the lumbrical muscles, preferably 100-200 milliseconds before, provides excellent finger extension. Note that stimulation of the lumbrical muscles, on their own, is still a useful and advantageous rehabilitation therapy.

Once a good finger extension is obtained in the manner described above, one can decrease the extensor digitorum muscle stimulation, to generate finger flexion using stimulation of the extensor digitorum muscles and the lumbrical muscles. Thus, it has been found that by using a constant stimulation of the lumbrical muscles, one can obtain excellent opening and closing of the hand using only the extensor digitorum muscles (see FIG. 2). Thus, for this therapy, the order of stimulation is as follows:

1) Stimulating the finger extensor muscles;
2) Stimulating the lumbricalis muscles;
3) Releasing the finger extensor muscles;
4) Stimulating the finger extensor muscles;
5) Repeating (3) and (4) to obtain repetitive opening and closing of the hand, ending with (3);
6) Releasing the lumbricalis muscles.

This methodology was found to provide excellent training of the opening and closing of the hand.

In most stroke patients, both flexors and extensors are naturally "flexed", i.e. activated, but since flexors are generally stronger muscles this results in the characteristic hand and arm shape (clenched, contracted, and at the side of the body). As such, most therapies, such as the therapy shown immediately above, have focused on the finger and wrist extensor muscles to open the hand and wrist, allowing the 'natural' flexor tone to close the fingers and wrist. Thus, many therapies have simply had the following order of stimulation: (1) stimulating the finger extensor muscles and/or the wrist extensor muscles; (2) releasing the finger extensor muscles and/or wrist extensor muscles; waiting for the flexors to 'naturally' close the hand; then repeating step (1). We have found that stimulation of the finger flexors can be coupled with the closing of the hand, and that this provides added benefit in re-training and rehabilitation.

Thus, in certain embodiments of the present invention, the order of stimulation is as follows:

1) Stimulating the finger extensor muscles;
2) Stimulating the lumbricalis muscles;
3) Releasing the finger extensor muscles;
4) Stimulating the finger flexor muscles;
5) Releasing the finger flexor muscles;
6) Stimulating the finger extensor muscles;
7) Repeating (3)-(6) to obtain repetitive opening and closing of the hand, ending with (3);
8) Releasing the lumbricalis muscles.

Unlike spinal cord injured patients, where discrete engagement of the all five fingers in needed, in stroke patients it has been found that stimulation of the finger flexors does not require discrete engagement of all five fingers, but rather one electrode pair can be used for fingers 2-5 and one electrode pair for thumb (finger 1). The cathode for fingers 2-5 should be placed above the finger flexors (both superficialis and profundus); it was found that a cathode of approximately 5×5 cm, placed in this position, was able to generate flexion of fingers 2-5 in a manner suitable for therapy. The circuit was closed using a single 5×5 cm common anode (ground), placed on the proximal and anterior part of the wrist. As for the thumb flexion the cathode has to be place over the thenar prominence or over the medina nerve to help place the thumb in opposition to fingers 2-5. The thumb stimulation circuit was closed using the same 5×5 cm common anode placed on the proximal and anterior part of the wrist. It was also found that in some patients stimulation of the thumb flexor (finger 1) was optional, since, in stroke patients, it was found that when finger flexors 2-5 are stimulated, the thumb would often follow on its own.

Since finger flexors are naturally 'activated' in stroke patients, it was found that, even when stimulation of these muscles were used, it did not need a duration of action as long as the extensor muscles. For example, in certain embodiments, a preferable stimulation pattern included stimulating the finger flexor muscles for only about 5-10 seconds, while stimulation of the finger extensors would last 30 seconds or more. For example:

1) Stimulating the finger extensor muscles (30+ seconds);
2) Stimulating the lumbricalis muscles shortly following finger extensor stimulation (continuously);
3) Releasing the finger extensor muscles (1-2 seconds);
4) Stimulating the finger flexor muscles (7 seconds);
5) Releasing the finger flexor muscles (1-2 second);
6) Stimulating the finger extensor muscles (30+ seconds);
7) Repeating (3)-(6) between 20-30 times to obtain repetitive opening and closing of the hand, ending with (3);
8) Releasing the lumbricalis muscles.

See FIG. 1, for example, for details.

The purpose of the short flexion, followed by long extension, was to cause the tone of the finger flexors to be reduced from its "stroke-natural" high tone to a reduced tone that would allow relaxing of the arm and hand. We call this process agonist/antagonist inhibition. We have found that activation of flexors and extensors in this manner allow for a decrease in tone of both flexors and extensors, which occurs within 4-5 minutes into the protocol. An added benefit is that, since the flexor contractions are very short as compared to the extensors, the extensors obtain more 'exercise', building these muscles while not building the flexors. This changes the power balance between flexors and extensors, further reducing flexor tone and allowing the hand to relax into a more natural state, and eventually allow voluntary hand opening and closing.

Figure 4:
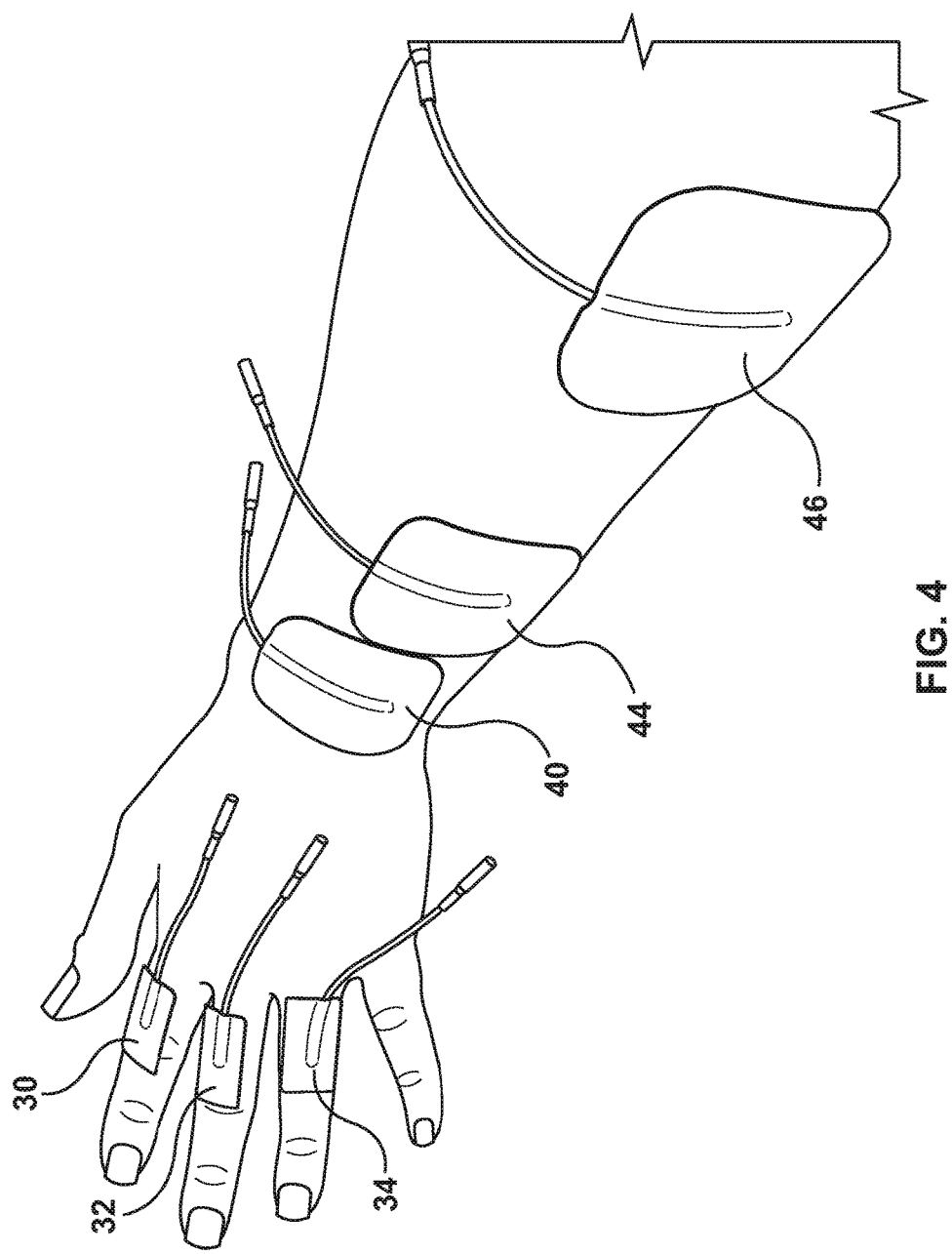
FIG. 4 shows a photographic representation of electrode placement for activation of interossei and lumbricalis muscles, as well as finger extensor muscles.
Figure 5:
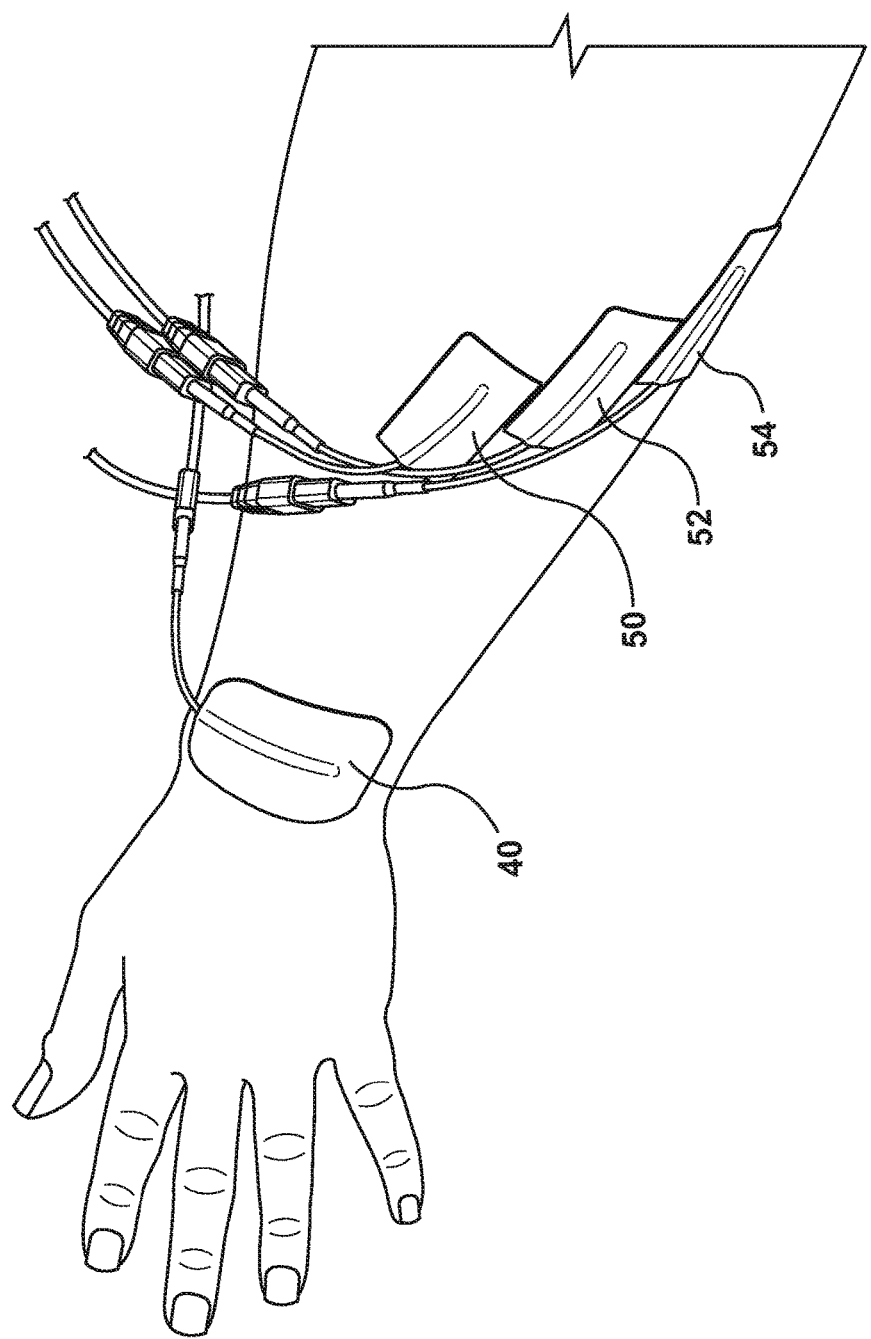
FIG. 5 shows a photographic representation of electrode placement for activation of finger extensor muscles only, without activation of interossei and lumbricalis muscles, with electrodes placed so that individual finger (fingers 2-5) extensor muscles can be targeted.

When performing the treatment using surface-placed electrodes, electrode placement for stimulation of the wrist and finger extensors, as well as for the finger and wrist flexors, can be as previously taught in the art. However, we have found that stimulation of the finger extensors can be performed using a single 5×5 cm cathode electrode, placed immediately above each of the two extensors, as shown in FIG. 4 (electrode 46). The electrical circuit for the extensors is competed using an anode electrode, which can be the same anode electrode used for the stimulation of the lumbrical muscles, with placement as described above, shown as anode 40. Alternatively, a separate anode electrode can be used, located next to anode 40 on the proximal side of the electrode (electrode 44). In certain embodiments, where separate fingers are targeted, as described in more detail below, 2 or 3 cathode electrodes, each 1-1.5 cm wide and 3 cm long are placed above the finger extensor muscles, as shown in FIG. 5 (electrodes 50, 52, 54). In certain cases, depending on the size of the individual, smaller electrodes, and, for example, circular electrodes of similar dimension can be utilized. This placement, as shown in FIG. 5, can selectively stimulate finger extension, through stimulation of finger extensor muscles, of one or two fingers individually, with each of electrodes 50, 52, and 54 selecting an individual finger extensor muscle.

Typically, we have found that the following stimulation parameters work well: a pulse frequency of 16-100 Hz, preferably 20-80 Hz, at a pulse duration of 150-600 microseconds, preferably 300-450 microseconds, or about 400 microseconds. Pulse amplitudes are highly patient-specific, and can be modified, for example, increased until the desired hand, finger, or wrist movement is exhibited. Pulse amplitudes are also highly device-specific, with different device and electrode designs requiring dramatically different pulse amplitudes. However, once the pulse amplitude has been determined for a specific patient, it is typically fairly constant. In certain embodiments, we have found that pulse amplitudes for extensors and flexors have worked well at about 10-35 mA, preferably about 15-25 mA, with lumbricalis muscle stimulation having a lower amplitude, generally between 5-15 mA, preferably about 8-10 mA. With other device designs, in the same patient, we have found that pulse amplitudes in the 0.5-2 mA range are sufficient. It will be readily apparent what pulse amplitude would be required with a certain device, on a certain patient, at the first application, since the amplitude can start low, and be increased until the desired hand, finger, or wrist movement is exhibited.

The invention is embodied by the following examples, which are not meant to be limiting:

Example 1

Treatment of Patients with FES Protocol

Hemiplegic patients who had been hospitalized due to a recent (≤6 month) stroke were recruited. Patients had a score of 1 or 2 for combined arm and hand on the Chedoke-McMaster Stages of Motor Recovery (CMSMR), which is defined as spastic of flaccid paralysis of the arm and hand, with little or no voluntary movement. The time between stroke and the start of treatment was not less than 2 weeks following stroke. A second group who had been hospitalized due to recent (≤6 month) incomplete and complete C3 to C7 spinal cord injury. At admission to the study, patients were unable to grasp and release objects with both hands. The time between spinal cord injury and the start of treatment was not less than 2 weeks following spinal cord injury.

Similarly, patients who had suffered from their stroke or spinal cord injury more than 6 months previously, up to 10-20 years post-stroke or post-spinal cord injury, were provided with the treatment.

Each participant underwent a series of assessments immediately before and after treatment; patients were placed in two treatment groups: one group was given the Lumbricalis Protocol (FES group), as described below, a second group (non-FES group) was provided with the "best practices" conventional occupational therapy and physiotherapy, which included prior art electrical stimulation for muscle strengthening and pain management, for a conventional amount of time (one session per day, 5 days a week for 8 weeks, or one session per day, 3 days a week for 12-16 weeks, or two session per day, 5 days a week for 4 weeks, with each therapy session lasting 45 minutes).

Conventional therapy (non-FES group) consisted of the following (1) muscle facilitation exercises emphasizing the neurodevelopmental treatment approach; (2) task specific, repetitive functional training; strengthening and motor control training using resistance to the patient's volitional movements; and (3) electrical stimulation applied primarily for isolated muscle strengthening (not for functional training); (4) activities of daily living including self-care where the upper limb was used to assist if appropriate; and (5) caregiver training.

Patients in the FES protocol group (FES group) received treatment using 4 lumbricalis-based protocols discussed below and series of other protocols discussed further in the document. The order of the deployment of the protocols was patient depended and was chosen based on the patients hand function and therapists clinical decision which protocols should be deployed at which state of the therapy. The muscles recruited and resulting movements were summarized as follows. Therapy was provided for an amount of time similar to controls—one session per day, 5 days a week for 8 weeks; or one session per day, 3 days a week for 12-16 weeks; or two session per day, 5 days a week for 4 weeks—with each therapy session lasting 45 minutes. When improvement began to plateau, patients were moved to the next phase of treatment.

Protocol 1: Lumbricalis-Finger Extension Protocol #1

To ensure that the finger tone/flexion posture typical for these severe stroke patients is disrupted, and that fingers can be opened, the patients were first subjected to a lumbricalis-finger extension protocol. Three cathode electrodes and a ground electrode were placed as described in FIG. 3. Briefly, electrodes 30, 32, 34, 36 were placed on the posterior aspect of the proximal phalanx of fingers, as close as possible to the metacarpopharangeal joint. The electrodes 30, 32, 34, 36 were cathode electrodes (i.e. electrodes that will generate a negative charge followed by a positive charge). Electrodes 30, 32, 34, 36 were configured such that they approximately mirror the length and width of the posterior aspect of the proximal phalanx, and were approximately 1×2.5 cm in size. A common grounding anode 40 was placed on the proximal and posterior part of the wrist.

The lumbrical muscles were stimulated by following the following protocol:

1) Stimulation of the finger extensor muscles through a train of electric pulses, which amplitude is 20 mA, duration is 250 microseconds and frequency is 40 Hz. The train of pulses gradually increased from pulse amplitude 0 mA to 20 mA within about 2 seconds, remained at the 20 mA level for between 10 and 60 seconds (as performed, about 36 seconds), and was again decreased in intensity from 20 mA to 0 mA, within about 2 seconds. Note that, throughout these protocols, the timing of "about 2 seconds" could be as quick as 0.2 seconds.

2) After the finger extensors were fully contracted (about 2 seconds after the stimulation was initiated in extensors muscles) the stimulation of lumbrical and interossei muscles was initiated through a train of electric pulses, of an amplitude of 10 mA, duration of 250 microseconds and a frequency of 40 Hz. The train of pulses was then gradually increased from pulse amplitude 0 mA to 10 mA within about 2 seconds, was caused to remain at the 10 mA level for 10 to 60 seconds (as performed, about 32 seconds), and was caused to decrease in intensity from 10 mA to 0 mA within about 2 seconds. Although it was preferential that the finger extensors were stimulated first, followed by the stimulation of the lumbrical and interossei muscles, an alternative method, found to also be effective and appropriate, was to stimulate all these muscles simultaneously and to terminate their stimulation simultaneously. If the finger extensors were stimulated first, before the lumbrical and interossei muscles, the delay between activation of the lumbrical and interossei muscles following the finger extensors' activation could be as long as 2 seconds or as short as 0.1 seconds, or anywhere in-between these two values.

3) After the finger extensor, lumbrical and interossei muscles were all relaxed (ceasing electrical stimulation) and were caused to remain relaxed for about 40 seconds.

4) Steps (1), (2) and (3), above, were repeated for approximately 5 minutes.

5) Steps 1-4, above, were repeated for about 5-30 repetitions.

The pulse amplitude for lumbrical and interossei muscles was finely adjusted, between 5 and 12 mA, until an appropriate amount of movement was seen in the muscles, providing an "L" shape to the hand when stimulated. The pulse amplitude for finger extensors was finely adjusted, between 15 and 25 mA, until an appropriate finger extension and fanning is achieved when lumbrical and interossei muscles are stimulated at the same time as the finger extensor muscles.

This protocol was repeated until the hand exhibited a relaxed, unclenched state when at rest (typically 4-6 sessions), or when improvement was seen to plateau.

Protocol 2—Lumbricalis-Finger Extension Protocol #2

We have found that simultaneous stimulation of the lumbrical and interossei muscles jointly with finger extensor muscles, stimulated using a single electrode, while effective, may not always generate optimal finger extension. Therefore, it is sometimes desirable to couple the lumbrical and interossei muscle stimulation with the finger extensor muscle stimulation, where each branch of the finger extensor muscle (two branches of the extensor digitorum and one branch of the extensor digitorum minimi) are stimulated independently (i.e., electrode pair 40, 44 and 46 as shown in FIG. 4 and described in Protocol 1 were substituted with electrodes 40, 50, 52, 54 as shown in FIG. 5). Similar, as in Protocol 1 it was found that stimulation of the extensor digitorum muscles should occur before, or at least simultaneously, with the stimulation of the lumbrical and interossei muscles.

For this exercise, the order of stimulation was as follows:
1) Stimulation of the three finger extensor muscle branches through a train of electric pulses, with amplitudes of 15 mA, a duration of 250 microseconds and a frequency of 40 Hz. The train of pulses were gradually increased from pulse amplitude 0 mA to 15 mA within about 2 seconds, remained at the 15 mA level for between 10 and 60 seconds (as performed, about 36 seconds), and were then decreased in intensity from 15 mA to 0 mA within about 2 seconds.
2) After the finger extensors were fully contracted (about 2 seconds after the stimulation had been initiated in extensors muscles) the stimulation of lumbrical and interossei muscles was initiated through a train of electric pulses, with an amplitude of 10 mA, a duration of 250 microseconds and a frequency of 40 Hz. The train of pulses were gradually increased from pulse amplitude of 0 mA to 10 mA within about 2 seconds, remained at the 10 mA level for about between 10 and 60 seconds, (as performed, 32 seconds) and were then decreased in intensity from 10 mA to 0 mA within about 2 seconds.
3) Although it was preferential that the finger extensors were stimulated first, followed by the stimulation of the lumbrical and interossei muscles, an alternative method, found to also be effective and appropriate, was to stimulate all these muscles simultaneously and to terminate their stimulation simultaneously. If the finger extensors were stimulated first, before the lumbrical and interossei muscles, the delay between activation of the lumbrical and interossei muscles following the finger extensors' activation could be as long as 2 seconds or as short as 0.1 seconds, or anywhere in-between these two values. After the finger extensor, lumbrical and interossei muscles were all relaxed (ceasing electrical stimulation) and remained relaxed for 40 seconds.
4) Steps 1, 2 and 3, above, were repeated for approximately 5 minutes.
5) Steps 1-4, above, were repeated for about 5-30 repetitions;

As discussed above, once a good finger extension was obtained, using stimulation of the extensor digitorum muscles and the lumbrical muscles, one could decrease the extensor digitorum muscle stimulation, to generate finger flexion.

Protocol 3: Lumbricalis-Finger Extension Protocol #3

In patients where the Lumbricalis-Finger Extension Protocol outcomes began to plateau, patients were moved to this Protocol #3. In Protocol #3, by contracting and relaxing finger extensor muscles, while the lumbrical and interossei muscles were stimulated continuously, one could flex fingers from fully extended and fanned fingers into "L" shape postured fingers. During this therapy finger extensors could be stimulated using: a) either single electrode pair 40, 42, 44, 46 as shown in FIG. 4 and discussed in Protocol 1; or b) the more specific finger extension protocol discussed in Protocol 2 using a combination of electrodes 40, 50, 52, and 54 as shown in FIG. 5:

For this exercise, the order of stimulation was as follows:
1) Stimulation of the finger extensor muscles through a train of electric pulses, of an amplitude of 20 mA for the single electrode pair approach in a) or 15 mA for the multiple electrode approach in b), duration was 250 microseconds and frequency was 40 Hz. The train of pulses would gradually increase from pulse amplitude 0 mA to desired level within about 2 seconds, will remain at the desired level.
2) After the finger extensors are fully contracted (about 2 seconds after the stimulation has been initiated in extensors muscles) the stimulation of lumbrical and interossei muscles was initiated through a train of electric pulses, of an amplitude of 10 mA, a duration of 250 microseconds and a frequency of 40 Hz. The train of pulses was gradually increased from a pulse amplitude of 0 mA to 10 mA within about 2 seconds, and then held at the 10 mA level.
3) Once both finger extensors, and lumbrical and interossei muscles were all contracted, the stimulation intensity was held constant for about 30 seconds.
4) Following step 3, the stimulation of the finger extensors was dropped from the desired amplitude (20 or 15 mA) to 0 mA within about 2 sec. This will cause the fingers to go from full extension and fanning into "L" shaped flexion. Zero finger extensors' stimulation was maintained for 5-10 sec and finger extensors were again activated as in step (1) to generate finger extension and fanning that lasted about 30 seconds (see FIG. 2).
5) Steps (3) and (4) were repeated while the lumbrical and interossei muscles were continuously contracted, providing proper and repetitive finger extension (30 sec) and partial finger flexion (5-10 sec). This was repeated 5-20 times;
6) All finger extensors and the lumbrical and interossei muscles were relaxed and allowed to rest for couple of minutes.

The pulse amplitude for lumbrical and interossei muscles was finely adjusted, between 5 and 12 mA, until an appropriate amount of movement was seen in the muscles, providing an "L" shape to the hand when stimulated. The pulse amplitude for finger extensors was finely adjusted, between 15 and 25 mA, until an appropriate finger extension and fanning was achieved when lumbrical and interossei muscles were stimulated at the same time as the finger extensor muscles.

As indicated earlier, repetitive bursts of short finger flexion coupled with long bursts of finger extension enable additional reduction in finger and hand tone and later facilitate voluntary hand opening and closing in targeted patient populations.

Protocol 4—Lumbricalis-Finger Extension—Finger Flexion Protocol

In patients where the Lumbricalis-Finger Extension Protocol outcomes began to plateau, patients were moved to a fourth therapy, by combining the protocol used above with stimulation and relaxation of the finger flexor muscles.

As discussed above, combining the Lumbricalis-Finger Extension protocol with activation of finger flexor muscle groups provided a surprising incremental benefit in outcomes of treatment. In this fourth therapy, by contracting and relaxing finger extensor muscles, while the lumbrical and interossei muscles were stimulated continuously, one could flex fingers from fully extended and fanned fingers into "L" shape postured fingers. During this therapy finger extensors can be stimulated using: a) either single electrode pair 40, 42, 44, 46 shown in FIG. 4 and discussed in Protocol 1; or b) a more specific finger extension protocol as discussed in Protocol 2 using combination of electrodes 40, 50, 52, and 54 as shown in FIG. 5. Further more, when the finger extensors were relaxed the finger flexors could be contracted to generate an even better and stronger finger flexion as compared to Protocol 3. For this protocol, the order of stimulation was as follows:

1) Stimulation of the finger extensor muscles through a train of electric pulses, having an amplitude of 20 mA for the single electrode pair approach in a) or 15 mA for the multiple electrode approach in b), a duration of 250 microseconds and a frequency of 40 Hz. The train of pulses were gradually increased from a pulse amplitude of 0 mA to the desired level within about 2 seconds, and were held at the desired level.
2) After the finger extensors were fully contracted (about 2 seconds after the stimulation had been initiated in the extensors muscles) the stimulation of lumbrical and interossei muscles was initiated through a train of electric pulses, having an amplitude of 10 mA, a duration of 250 microseconds and a frequency of 40 Hz. The train of pulses was gradually increased from a pulse amplitude of 0 mA to 10 mA within about 2 sec, then held at the 10 mA level.
3) Once both finger extensors, and lumbrical and interossei muscles were all contracted the stimulation intensity was held constant for about 30 sec.
4) Following that the stimulation of the finger extensors was reduced from the desired amplitude (20 or 15 mA) to 0 mA within about 2 sec. This caused the fingers to go from full extension and fanning into "L" shaped flexion.
5) In combination with the finger extensors relaxation, we have produced finger flexion where the pulse amplitude is 25 mA, duration is 250 microseconds and frequency is 40 Hz. As the finger extensors went from the desired stimulation to 0 mA in 2 sec during that time the finger flexors went from 0 to 25 mA. The zero finger extensors' stimulation and 25 mA finger flexion stimulation was maintained for 5-10 sec. Following that the finger extensors was again activated as in (1) to generate finger extension and fanning that lasted 30 sec (see FIG. 1), while the finger flexors were relaxed and remain relaxed as long as the extensors were contracted.
6) Steps (3) and (5) were repeated while the lumbrical and interossei muscles were continuously contracted, to give proper and repetitive finger extension (30 sec) and full finger flexion (5-10 sec). This was repeated 5-20 times;
7) All finger extensors and flexors, and the lumbrical and interossei muscles were all relaxed and allowed to rest for couple of minutes;

In subacute (≤6 months) stroke population, the Fugl Meyer Assessment method, a 66 point scale of upper limb mobility, was used to measure and quantify upper limb mobility. It was found that the group subjected to the Lumbricalis Protocols, as described above, had significantly better outcomes, as measured on this scale. Mean improvement in the non-FES group (control group) was 6 points and the mean improvement in the FES group (intervention group) was 27.2 points on the Fugl Meyer Assessment scale.

Similarly in subacute (≤6 months) incomplete spinal cord injury population Spinal Cord Independence Measure Self-care Subscore, a 20 point scale, was used to assess the upper limb function. It was found that the group subjected to the Lumbricalis Protocols, as described above, had significantly better outcomes, as measured on this scale. Mean improvement in the non-FES group (control group) was 3 points and the mean improvement in the FES group (intervention group) was 12 points on the Spinal Cord Independence Measure Self-care Subscore scale.

Similarly, in chronic (>6 months, up to 5 years) stroke population, the Fugl Meyer Assessment method, a 66 point scale of upper limb mobility, was used to measure and quantify upper limb mobility. It was found that the chronic stroke patients who were subjected to the Lumbricalis Protocols, as described above, have improve outcomes, as measured on this scale. Mean improvement in the chronic patients as compared to their baseline assessment was 9.86 points on the Fugl Meyer Assessment scale. Please note that in this study all chronic stroke patients received FES therapy and were used as their own controls.

Similarly in chronic (>6 months, up to 2-26 years) incomplete spinal cord injury population Spinal Cord Independence Measure Self-care Subscore, a 20 point scale, was used to assess the upper limb function. It was found that the group subjected to the Lumbricalis Protocols, as described above, had significantly better outcomes, as measured on this scale. Mean improvement in the non-FES group (control group) was 0.66 points and the mean improvement in the FES group (intervention group) was 2.2 points on the Spinal Cord Independence Measure Self-care Subscore scale.

Example 2

Programmed/Programmable FES Stimulator

In order to provide the FES Stimulation described in Example 1, it was desirable to have a single, multi-channel, pre-programmed FES stimulator capable of providing the stimulation needed to finger extensors, finger flexors, as well as lumbrical/interossei muscle groups. Accordingly, a variety of such devices were made, having at least three, but in certain exemplifications, as many as 12 channels. In one embodiment, for example, the device had 6 channels, connected to the following muscle groups by electrodes: (1) extensors digitorum (connected to electrode 46); (2) Lumbrical/interossei muscles (connected to electrodes 30, 32, 34, 36); (3) flexors digitorum. In a further embodiment, described in detail herein, the device had 9 channels, connected to the following muscle groups by electrodes: (1) Branch 1 of the extensor digitorum (connected to electrode 50); (2) Branch 2 of the extensor digitorum (connected to electrode 52); (3) branch 1 of the extensor digitorum minimi (connected to electrode 54); (4) branch 1 of the lumbricalis muscles (connected to electrode 30); (5) branch 2 of the lumbricalis muscles (connected to electrode 32); (6) branch 3 of the lumbricalis muscles (connected to electrode 34); (7) branch 4 of the lumbricalis muscles (connected to electrode 36); (8) branch 1 of the flexor muscles; (9) branch 2 of the flexor muscles. This latter, more complex apparatus allows for the targeting of individual muscles, as required, enabling programming of the device for a variety of different muscle exercises, including various grasp exercises, for example, utilizing one or two fingers and thumb.

The device was pre-programmed to provide the stimulation protocols described above, allowing for user-provided input on amplitude of signal, but otherwise following the timing and frequency as described in Example 1. Once programmed and operational, the protocol (for example, protocols 1-4, described above) could be selected by a user, and the amplitude of the signal input. The device would automatically cycle through the protocol selected, providing a consistent exercise regime.

In one modification of the device, the device could communicate with a patient input means, such as a card containing an RFID chip, or a USB fob, identifying the patient. Thus the patient could have a personalized routine set up for them, and programmed onto the card or fob, which communicated with the device to select the desired protocol. It would be understood that the device could be supplied with a variety of such patient input means, each having a protocol or series of protocols pre-programmed, or each being blank, to be programmed by the user.

Example 3

Further Protocols

The programmable FES stimulator of Example 2 was used to develop 24 further protocols for stimulation of various muscle activities, for example, reaching, gripping, or grasping. Each protocol worked in a similar manner: electrodes were connected to the stimulator in a defined manner, with each electrode or electrode set being assigned a "channel". The protocols defined the order of activation and deactivation (i.e. increase and decrease in amplitude) of the channels. In certain embodiments, as described further below, protocols progressed from one activation/deactivation state to the next through operation of a button or switch by a user of the stimulator. For example, when the desired muscle movement was observed, and it was time to progress to the next step of the protocol, a user would press a button which would signal protocol progression. It would be appreciated, however, that this could be automated; for example, for a specific patient, the timing for protocol progression could be programmed, or "learned" over time by the programmable stimulator, and a timed, automated protocol progression could be utilized.

For each of the 24 further protocols, the method was similar:
 (a) The specific protocol was selected;
 (b) The electrodes were placed in the defined positions on the muscles to be activated;
 (c) The first step of the protocol was 'run', by pressing a button;
 (d) After desired muscle response was achieved, the protocol was progressed to the next step in the stimulation of the muscle groups, by pressing a button.
 (e) Once all of the steps of the protocol were performed, the protocol was repeated the desired amount of times as specified.

Protocol 1—Sideways Reaching

Figure 6:
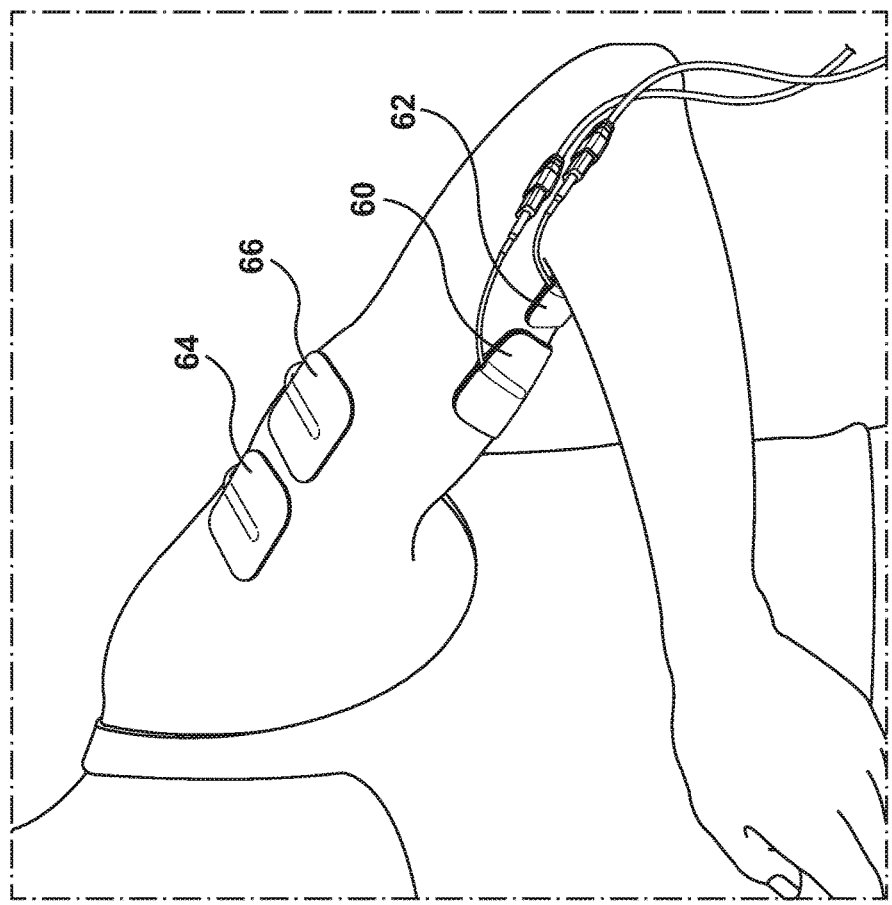
FIGS. 6,7,9,11,12,17,18,21,24,25,27-29,32,33,35,36,39-41,46-49,52-54,57,58,59, and 61 show photographic representations of electrode placement for activation of various muscles for use in various protocols of the invention.
Figure 7:
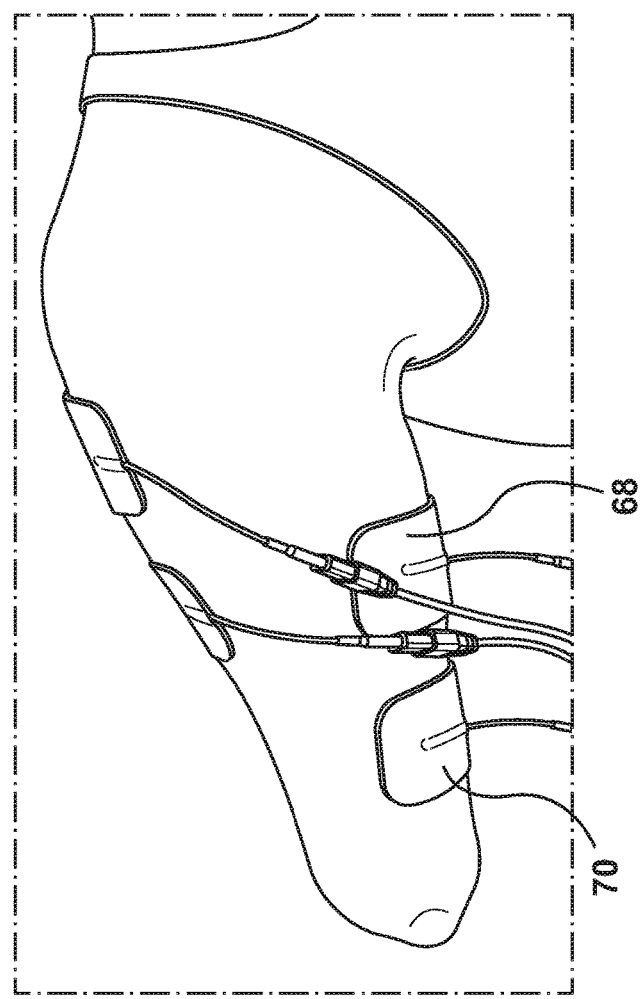
Figure 8:
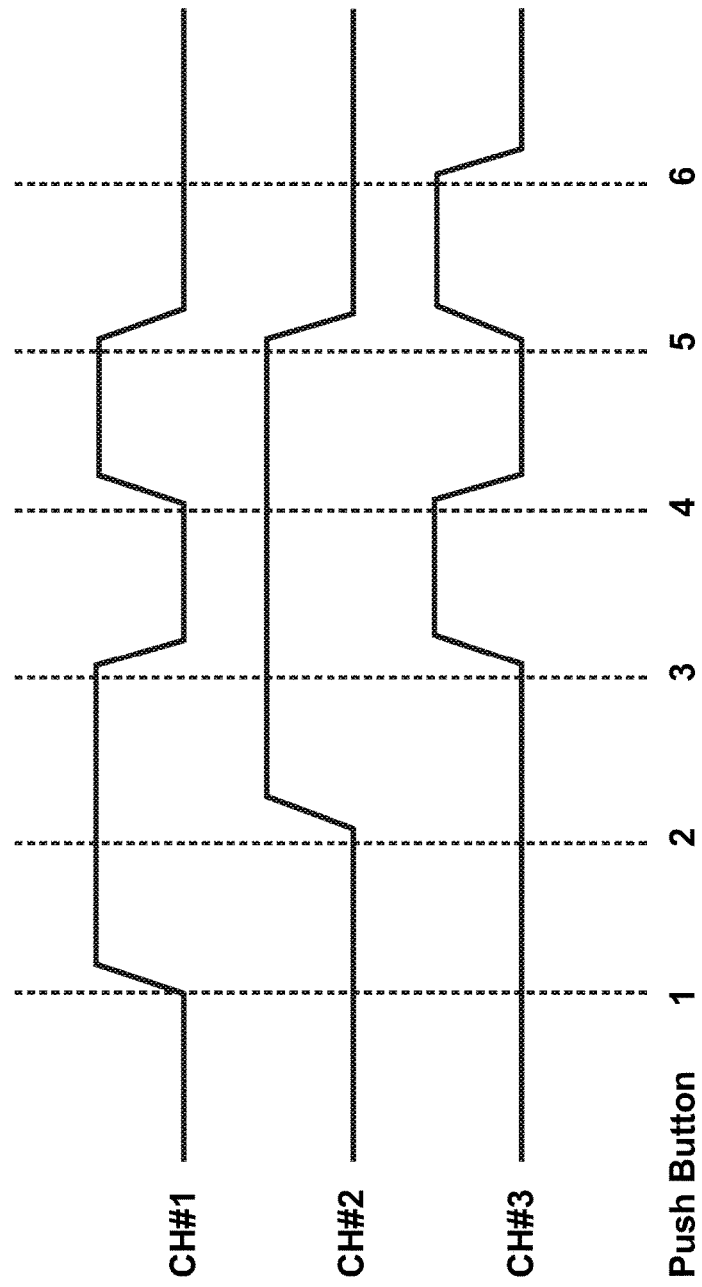

The "sideways reaching" protocol provided training for reaching sideways and retrieving tasks, for breaking the flexor synergy, and for preparation of training object reaching and transport. FIGS. 6 and 7 show the electrode placement for this protocol. FIG. 6 shows biceps cathode electrode (delivery electrode) 60 and biceps anode electrode (return electrode) 62 (Channel 1); middle deltoid muscle cathode electrode (delivery electrode) 64 and middle deltoid anode electrode (return electrode) 66 (Channel 2). FIG. 7 shows triceps cathode electrode 68 and anode electrode 70 (Channel 3). FIG. 8 is a schematic of the activation and deactivation of the three channels as the protocol progression is activated, through the use of a push button, with the schematic showing signal amplitude for the three channels (CH#1, CH#2, CH#3) over time. The horizontal lines depict that, until protocol progression is activated, the amplitude will remain at the indicated level.

Parameters and protocol progression were as follows:
Parameters:
 Pulse Duration: 400 μsec
 Max Amplitude: 30 mA (the amplitude range can be much smaller pending which stimulator is used)
 Ramp time: Ramp up 1 sec and ramp down 0.5 sec
 Pulse frequency: 40 Hz
 Channels used: Channels 1-3

As described above with respect to electrode placement, Channel 1 stimulates elbow flexors, i.e. biceps, channel 2 stimulates shoulder abductors, i.e. middle deltoids (elevating the arm sideways in a short lever position), and channel 3 stimulates elbow extensors, i.e. triceps, for allowing a complete sideway reach in the long lever position.

After electrodes were placed, the protocol was activated, through the use of a push button connected to the device. This resulted in protocol progression as depicted in FIG. 8. Specifically, at the first push, channel 1 amplitude was increased, until elbow flexion was achieved. The button was pushed again, resulting in protocol progression. In step 2 of the protocol, channel 1 remained active and channel 2 was activated. This resulted in elbow flexed followed by shoulder abduction. Once shoulder abduction was achieved, the button was pushed again, resulting in protocol progression to step 3 as shown in FIG. 8; channel 1 amplitude was reduced and, simultaneously, channel 3 amplitude was increased, with channel 2 amplitude remaining constant. This resulted in shoulder remaining in abduction while the elbow went into extension. Once elbow extension was satisfactory, the button was pushed again, resulting in protocol progression to step 4; channel 3 amplitude was reduced and the elbow flexed. Protocol progression to step 5 resulted in channels 1 and 2 decreasing in amplitude, and channel 3 amplitude again increasing, resulting in shoulder abduction (relaxation) and extension of the elbow. With a subsequent push of the button, channel 3 amplitude was reduced, and the arm completely relaxed.

The result of this protocol progression was a movement as follows: elbow flexion, followed by shoulder abduction, followed by elbow extension with shoulder in abduction, followed by elbow flexion, followed by shoulder adduction to neutral and elbow extension, then arm in neutral and relaxed position.

Figure 9:
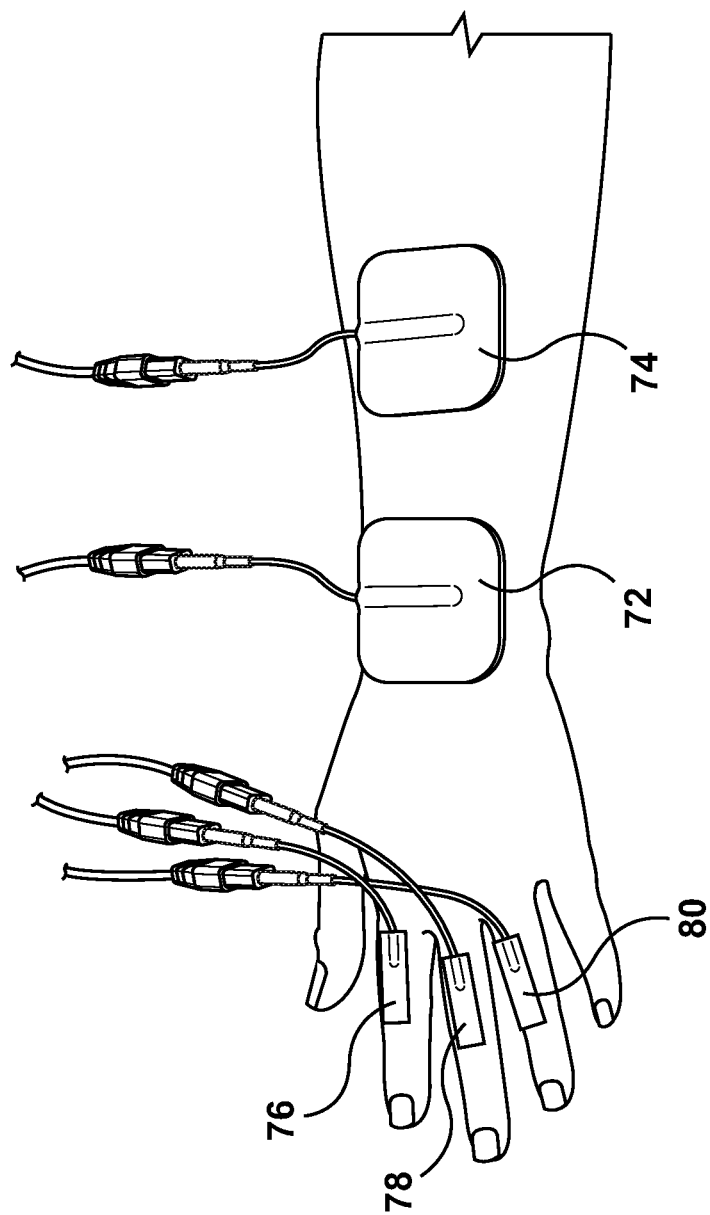

The protocol was repeated as necessary or desired.
Protocol 2—Sideways Reaching+Lumbrical and Extensor Communis Opening This protocol provided training for reaching sideways and retrieving tasks, for breaking the flexor synergy, and in preparation for training object reaching and transport. FIGS. 6, 7 and 9 show the electrode placement for this protocol. Electrode placement for channels 1, 2, and 3 were as described in Protocol 1, above. FIG. 9 shows placement of channels 4-7, as follows. Extensor digitorum communis, extensor carpi radialis, extensor carpi ulnaris 5×5 cm² cathode (delivery electrode) 72, and 5×5 cm² anode 74 (Channel 4); first, second and third lumbrical cathodes (76, 78 and 80, respectively) are also shown and represent channels 5, 6, and 7, respectively.

As shown all electrodes and cathodes are approximately 5×5 cm, with the exception of the lumbrical cathodes, which are 2×1 cm.

Figure 10:
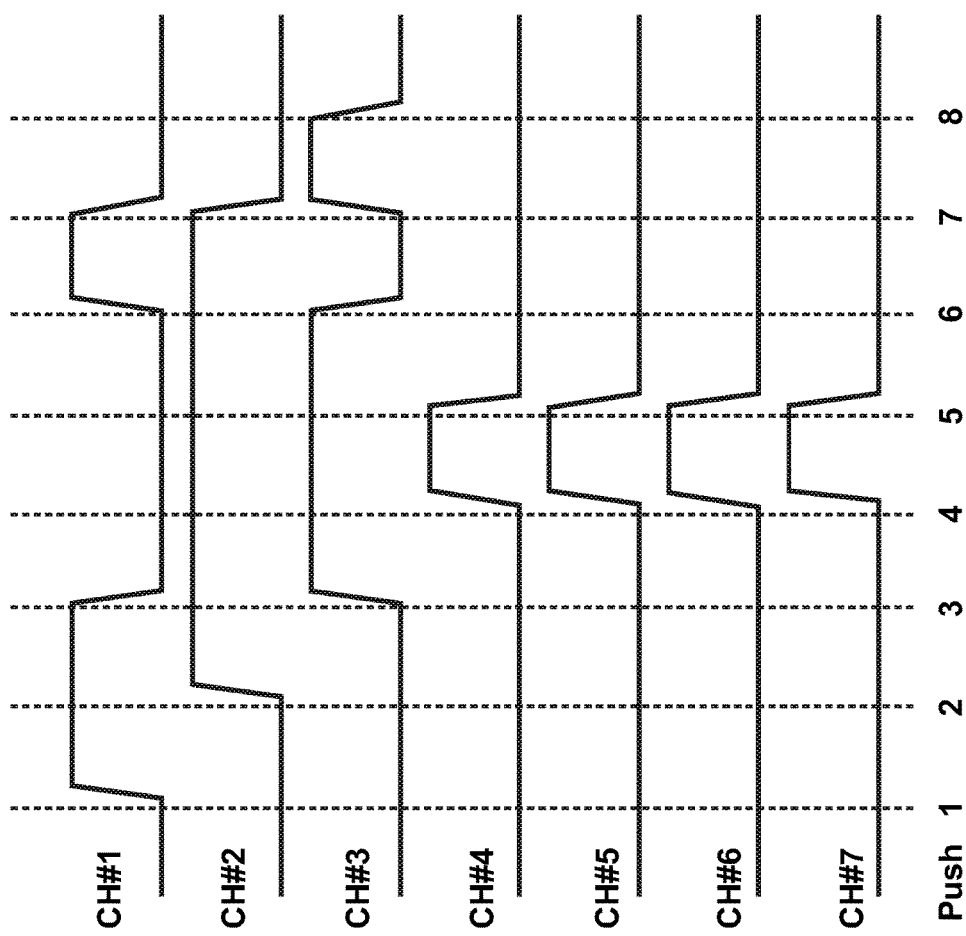

The protocol progression was shown, for the 8 steps of the protocol, in FIG. 10.

Parameters and protocol progression were as follows:
Parameters:
 Pulse Duration: 400 μsec
 Max Amplitude: 30 mA (the amplitude range can be much smaller pending which stimulator is used)
 Ramp time: Ramp up 1 sec and ramp down 0.5 sec
 Pulse frequency: 40 Hz Channels used: Channels 1-7
Placement of the Electrodes—Muscles that May be Stimulated:
  Channels 1-3 were used to stimulate proximal musculature of the arm and Channels 4-7 were used to stimulate wrist and finger muscles.
  Channel 1 stimulated elbow flexors, i.e. biceps [FIG. 6, electrodes 60 and 62]
  Channel 2 stimulated shoulder abductors, i.e. middle deltoid. This elevated the arm sideways in a short lever position [FIG. 6, electrodes 64 and 66]
  Channel 3 stimulated elbow extensors, i.e. triceps for allowing a complete sideway reach in the long lever position. [FIG. 7, electrodes 68 and 70]
  Channel 4 stimulated wrist and finger extensors, i.e. extensor Digitorum communis, extensor carpi radialis, extensor carpi ulnaris. [FIG. 9, electrodes 72 and 74]
  Channels 5-7 stimulated the lumbrical muscles to allow finger extension at the IP joints, i.e., lumbrical muscles (I, II, III), electrodes will be placed over dorsal aspect of the first phalanx of index, middle and ring finger. [FIG. 10, electrodes 76,78,80 and 74]
Typical electrode placement for Channels 1-3 and Channels 4-7 was shown in FIGS. 6, 7, and 9, as described above.
Program:
  Push button 1 (step 1): (a) Channel 1 was activated—Elbow flexion
  Push button 2 (step 2): (b) Channel 1 remained on and Channel 2 was activated—Elbow flexed followed by shoulder abduction
  Push button 3 (step 3): (c) Channel 1 was decreased and simultaneously Channel 3 was activated, while Channel 2 remained activated—Shoulder remained in abduction while elbow went into extension
  Push button 4 (step 4): (d) Channels 2 and 3 remained on and Channels 4-7 were activated—Shoulder and elbow remained in abduction and extension, respectively, while the wrist and finger extensors came up to generate wrist and finger extension.
  Push button 5 (step 5): (e) Channels 4-7 were decreased—Shoulder and elbow remain in abduction and extension, respectively, while the wrist and finger extensor muscles were relaxed.
  Push button 6 (step 6): (f) Channel 3 was decreased and Channel 1 was increased—Shoulder remained in abduction, and elbow flexed.
  Push button 7 (step 7): (g) Channels 1 and 2 decreased and Channel 3 was activated—Shoulder went into adduction (relaxed) and elbow extended.
  Push button 8 (step 8): (h) Channel 3 decreased—the arm completely relaxes.
  The protocol was repeated as necessary or desired.
  The subsequent push of the push button initiated the sequence as discussed at the beginning of the paragraph, i.e., it will start with Push button 1 (a).
Type of Movement Produced: (a) Elbow flexion (push button 1), (b) followed by shoulder abduction (push button 2), (c) followed by elbow extension with shoulder in abduction (push button 3); (d) followed by wrist and finger extension with the shoulder in abduction and elbow in extension (push button 4). The sequence of relaxation will be (e) release of wrist and finger extension (push button 5); (f) followed by elbow flexion (push button 6); (g) followed by shoulder adduction to neutral and elbow extension (push button 7); (h) followed by arm relaxed at the side of the body (push button 8).

Figure 11:
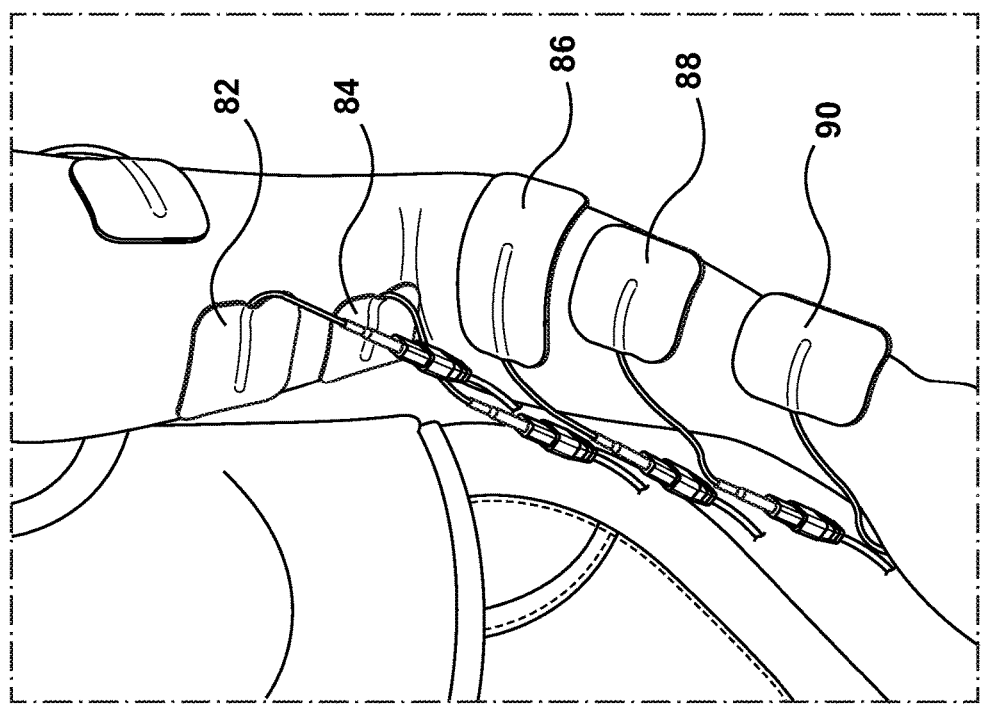
Figure 12:
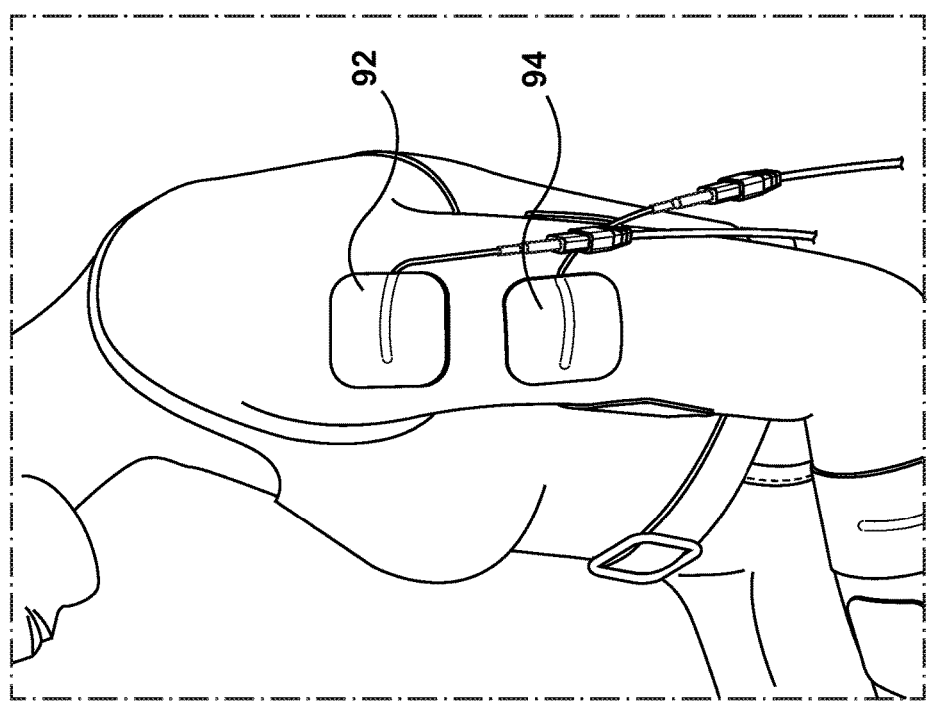
Figure 13:
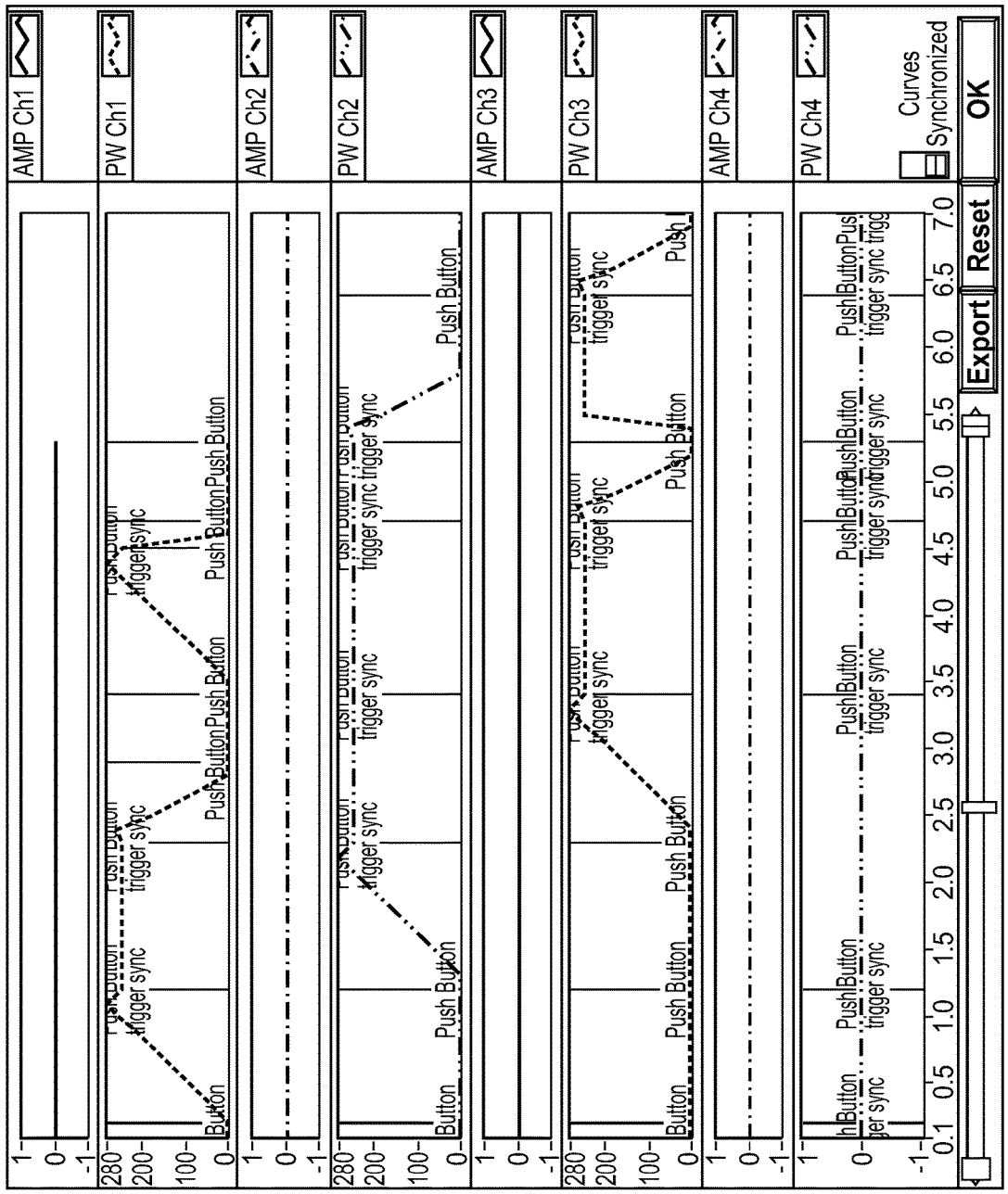
Figure 14:
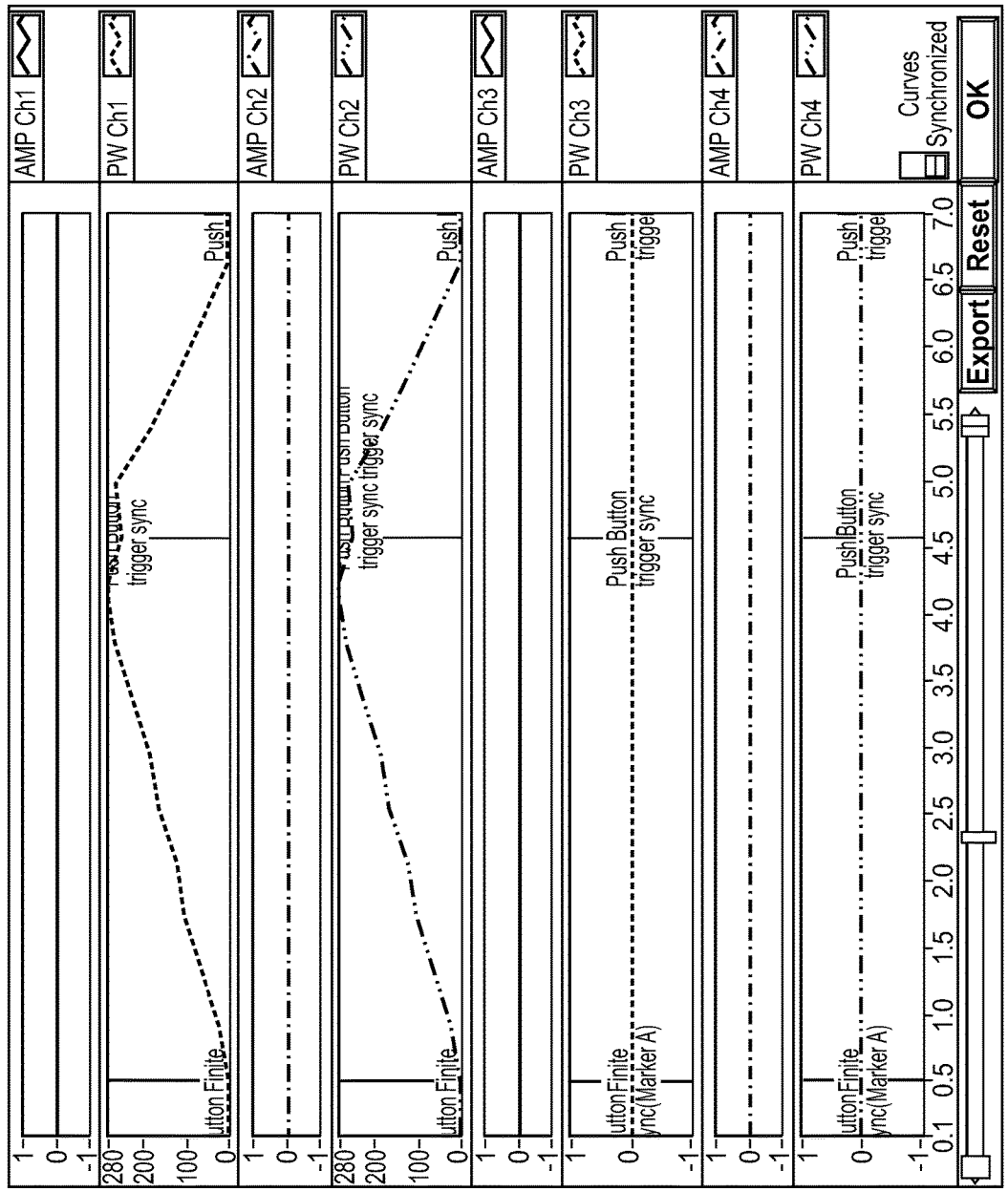
Figure 15:
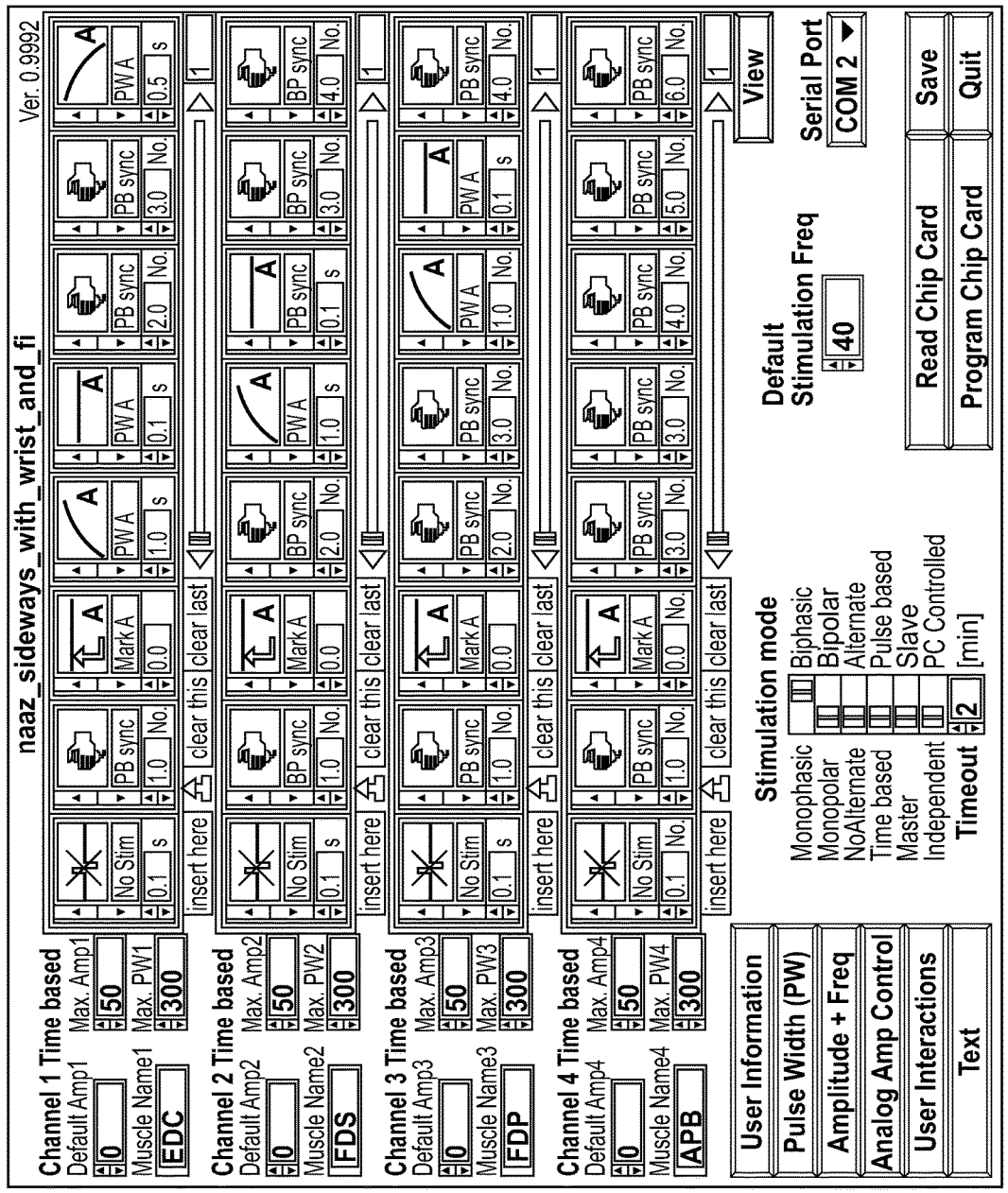
Figure 16:
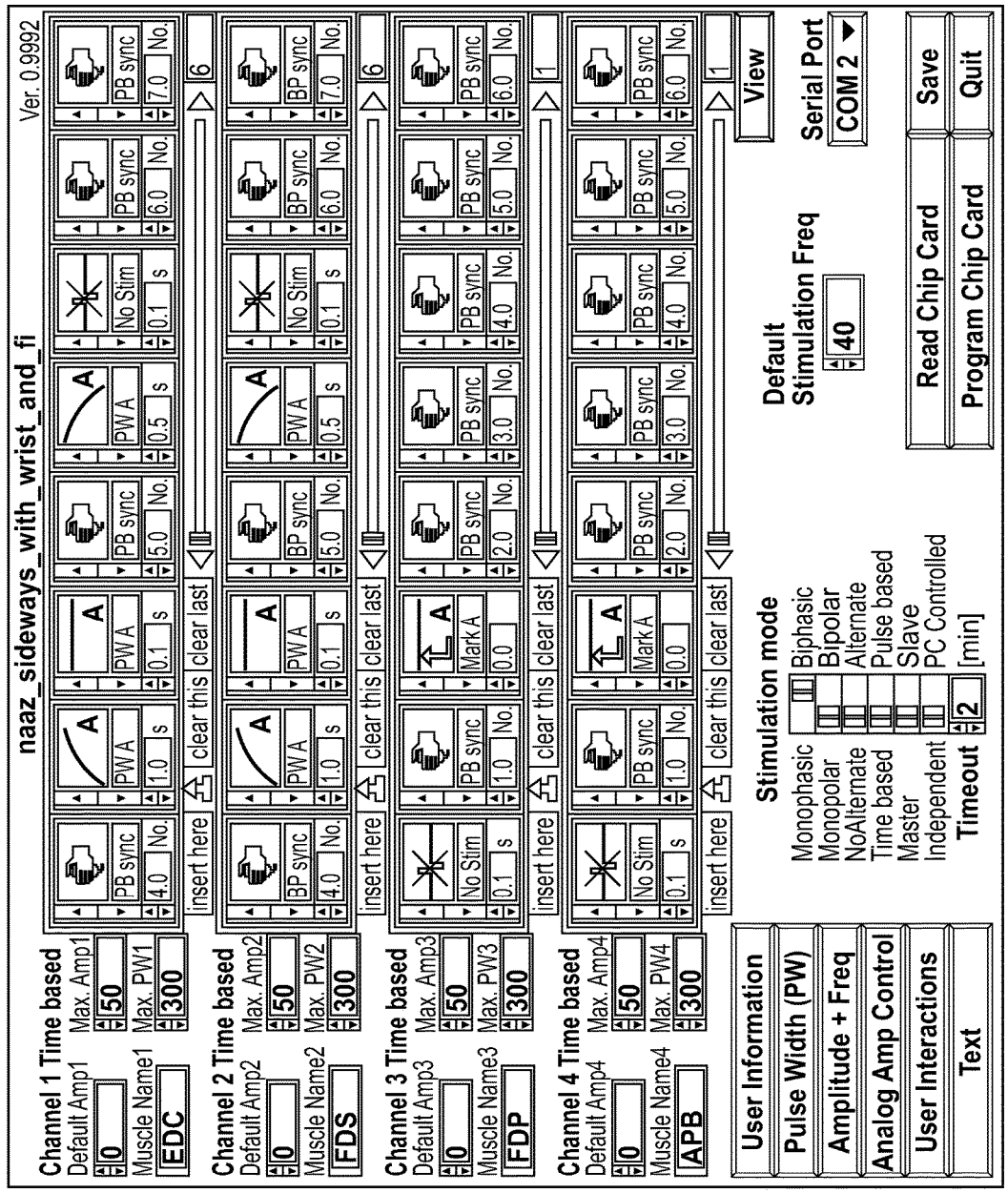

Protocol 3: Sideways Reaching and Extensor Communis Opening
This protocol provided training for reaching sideways and retrieving tasks, for breaking the flexor synergy, and for preparation for training object reaching and transport.
For this protocol, electrode placement for channel 3 was as described in protocol 1, above (FIG. 7). FIG. 11 shows placement of the electrodes for biceps, extensor carpi radialis, extensor carpi ulnaris and extensor Digitorum muscles. Electrode placement for channel 1 is shown as the 5×5 cm$^2$ cathode electrode (delivery electrode) for the biceps muscle 82, and 5×5 cm$^2$ anode electrode (i.e., return electrode) for biceps muscle 84. Also shown is 9×5 cm$^2$ cathode electrode (delivery electrode) for the extensor carpi radialis, extensor carpi ulnaris and extensor Digitorum 86 (Channel#5) and 5×5 cm$^2$ cathode electrode (delivery electrode) for the extensor Digitorum muscle (Channel #6), Also shown is the combined 5×5 cm$^2$ anode electrode for channels 5 and channel 6 90. FIG. 12 shows the electrode placement for the remaining channel—channel 2, as middle deltoid 5×5 cm$^2$ cathode 92 and middle deltoid 5×5 cm$^2$ anode 94.
As shown all electrodes and cathodes are 5×5 cm.
The protocol progression was shown, for the 8 steps of the protocol, in FIG. 13 (for channels 1-3) and FIG. 14 (for channels 5 and 6). Pulse amplitudes, pulse durations and ramp times for channels 1-3 and 5-6 are shown in FIGS. 15 and 16, respectively.
Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 1-3, 5 and 6
Placement of the Electrodes—Muscles that May be Stimulated:
  Channels 1-3 were used to stimulate proximal musculature of the arm and Channels 5-6 were used to stimulate wrist and finger muscles.
  Channel 1 was used to stimulate elbow flexors, i.e. biceps
  Channel 2 was used to stimulate shoulder abductors, i.e. middle deltoid. This resulted in elevating the arm sideways in a short lever position
  Channel 3 was used to stimulate elbow extensors, i.e. triceps for allowing a complete sideway reach in the long lever position.
  Channel 5 was used to stimulate wrist extensors, i.e. extensor digitorum, extensors carpi radialis, extensor carpi ulnaris.
  Channel 6 was used to stimulate the extensor Digitorum to allow finger extension at the MCP and IP joints of the fingers.
  Electrode placement for Channels 1-3 and Channels 5-6 were shown in FIGS. 7, 11 and 12 as described above.
Program:
  Push button 1: (a) Channel 1 was activated—Elbow flexion
  Push button 2: (b) Channel 1 remained on and Channel 2 was activated—Elbow flexed followed by shoulder abduction
  Push button 3: (c) Channel 1 was decreased and simultaneously Channel 3 was activated, while Channel 2 remained on—Shoulder remains in abduction while elbow goes into extension
  Push button 4: (d) Channels 2 and 3 remained on and Channels 5 and 6 were activated, —Shoulder and elbow remain in abduction and extension, respectively, while the wrist and finger extensors came up to generate finger extension.

Push button 5: (e) Channels 5-6 were decreased—Shoulder and elbow remained in abduction and extension, respectively, while the wrist and finger extensor muscles were relaxed.

Push button 6: (f) Channel 3 was decreased and Channel 1 activated—Shoulder remained in abduction, and elbow flexed.

Push button 7: (g) Channels 1 and 2 were decreased and Channel 3 activated—Shoulder went into adduction (relaxes) and elbow extended.

Push button 8: (h) Channel 3 was decreased—the arm completely relaxes.

The protocol was repeated as necessary or desired.

The subsequent push of the push button will initiate the sequence as discussed at the beginning of the paragraph, i.e., it will start with Push button 1 (a).

Type of Movement Produced: (a) Elbow flexion (push button 1), (b) followed by shoulder abduction (push button 2), (c) followed by elbow extension with shoulder in abduction (push button 3); (d) followed by wrist and finger extension with the shoulder in abduction and elbow in extension (push button 4). The sequence of relaxation will be (e) release of wrist and finger extension (push button 5); (f) followed by elbow flexion (push button 6); (g) followed by shoulder adduction to neutral and elbow extension (push button 7); (h) arm relaxed by the side of the body (push button 8).

Protocol 4: Forward Reaching and Retrieving

This protocol provided training for breaking flexor synergy, for training the arm to place the hand in various locations in the working space, and for preparation for training object reaching and transport.

Figure 17:
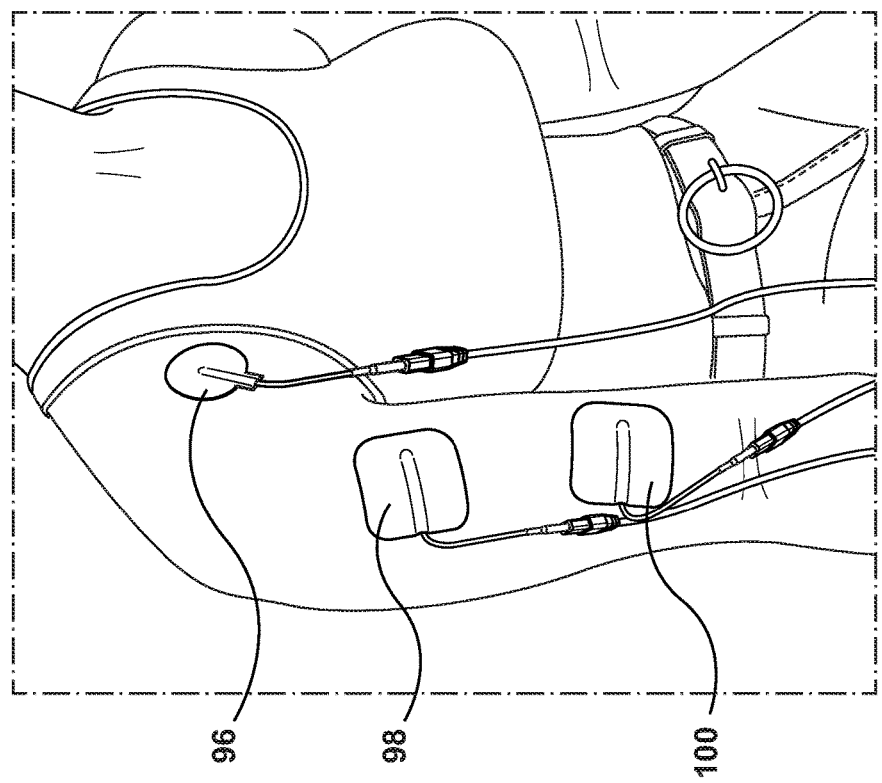

For this protocol, electrode placement for anterior deltoid muscle and for biceps is shown in FIG. 17. Shown is the 2.5 cm diameter cathode electrode (delivery electrode) for the anterior deltoid muscle 96 (Channel #1). Also shown is a 5×5 cm$^2$ dual-use electrode 98 which is utilized as the anode electrode (i.e., return electrode) for channel #1 and as cathode electrode for channel 3, which stimulates biceps muscle. Anode electrode for channel 3 is shown as 100.

Figure 18:
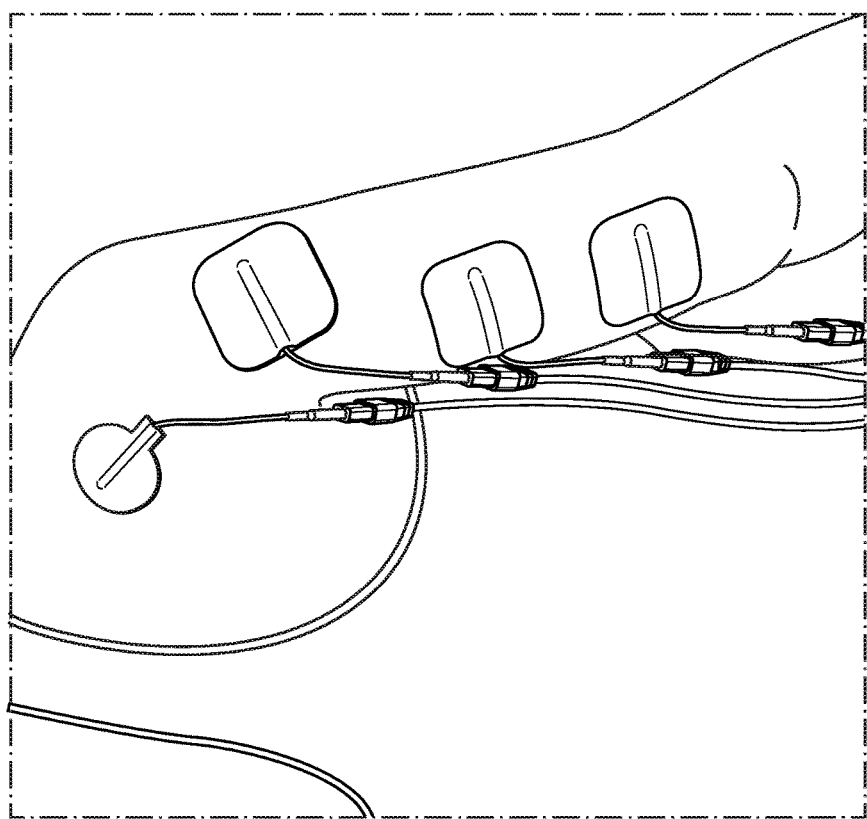

FIG. 18 shows placement of the electrodes for the posterior deltoid muscle and for triceps. 102 is the 2.5 cm diameter cathode electrode (delivery electrode) for the posterior deltoid muscle, (Channel #2). 104 is the 5×5 cm$^2$ anode electrode (i.e., return electrode) for channel #2, which stimulates posterior deltoid muscle. 106 is the 5×5 cm$^2$ cathode electrode for channel #4 that stimulates the triceps muscles. 108 is the 5×5 cm$^2$ anode (i.e., return electrode) electrode for Channel #4 that stimulates the triceps muscles.

Figure 19:
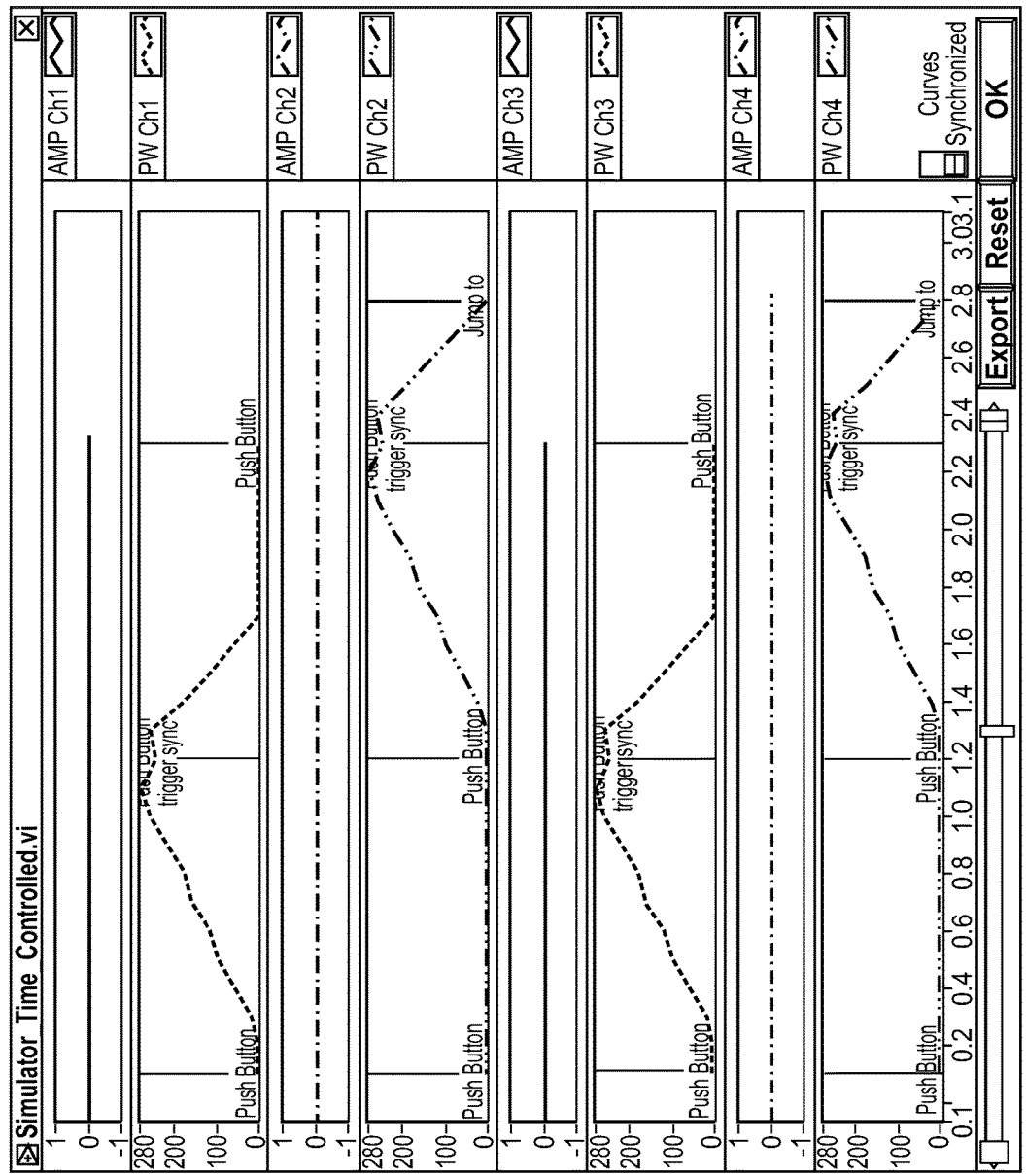
Figure 20:
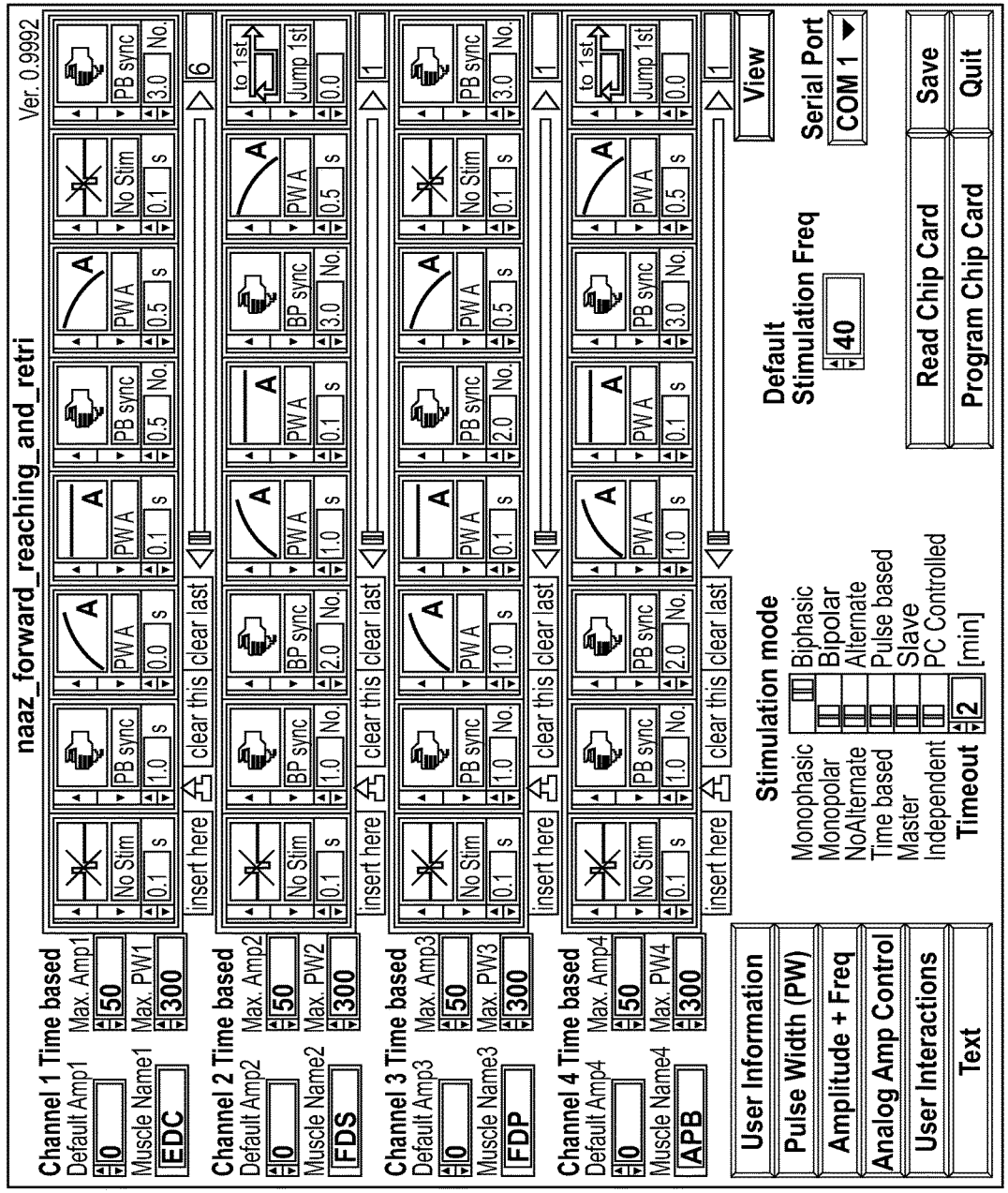

The protocol progression was shown, for the 3 steps of the protocol, in FIG. 19. Pulse amplitudes, pulse durations and ramp times are shown in FIG. 20.

Parameters and protocol progression were as follows:
Parameters:
Pulse Duration: 400 μsec
Max Amplitude: 30 mA (the amplitude range can be much smaller pending which stimulator is used)
Ramp time: Ramp up 1 sec and ramp down 0.5 sec
Pulse frequency: 40 Hz
Channels used: Channels 1-4

Placement of the Electrodes—Muscles that May be Stimulated:

Channels 1 and 3 were activated simultaneously and were used to produce forward reaching movement of the proximal upper extremity, i.e., flexion of shoulder and extension of the elbow respectively. Channels 2 and 4 were activated simultaneously and were used to produce a backward retrieving movement of the proximal upper extremity, i.e., extension of the shoulder and flexion of the elbow.

Channel 1 was used to stimulate shoulder flexor, i.e. anterior deltoid. This was used to make the shoulder flex and place the arm forward in front of the body.

Channel 2 was used to stimulate shoulder extensor, i.e., posterior deltoid. This was used to make the shoulder extend backwards.

Channel 3 was used to stimulate elbow extensor, i.e. triceps. This was used in combination with Channel 1 fully extend the arm in front of the subject.

Channel 4 was used to stimulate elbow flexor, i.e., biceps. This was used in combination with Channel 2 generate shoulder extension placing the arm in retrieval posture that looks like "holding a ski poll next to body."

Electrode placement for Channels 1-4 was shown in FIGS. 17 and 18 as described above.

Program:
Push button 1: (a) Channels 1 and 3 were activated simultaneously—Elbow extended and the shoulder flexed forward placing the arm in forward reaching position.

Push button 2: (b) Channels 1 and 3 were decreased and Channels 2 and 4 were activated simultaneously—Elbow flexed and the shoulder extended placing the arm in retrieval posture that looks like "holding a ski poll next to body."

Push button 3: (c) Channels 2 and 4 were decreased—that arm completely relaxes.

The protocol was repeated as necessary or desired.

The subsequent push of the push button will initiate the sequence as discussed at the beginning of the paragraph, i.e., it will start with Push button 1 (a).

Type of Movement Produced: Shoulder flexion and elbow extension followed by shoulder extension and elbow flexion followed by shoulder and elbow relaxed to neutral position.

Protocol 5: Forward Reaching and Retrieving and Lumbrical and Extensor Communis Opening This protocol provided training for breaking flexor synergy, for training the arm to place the hand in various locations in the working space, and in preparation for training object reaching and transport.

For this protocol, electrode placement for anterior deltoid muscle and for biceps is shown in FIG. 17. Shown is the 2.5 cm diameter cathode electrode (delivery electrode) for the anterior deltoid muscle 96 (Channel #1). Also shown is a 5×5 cm$^2$ dual-use electrode 98 which is utilized as the anode electrode (i.e., return electrode) for channel #1 and as cathode electrode for channel 4, which stimulates biceps muscle. 5×5 cm$^2$ anode electrode for channel 4 is shown as 100.

FIG. 18 shows placement of the electrodes for the posterior deltoid muscle and for triceps. 102 is the 2.5 cm diameter cathode electrode (delivery electrode) for the posterior deltoid muscle, (Channel #2). 104 is the 5×5 cm$^2$ anode electrode (i.e., return electrode) for channel #2, which stimulates posterior deltoid muscle. 106 is the 5×5 cm$^2$ cathode electrode for channel #3 that stimulates the triceps muscles. 108 is the 5×5 cm$^2$ anode (i.e., return electrode) electrode for Channel #3 that stimulates the triceps muscles.

Figure 21:
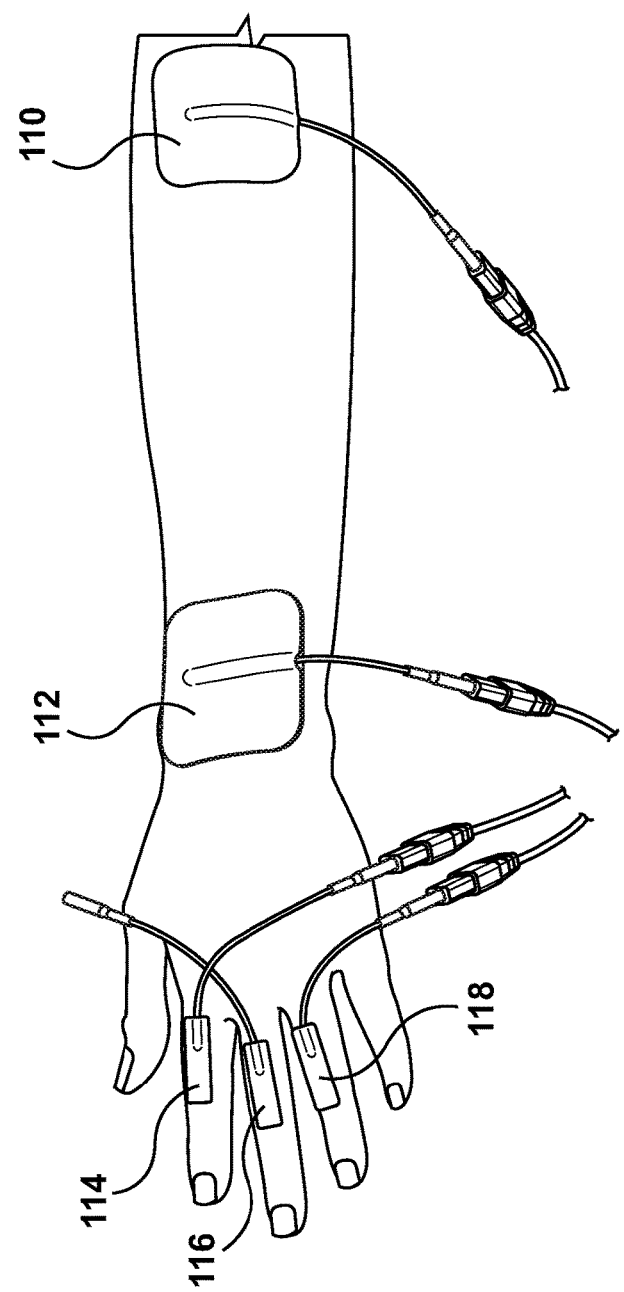

FIG. 21 shows placement of electrodes for the Extensor digitorum, Extensors carpi radialis, Extensor carpi ulnaris and for Lumbrical muscles. 110 shows 5×5 cm$^2$ cathode electrode (delivery electrode) for the Extensor digitorum, Extensors carpi radialis, Extensor carpi ulnaris i.e., Channel #5 cathode. 112 is the 5×5 cm² anode electrode (i.e., return electrode) for channels 5, 6, 7 and 8. Electrodes 114, 116 and 118 are the cathode electrode (delivery electrode) for channels 6, 7 and 8, respectively, that stimulates the Lumbrical muscles. Electrode size is 1.5 cm×2 cm.

Figure 22:
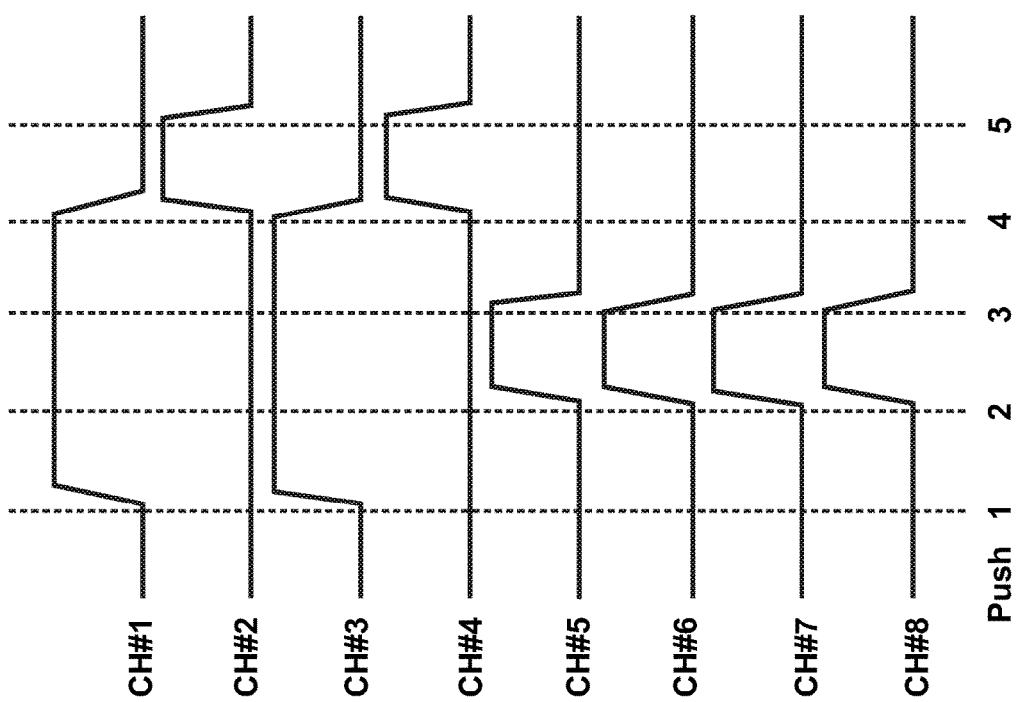

The protocol progression was shown, for the 5 steps of the protocol, in FIG. 22.

Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 1-8
Placement of the Electrodes—Muscles that May be Stimulated:

Channels 1 and 3 were activated simultaneously and were used to produce forward reaching movement of the proximal upper extremity, i.e., flexion of shoulder and extension of the elbow respectively. Channels 2 and 4 were activated simultaneously and were used to produce a backward retrieving movement of the proximal upper extremity, i.e., extension of the shoulder and flexion of the elbow. Channel 5-8 were used to activate wrist and finger extensors to produce hand opening while the shoulder is in forward flexion and elbow in extension.

Channel 1 was used to stimulate shoulder flexor, i.e. anterior deltoid. This was used to make the shoulder flex and place the arm forward in front of the body.
  Channel 2 was used to stimulate shoulder extensor, i.e., posterior deltoid. This was used to make the shoulder extend backwards.
  Channel 3 was used to stimulate elbow extensor, i.e. triceps. This was used in combination with Channel 1 fully extend the arm in front of the subject.
  Channel 4 was used to stimulate elbow flexor, i.e., biceps. This was used in combination with Channel 2 generate shoulder extension placing the arm in retrieval posture that looks like "holding a ski poll next to body."
  Channel 5 was used to stimulate wrist and finger extensors, i.e. extensor digitorum, extensor carpi radialis, extensor carpi ulnaris.
  Channels 6-8 was used to stimulate the lumbrical muscles to allow finger extension at the IP joints, i.e., lumbrical muscles (I, II, III, and IV), electrodes were placed over dorsal aspect of the first phalanx of index, middle and ring finger. Note: Channels 6-8 are activate with 100-500 milliseconds after the Channel 5 was activated.
Electrode placement for Channels 1-8 was shown in FIGS. 17, 18 and 21 as described above.
Program:
  Push button 1: (a) Channels 1 and 3 were activated simultaneously—Elbow extended and the shoulder flexed forward placing the arm in forward reaching position.
  Push button 2: (b) Channels 1 and 3 were kept activated and channels 5-8 were activated to produce wrist and finger extension so that the arm is in forward flexion with elbow, wrist and finger in extension. Note: Channel 5 was activated first and following 100-500 milliseconds delay Channels 6-8 have been activated.
  Push Button 3: (c) Channels 5-8 were decreased so that the arm was in forward flexion and elbow in extension and the wrist and the fingers relaxed.
  Push button 4: (d) Channels 1 and 3 were decreased and Channels 2 and 4 were activated—resulting in elbow flex and the shoulder extension placing the arm in retrieval posture that looked like "holding a ski poll next to body."
  Push button 5: (e) Channels 2 and 4 were decreased—the arm completely relaxes.

The protocol was repeated as necessary or desired.

The subsequent push of the push button will initiate the sequence as discussed at the beginning of the paragraph, i.e., it will start with Push button 1 (a).

Type of Movement Produced: Shoulder flexion and elbow extension followed by wrist and finger extension followed by wrist and finger relaxation followed by shoulder extension and elbow flexion followed by shoulder and elbow relaxed to neutral position.

Protocol 6—Forward Reaching and Retrieving+Extensor Communis Opening

This protocol provided training for breaking the flexor synergy, for training the arm to place the hand in various locations in the working space, and for preparation for training object reaching and transport.

For this protocol, electrode placement for anterior deltoid muscle and for biceps is shown in FIG. 17. Shown is the 2.5 cm diameter cathode electrode (delivery electrode) for the anterior deltoid muscle 96 (Channel #1). Also shown is a 5×5 cm² dual-use electrode 98 which is utilized as the anode electrode (i.e., return electrode) for channel #1 and as cathode electrode for channel 4, which stimulates biceps muscle. 5×5 cm² anode electrode for channel 4 is shown as 100.

FIG. 18 shows placement of the electrodes for the posterior deltoid muscle and for triceps. 102 is the 2.5 cm diameter cathode electrode (delivery electrode) for the posterior deltoid muscle, (Channel #2). 104 is the 5×5 cm² anode electrode (i.e., return electrode) for channel #2, which stimulates posterior deltoid muscle. 106 is the 5×5 cm cathode electrode for channel #3 that stimulates the triceps muscles. 108 is the 5×5 cm² anode (i.e., return electrode) electrode for Channel #3 that stimulates the triceps muscles.

FIG. 11 shows placement of the electrodes for extensor carpi radialis, extensor carpi ulnaris and extensor Digitorum muscles. Electrode placement for channel 5 is shown as 9×5 cm² cathode electrode (delivery electrode) for the extensor carpi radialis, extensor carpi ulnaris and extensor Digitorum 86 (Channel#5) and 5×5 cm² cathode electrode (delivery electrode) for the extensor Digitorum muscle 88 (Channel #6), Also shown is the combined 5×5 cm² anode electrode for channels 5 and channel 6 90. In this protocol, electrodes 82 and 84 are not utilized.

Figure 23:
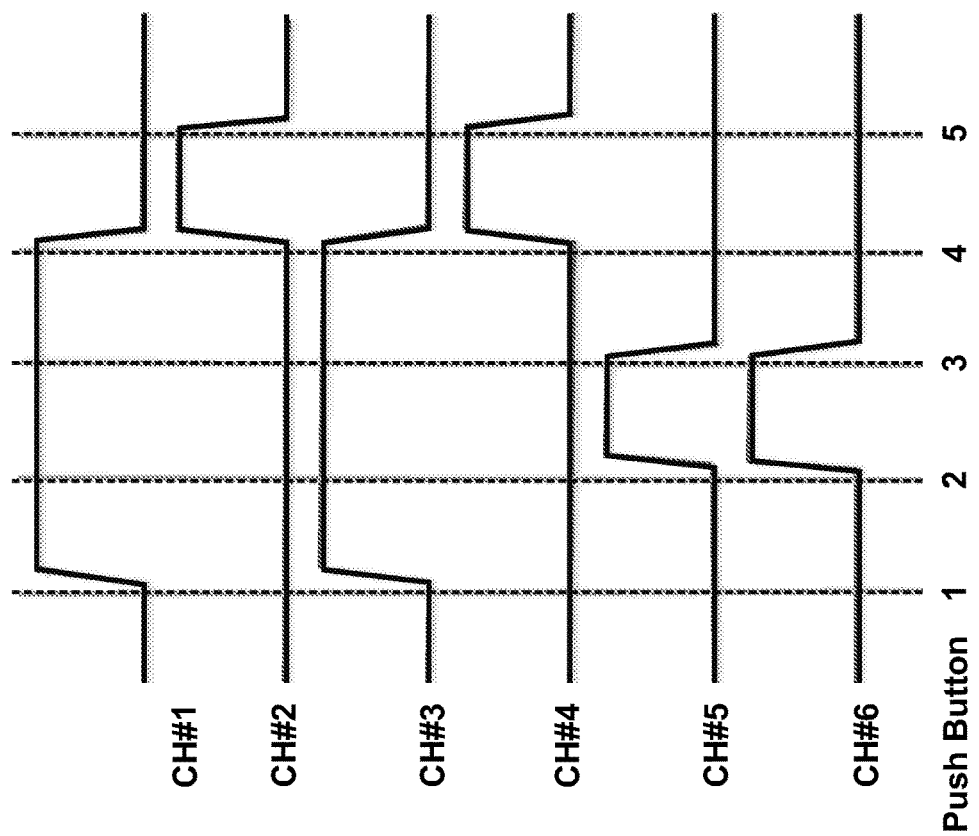

The protocol progression was shown, for the 5 steps of the protocol, in FIG. 23.

Parameters and protocol progression was as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 1-6
Placement of the Electrodes—Muscles that May be Stimulated:

Channels 1 and 3 were activated simultaneously and were used to produce forward reaching movement of the proximal upper extremity, i.e., flexion of shoulder and extension of the elbow respectively. Channels 2 and 4 were activated simultaneously and were used to produce a backward retrieving movement of the proximal upper extremity, i.e., extension of the shoulder and flexion of the elbow. Channel 5-6 were used to activate wrist and finger extensors to produce hand opening while the shoulder is in forward flexion and elbow in extension.

Channel 1 was used to stimulate shoulder flexor, i.e. anterior deltoid. This will make the shoulder flex and place the arm forward in front of the body.

Channel 2 was used to stimulate shoulder extensor, i.e., posterior deltoid. This will make the shoulder extend backwards.

Channel 3 was used to stimulate elbow extensor, i.e. triceps. This, in combination with Channel 1, caused the arm to fully extend in front of the subject.

Channel 4 was used to stimulate elbow flexor, i.e., biceps. This will in combination with Channel 2 generated shoulder extension placing the arm in retrieval posture that looks like "holding a ski poll next to body."

Channel 5 was used to stimulate wrist extensors, i.e. extensor digitorum, extensors carpi radialis, extensor carpi ulnaris.

Channel 6 was used to stimulate extensor digitorum to allow finger extension at the MCP and IP joints of the fingers.

Electrode placement for Channels 1-6 was shown in FIGS. 11, 17 and 18 as described above.

Program:
Push button 1: (a) Channels 1 and 3 were activated simultaneously—Elbow will extend and the shoulder will flex forward placing the arm in forward reaching position.
Push button 2: (b) Channels 1 and 3 remained on and channels 5-6 were activated to produce wrist and finger extension so that the arm is in forward flexion with elbow, wrist and finger in extension.
Push Button 3: (c) Channels 5-6 were decreased so that the arm is in forward flexion and elbow in extension and the wrist and the fingers relax.
Push button 4: (d) Channels 1 and 3 were decreased and Channels 2 and 4 were activated simultaneously—Elbow will flex and the shoulder will extend placing the arm in retrieval posture that looks like "holding a ski poll next to body."
Push button 5: (e) Channels 2 and 4 were decreased—the arm completely relaxes.

The protocol was repeated as necessary or desired.

The subsequent push of the push button will initiate the sequence as discussed at the beginning of the paragraph, i.e., it will start with Push button 1 (a).

Type of Movement Produced: Shoulder flexion and elbow extension followed by wrist and finger extension followed by wrist and finger relaxation followed by shoulder extension and elbow flexion followed by shoulder and elbow relaxed to neutral position.

Protocol 7—Forward Reaching and Retrieving+Extensor Communis Opening and Grasping This protocol provided training for breaking the flexor synergy, for training the arm to place the hand in various locations in the working space, and for preparation for training object reaching and transport.

For this protocol, electrode placement for anterior deltoid muscle and for biceps is shown in FIG. 17. Shown is the 2.5 cm diameter cathode electrode (delivery electrode) for the anterior deltoid muscle 96 (Channel #1). Also shown is a 5×5 cm² dual-use electrode 98 which is utilized as the anode electrode (i.e., return electrode) for channel #1 and as cathode electrode for channel 4, which stimulates biceps muscle. 5×5 cm² anode electrode for channel 4 is shown as 100.

FIG. 18 shows placement of the electrodes for the posterior deltoid muscle and for triceps. 102 is the 2.5 cm diameter cathode electrode (delivery electrode) for the posterior deltoid muscle, (Channel #2). 104 is the 5×5 cm² anode electrode (i.e., return electrode) for channel #2, which stimulates posterior deltoid muscle. 106 is the 5×5 cm² cathode electrode for channel #3 that stimulates the triceps muscles. 108 is the 5×5 cm² anode (i.e., return electrode) electrode for Channel #3 that stimulates the triceps muscles.

FIG. 11 shows placement of the electrodes for extensor carpi radialis, extensor carpi ulnaris and extensor Digitorum muscles. Electrode placement for channel 5 is shown as 9×5 cm² cathode electrode (delivery electrode) for the extensor carpi radialis, extensor carpi ulnaris and extensor Digitorum 86 (Channel#5) and 5×5 cm² cathode electrode (delivery electrode) for the extensor Digitorum muscle 88 (Channel #6), Also shown is the combined 5×5 cm² anode electrode for channels 5 and channel 6 90. In this protocol, electrodes 82 and 84 are not utilized.

Figure 24:
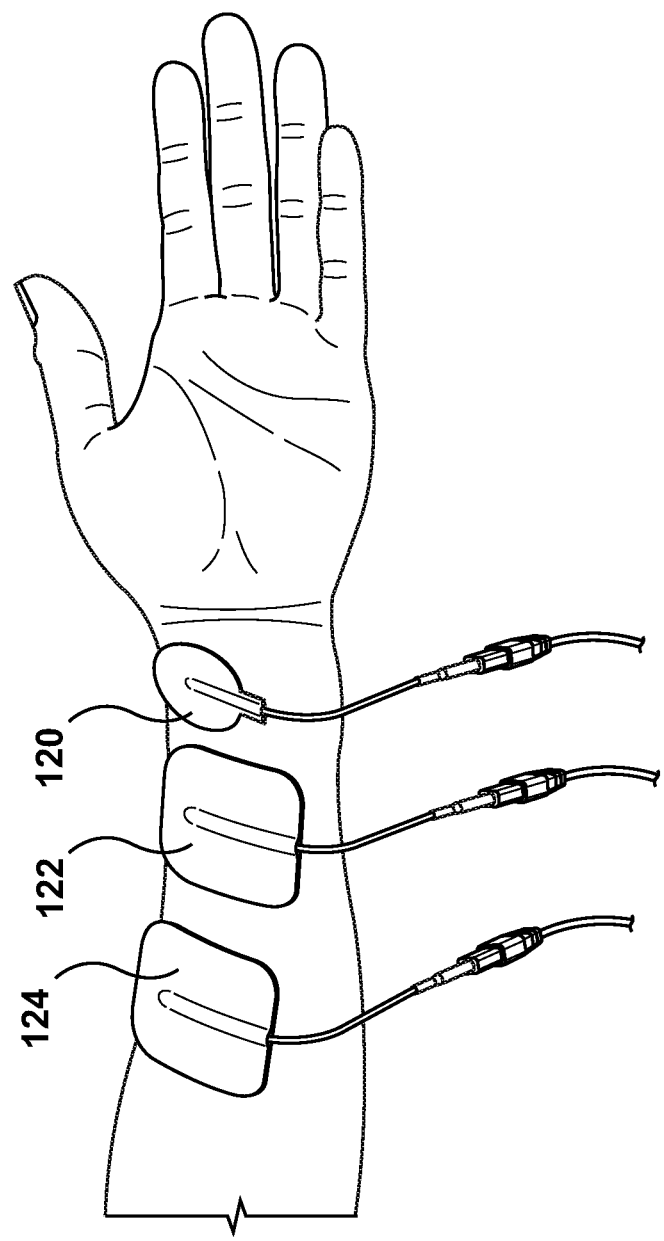
Figure 25:
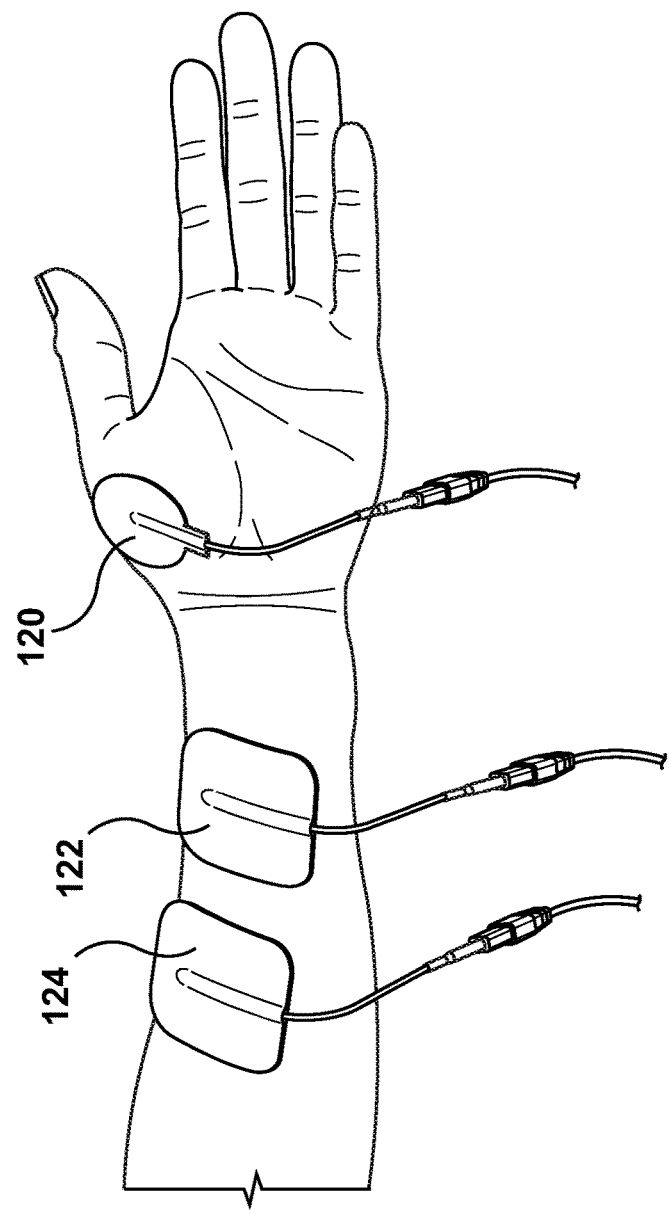

FIG. 24 shows Placement of electrodes for the Flexor Digitorum Superficialis and Profundus and Median nerve. 120 is the cathode electrode (delivery electrode) for Median nerve i.e., Channel #8 (CH#8) cathode. Size of the electrode 2.5 cm in diameter. 122 is the anode electrode (i.e., return electrode) for CH#7 and 8. Electrode size is 5×5 cm². 124 is the cathode electrode for CH#7 that stimulates Flexor Digitorum Superficialis and Profundus muscles. Electrode size is 5×5 cm². Alternate placement of electrodes 120, 122 and 124 is illustrated in FIG. 25.

Figure 26:
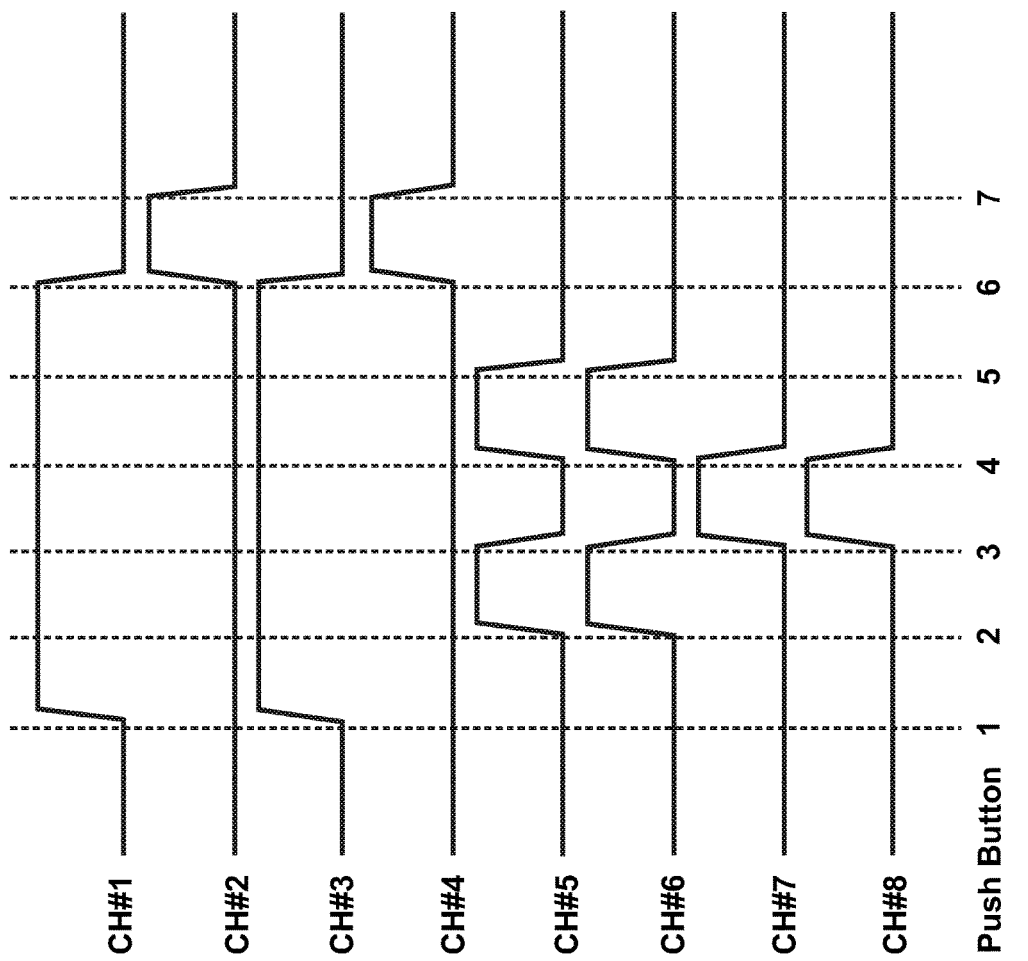

The protocol progression was shown, for the 5 steps of the protocol, in FIG. 26.

Parameters and protocol progression was as follows:
Parameters:
Pulse Duration: 400 μsec
Max Amplitude: 30 mA (the amplitude range can be much smaller pending which stimulator is used)
Ramp time: Ramp up 1 sec and ramp down 0.5 sec
Pulse frequency: 40 Hz
Channels used: Channels 1-8

Placement of the Electrodes—Muscles that May be Stimulated:

Channels 1 and 3 were activated simultaneously and were used to produce forward reaching movement of the proximal upper extremity, i.e., flexion of shoulder and extension of the elbow respectively. Channels 2 and 4 were activated simultaneously and were used to produce a backward retrieving movement of the proximal upper extremity, i.e., extension of the shoulder and flexion of the elbow. Channel 5-6 were used to activate wrist and finger extensors to produce hand opening while the shoulder is in forward flexion and elbow in extension. Channel 7 was used to activate finger flexors to produce hand closing and Channel 8 was used to stimulate the thumb oppositors to produce opposition of the thumb on the flexed fingers.

Channel 1 was used to stimulate shoulder flexor, i.e. anterior deltoid. This will make the shoulder flex and place the arm forward in front of the body.

Channel 2 was used to stimulate shoulder extensor, i.e., posterior deltoid. This will make the shoulder extend backwards.

Channel 3 was used to stimulate elbow extensor, i.e. triceps. This will in combination with Channel 1 fully extend the arm in front of the subject.

Channel 4 was used to stimulate elbow flexor, i.e., biceps. This will in combination with Channel 2 generate shoulder extension placing the arm in retrieval posture that looks like "holding a ski poll next to body."

Channel 5 was used to stimulate wrist extensors, i.e. extensor digitorum, extensors carpi radialis, extensor carpi ulnaris.

Channel 6 was used to stimulate the extensor digitorum to allow finger extension at the MCP and IP joints of the fingers.

Channel 7 was used to stimulate flexor Digitorum Superficialis and Profundus. This will result in finger flexion at MCP and IP joints and hence hand closing.

Channel 8 was used to stimulate Opponens Pollicis Brevis with the electrode over the Thenar eminence or over the median nerve just proximal to the wrist joint on the radial side. This will result in opposition of the thumb.

The potential electrode placement for Channels 1-8 is shown in FIG. 11, 17, 18, 24 or 25.

Program:

Push button 1: (a) Channels 1 and 3 were activated simultaneously—Elbow extended and the shoulder flexed forward placing the arm in forward reaching position.

Push button 2: (b) Channels 1 and 3 remained on and channels 5-6 were activated simultaneously to produce wrist and finger extension so that the arm is in forward flexion with elbow, wrist and finger in extension to place the hand around the object to be grasped.

Push button 3: (c) Channels 1 and 3 remained on and channels 5-6 were decreased and simultaneously channels 7-8 will activated to allow the object to be grasped.

Push button 4: (d) Channels 1 and 3 remained on, Channels 7-8 were decreased and simultaneously 5-6 were activated to allow for release of the object by hand opening.

Push button 5: (e) Channels 5-6 were decreased so that the arm is in forward flexion and elbow in extension and the wrist and the fingers relax.

Push button 6: (f) Channels 1 and 3 were decreased and Channels 2 and 4 were activated—Elbow will flex and the shoulder will extend placing the arm in retrieval posture that looks like "holding a ski poll next to body."

Push button 7: (g) Channels 2 and 4 were decreased—the arm completely relaxes.

The protocol was repeated as necessary or desired.

The subsequent push of the push button will initiate the sequence as discussed at the beginning of the paragraph, i.e., it will start with Push button 1 (a).

Type of Movement Produced: Shoulder flexion and elbow extension followed by wrist and finger extension followed by finger flexion while the shoulder is flexed and elbow extended followed by wrist and finger extension followed by relaxation of the wrist and fingers followed by shoulder extension and elbow flexion followed by shoulder and elbow relaxation so that the arm is in neutral position.

Protocol 8—Reaching Over to the Opposite Shoulder

This protocol provided training to expand the reaching space beyond the midline of the body and to break the shoulder abduction elbow flexion pattern.

Figure 27:
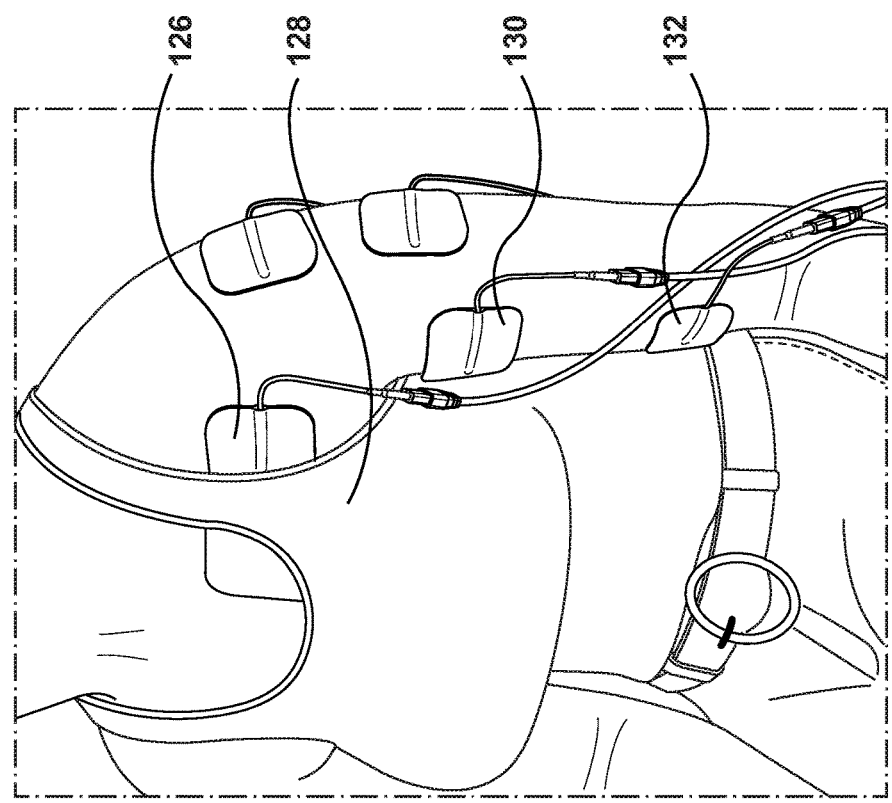

For this protocol, electrode placement for pectoralis major and biceps muscle is shown in FIG. 27. 130 is the 5×5 cm² cathode electrode (delivery electrode) for the biceps muscle, i.e., Channel #1 (CH#1). 132 is the 5×5 cm² anode electrode (i.e., return electrode) for CH#1. 128 is the 9×5 cm² cathode electrode (i.e., delivery electrode) for CHπ3. 126 is the 5×5 cm² anode electrode (i.e., return electrode) for the pectoralis major muscle, i.e., Channel #3 (CH#3).

Figure 28:
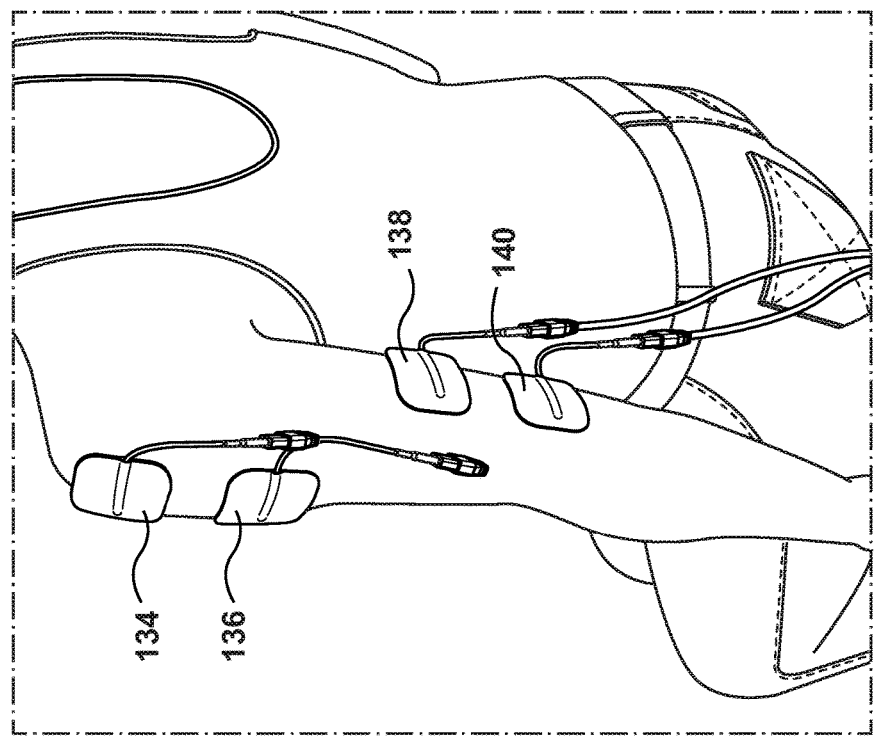
Figure 29:
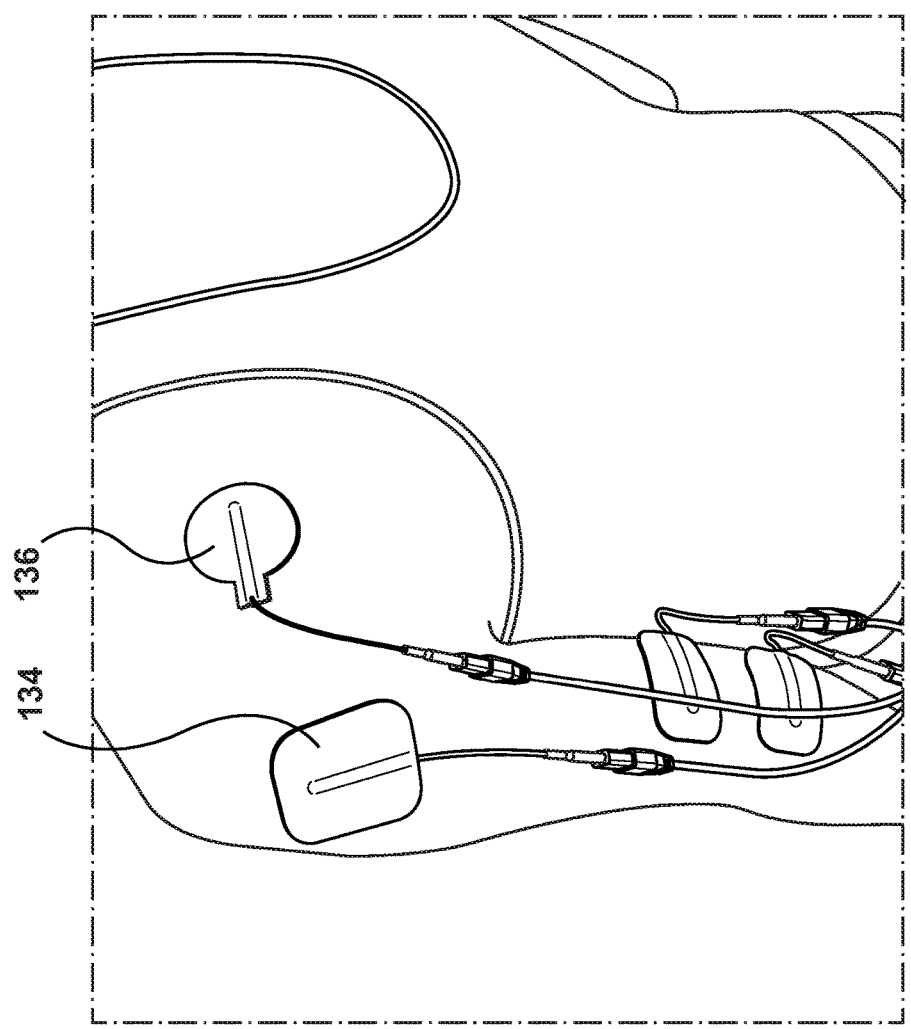

Placement of the electrodes for middle deltoid and triceps muscle is shown in FIG. 28. 134 is the 5×5 cm² cathode electrode (delivery electrode) for the middle deltoid muscle, i.e., Channel #2 (CH#2). 136 is the 5×5 cm² anode electrode (i.e., return electrode) for CH#2. 138 is the 5×5 cm² cathode electrode (delivery electrode) for the triceps muscle, i.e., Channel #4 (CH#4). 140 is the 5×5 cm² anode electrode (i.e., return electrode) for CH#4. FIG. 29 shows alternate placement of electrodes for the posterior deltoid muscles. 134 is the delivery electrode for the posterior deltoid (CH#2—alternate position). Electrode six is 2.5 cm diameter. 136 is the return electrode (CH#2—alternate position). Electrode size is 5×5 cm².

Figure 30:
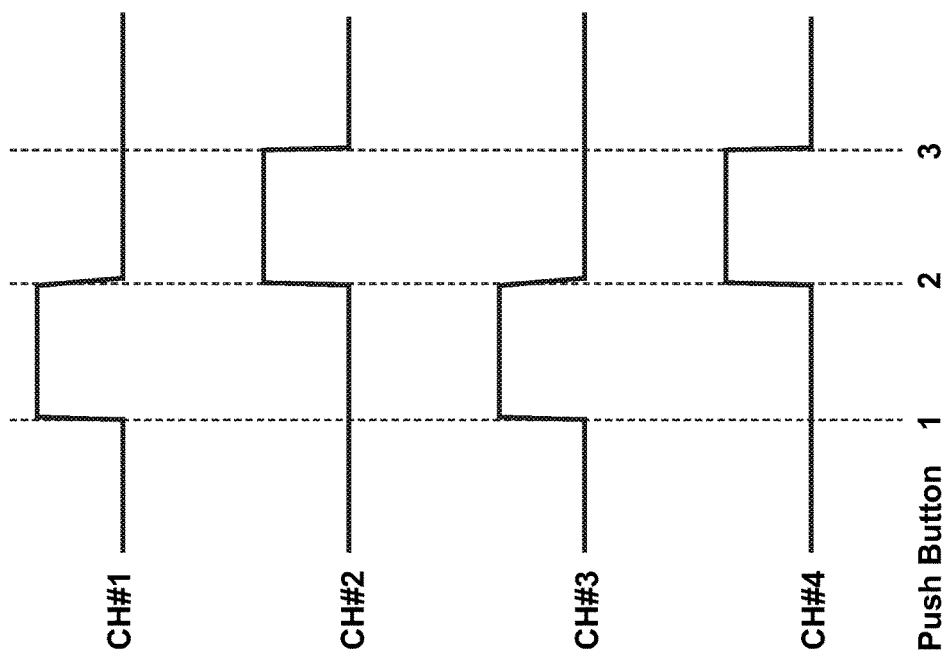

The protocol progression was shown, for the 3 steps of the protocol, in FIG. 30.

Parameters and protocol progression was as follows:

Parameters:

Pulse Duration: 400 μsec

Max Amplitude: 30 mA (the amplitude range can be much smaller pending which stimulator is used)

Ramp time: Ramp up 1 sec and ramp down 0.5 sec

Pulse frequency: 40 Hz

Channels used: Channels 1-4

Placement of the Electrodes—Muscles that May be Stimulated:

Channels 1 and 3 were used to produce the reaching movement across the opposite shoulder of the proximal upper extremity, i.e., adduction of shoulder and flexion of the elbow respectively. Channels 2 and 4 were used to return the arm to the side of the body.

Channel 1 stimulated elbow flexor, i.e., biceps.

Channel 2 stimulated shoulder abductor, i.e., middle deltoid. Occasionally posterior deltoid could be stimulated instead of middle deltoid to return the arm back to neutral position. In either case only low amplitudes were needed.

Channel 3 stimulated shoulder adductor, i.e., pectoralis major.

Channel 4 stimulated elbow extensor, i.e., triceps.

Program:

Push button 1: (a) Channels 1 and 3 were activated—This activated pectoral and biceps muscles and brought the arm to the opposite shoulder.

Push button 2: (b) Channels 1 and 3 were decreased and simultaneously Channels 2 and 4 were activated. —This produced elbow extension and the shoulder was brought back to a position that allows the arm to hang next to the body.

Push button 3: (c) Channel 2 and 4 were decreased and the arm relaxes The protocol was repeated as necessary or desired.

The subsequent push of the push button will initiate the sequence as discussed at the beginning of the paragraph, i.e., it will start the protocol from Push button 1 (a).

Type of Movement Produced: Shoulder adduction and elbow flexion followed by gentle shoulder abduction/extension to neutral and elbow extension so that the arm hangs by the side of the body.

Protocol 9—Reaching Over the Opposite Shoulder then Transfer into Sideways Reaching This protocol provided training to expand the reaching space on either side of the midline of the body and to break the shoulder abduction elbow flexion pattern.

For this protocol, electrode placement for pectoralis major and biceps muscle is shown in FIG. 27. 130 is the cathode electrode (delivery electrode) for the biceps muscle, i.e., Channel #1 (CH#1). Size of the electrode 5×5 cm². 132 is the 5×5 cm² anode electrode (i.e., return electrode) for CH#1. 128 is the 9×5 cm² cathode electrode (i.e., delivery electrode) for CH#3. 126 is the 5×5 cm² anode electrode (i.e., return electrode) for the pectoralis major muscle, i.e., Channel #3 (CH#3).

Placement of the electrodes for middle deltoid and triceps muscle is shown in FIG. 28. 134 is the cathode electrode (delivery electrode) for the middle deltoid muscle, i.e., Channel #2 (CH#2). Size of the electrode 5×5 cm². 136 is the 5×5 cm² anode electrode (i.e., return electrode) for CH#2. 138 is the 5×5 cm² cathode electrode (delivery electrode) for the triceps muscle, i.e., Channel #4 (CH#4). 140 is the 5×5 cm² anode electrode (i.e., return electrode) for CH#4. FIG. 29 shows alternate placement of electrodes for the posterior deltoid muscles. 134 is the delivery electrode for the posterior deltoid (CH#2 alternate position). Electrode six is 2.5 cm diameter. 136 is the return electrode (CH#2— alternate position). Electrode size is 5×5 cm².

Figure 31:
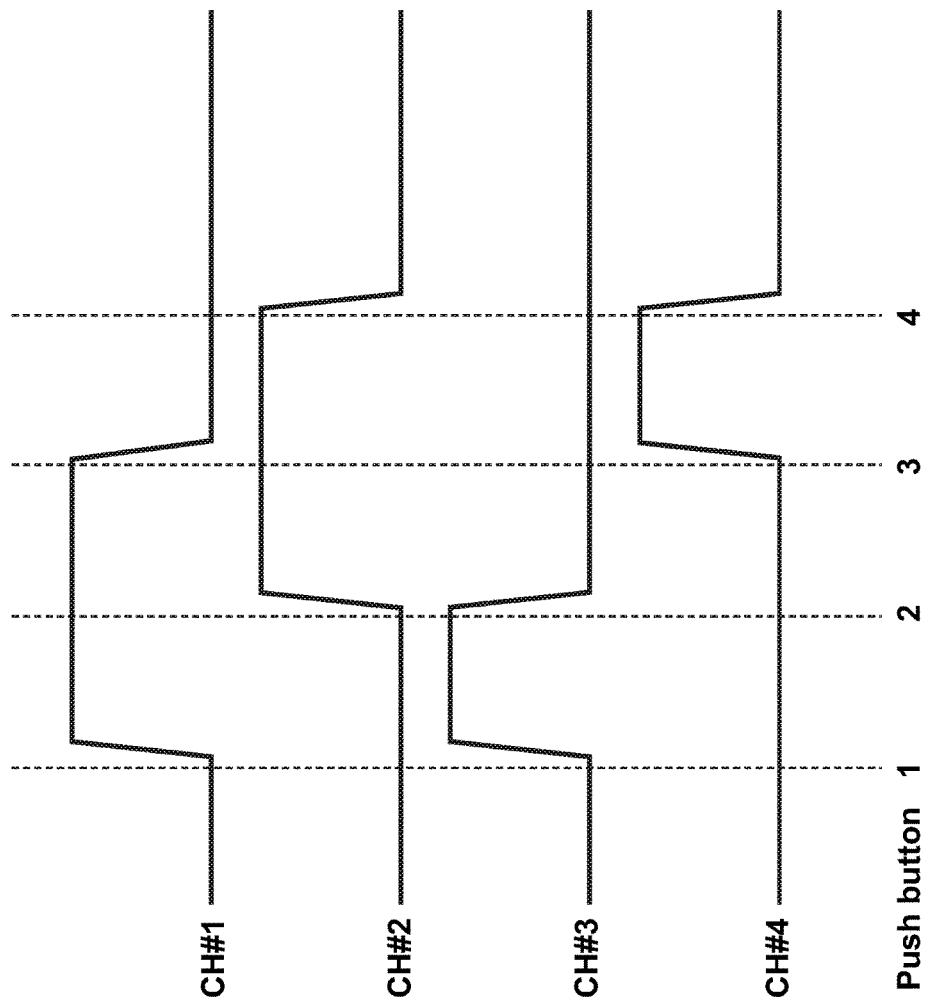

The protocol progression was shown, for the 3 steps of the protocol, in FIG. 31.

Parameters and protocol progression was as follows:
Parameters:
  Pulse Duration: 400 µsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 1-4
Placement of the Electrodes—Muscles that May be Stimulated:
  Channels 1 and 3 were used to produce the reaching movement across the opposite shoulder of the proximal upper extremity, i.e., adduction of shoulder and flexion of the elbow respectively. Channels 2 and 4 were used to return the arm to the side of the body.
  Channel 1 stimulated elbow flexor, i.e., biceps.
  Channel 2 stimulated shoulder abductor, i.e., middle deltoid.
  Channel 3 stimulated shoulder adductor, i.e., pectoralis major.
  Channel 4 stimulated elbow extensor, i.e., triceps.
Program:
  Push button 1: (a) Channels 1 and 3 were activated—This activated pectoral and biceps muscles and brought the arm to the opposite shoulder.
  Push button 2: (b) Channel 1 remained on. Channel 3 was decreased and simultaneously Channel 2 was activated—This relaxed the pectorals and activated the middle deltoid while the elbow is still in flexion.
  Push button 3: (c) Channel 2 remained on, channel 1 was decreased and simultaneously channel 4 was activated—This activated the triceps while the shoulder was in abduction.
  Push button 4: (d) Channel 2 and 4 was decreased and the arm relaxes by the side of the body.
  The protocol was repeated as necessary or desired.
  The subsequent push of the push button will initiate the sequence as discussed at the beginning of the paragraph, i.e., it will start the protocol from Push button 1 (a).
Type of Movement Produced: Shoulder adduction and elbow flexion followed by shoulder abduction and elbow flexion followed by shoulder abduction with elbow extension followed by return of arm to side of the body.

Protocol 10—Reaching Over to the Opposite Knee

This protocol provided training to expand the reaching space beyond midline of the body and to break the shoulder abduction elbow flexion pattern/shoulder adduction elbow flexion pattern.

Figure 32:
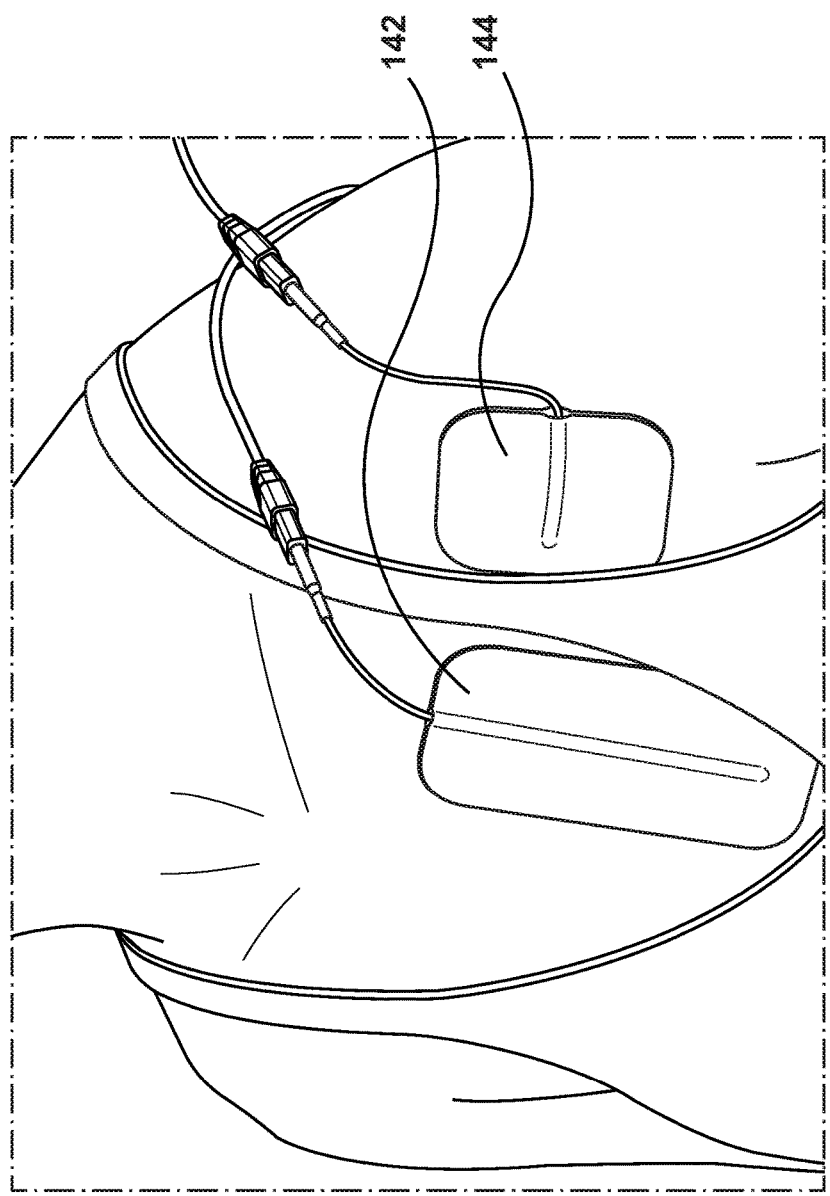

For this protocol, electrode placement for pectoralis major muscle is shown in FIG. 32. 142 is the cathode (i.e., delivery electrode) for the pectoralis major muscle (CH#2). Electrode size is 9×5 cm². 144 is the anode (i.e., return electrode) for pectoralis major muscle (CH#2). Electrode size is 5×5 cm².

Figure 33:
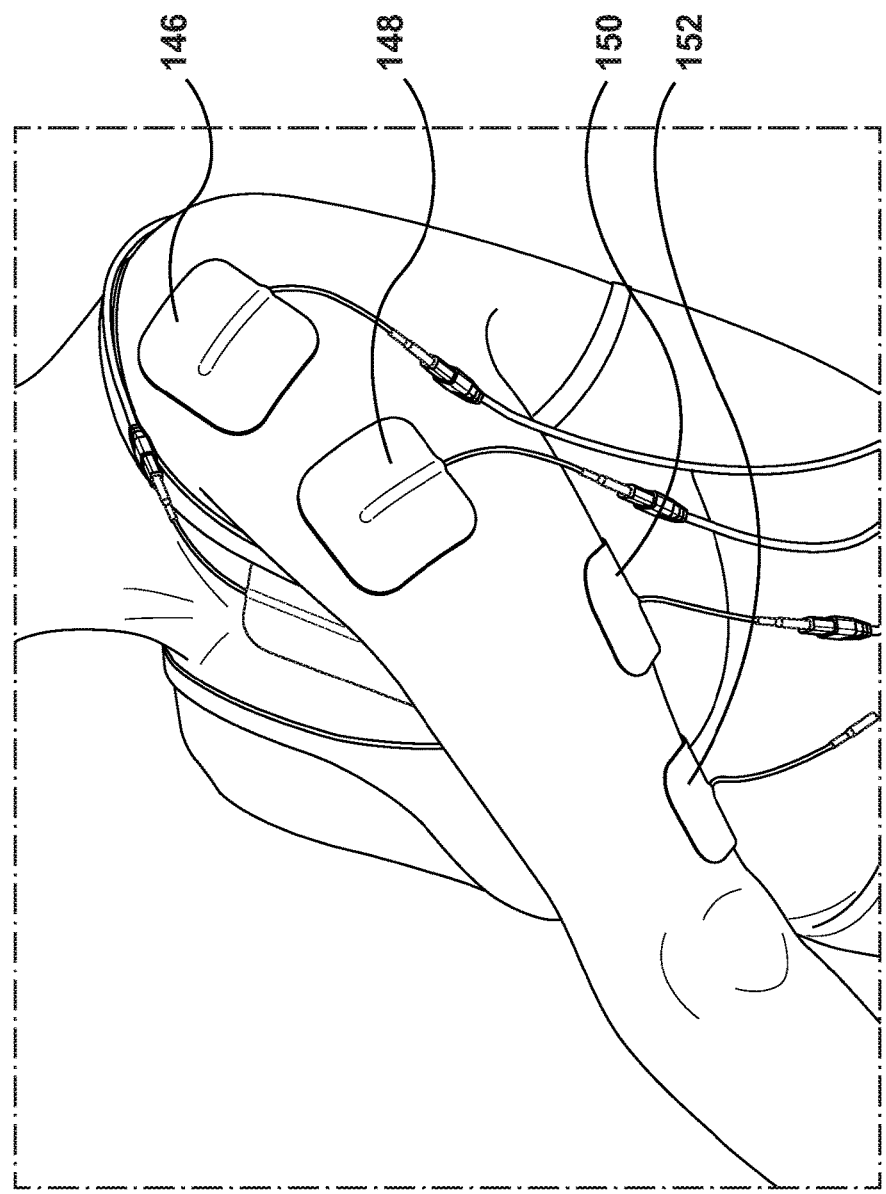

Placement of electrodes for the middle deltoid and triceps muscles can be seen in FIG. 33. 146 is the 5×5 cm² delivery electrode for the middle deltoid (CH#3). 148 is the 5×5 cm² return electrode (CH#3). 150 is the 5×5 cm² delivery electrode for triceps muscle (CH#1). 152 is the 5×5 cm² return electrode (CH#1).

Figure 34:
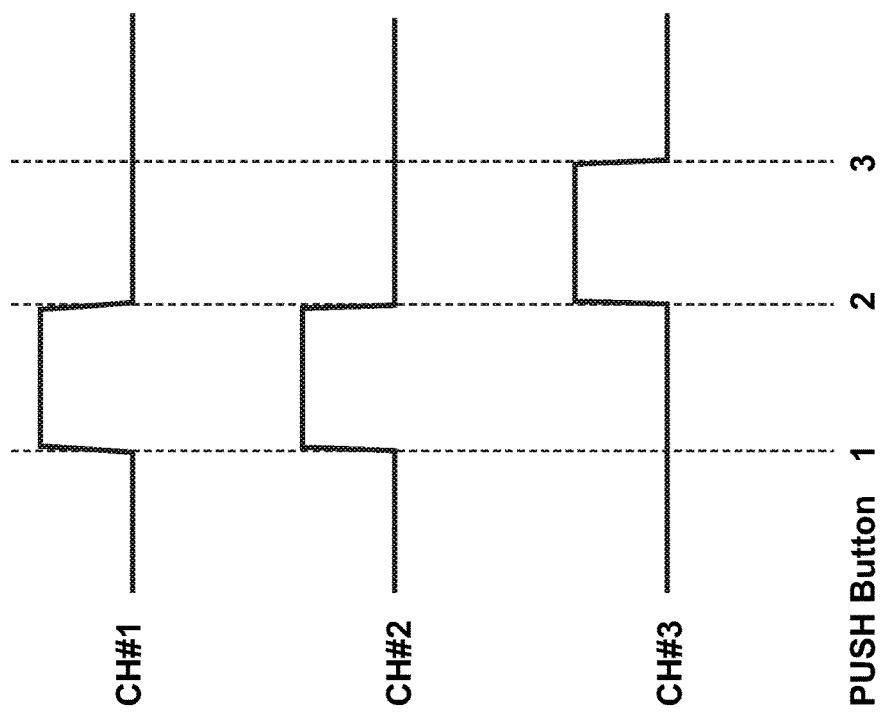

The protocol progression was shown, for the 3 steps of the protocol, in FIG. 34.

Parameters and protocol progression was as follows:
Parameters:
  Pulse Duration: 400 µsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 1-3
Placement of the Electrodes—Muscles that May be Stimulated:
  Channels 1 and 2 were used to produce the reaching movement across to the opposite knee of the proximal upper extremity, i.e., adduction of shoulder and extension of the elbow respectively. Channel 3 was used to return the arm back to neutral position.
  Channel 1 was used to stimulate elbow extensors, i.e., triceps.
  Channel 2 was used to stimulate shoulder adductors, i.e., pectoralis major.
  Channel 3 was used to stimulate shoulder abductor, i.e., middle deltoid. Occasionally instead of the middle deltoid, posterior deltoid may be stimulated to return the arm back to neutral position. In either case only low amplitudes of current were sufficient.
Program:
  Push button 1: (a) Channels 1 and 2 were activated—This activated pectoral and triceps muscles and will bring the arm to the opposite knee.
  Push button 2: (b) Channels 1 and 2 decreased and simultaneously Channel 3 was activated. —This produced elbow relaxation and the shoulder was brought back to posture that allows the arm to hang freely next to the body.
  Push button 3: (c) Channel 3 was decreased and the arm was relaxed.
  The protocol was repeated as necessary or desired.
  The subsequent push of the push button will initiate the sequence as discussed at the beginning of the paragraph, i.e., it will start the protocol from Push button 1 (a).
Type of Movement Produced: Shoulder adduction and elbow extension followed by gentle shoulder abduction/extension to neutral so that the arm hangs by the side of the body.

Protocol 11—Hand to Mouth

This protocol provided training in preparation of functional training for feeding, self-care, as well as training of shoulder elevation in a short lever position.

Figure 35:
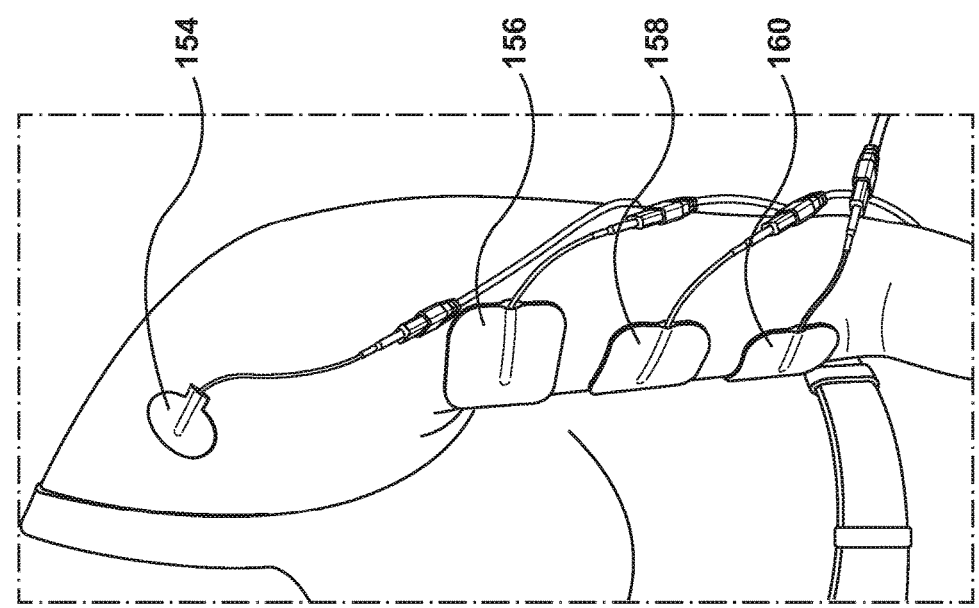

FIG. 35 shows placement of the electrodes for ant. deltoid and biceps muscles. 154 is the 2.5 cm in diameter cathode electrode (delivery electrode) for the ant. deltoid muscle, i.e., Channel #1 (CH#1). 156 is the 5×5 cm$^2$ anode electrode (i.e., return electrode) for CH#1. 158 is the 5×5 cm$^2$ cathode electrode (delivery electrode) for the biceps i.e., Channel#3 (CH#3). 160 is the 5×5 cm$^2$ anode electrode (return electrode) for the biceps.

Figure 36:
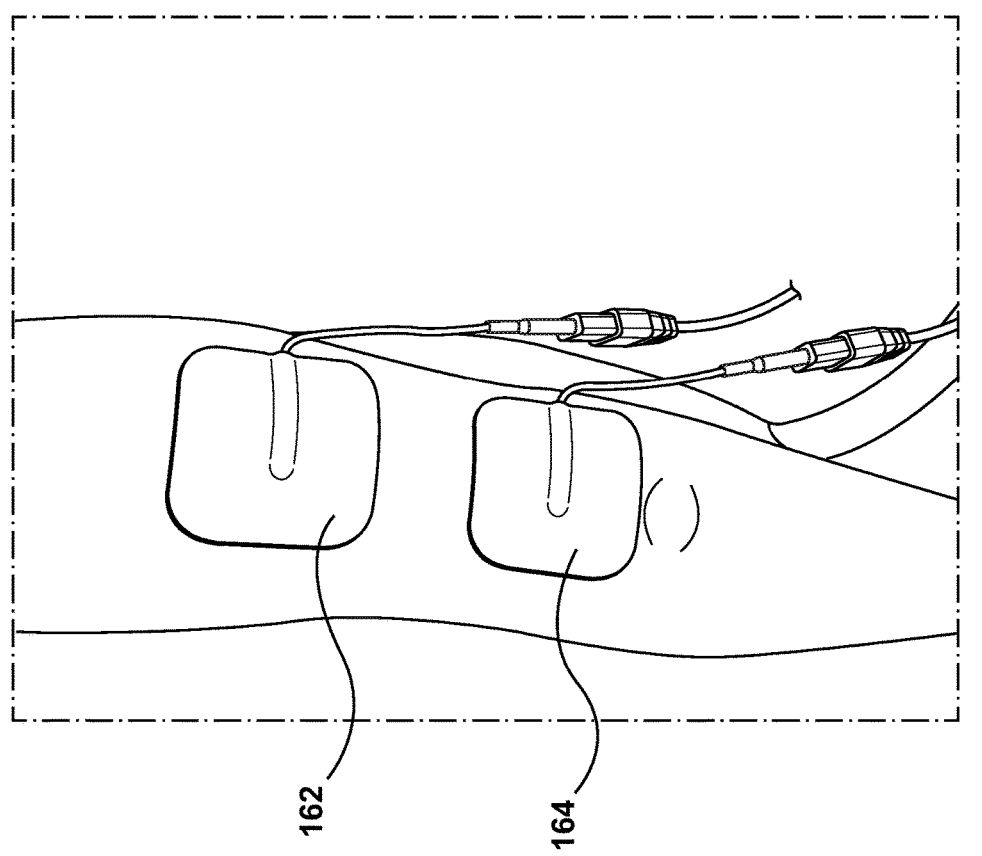

FIG. 36 shows placement of the electrodes for triceps muscle. 162 is the 5×5 cm$^2$ cathode electrode (delivery electrode) for the triceps muscle, i.e., Channel #2 (CH#2). 164 is the 5×5 cm$^2$ anode electrode (i.e., return electrode) for CH#2.

Figure 37:
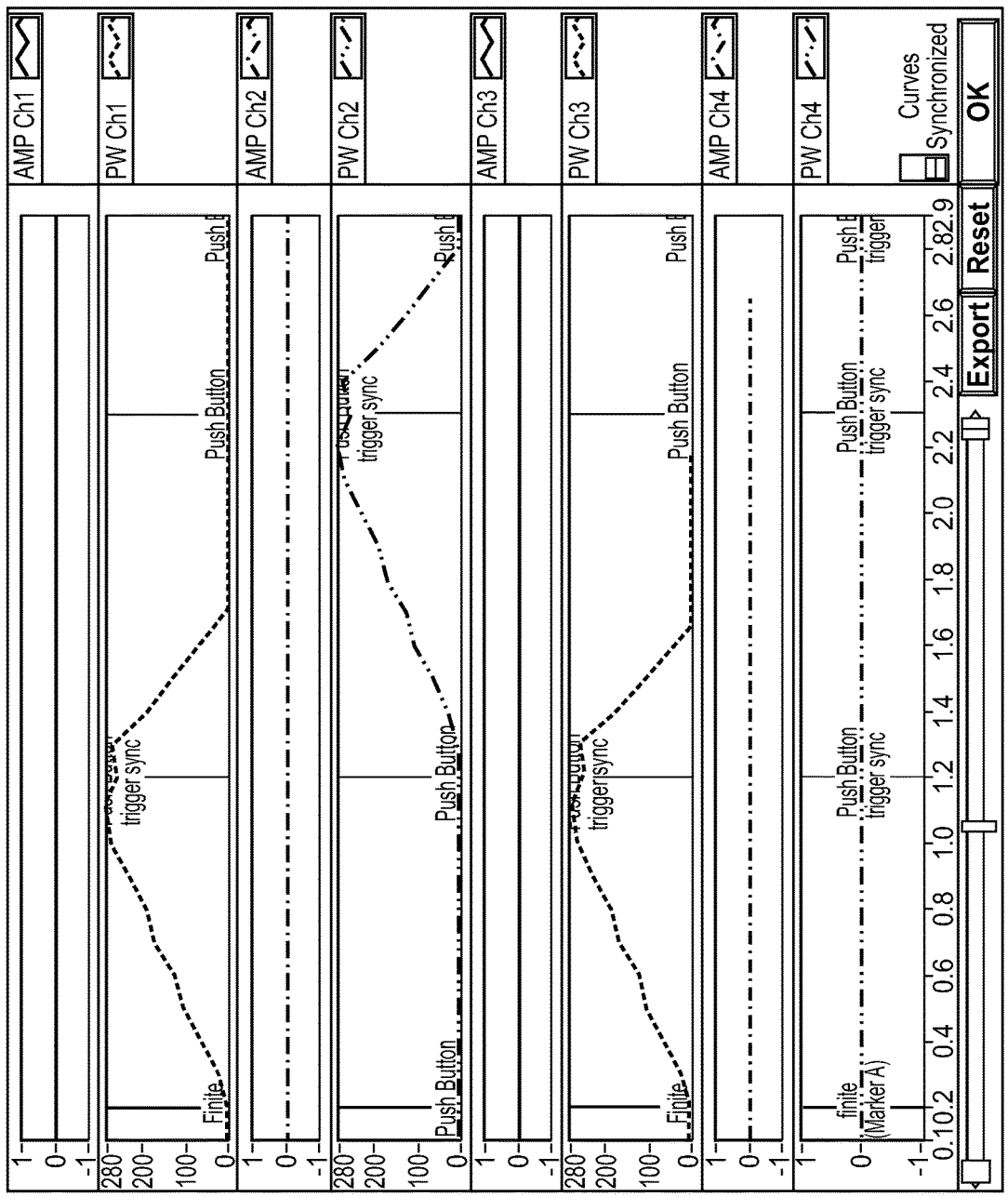
Figure 38:
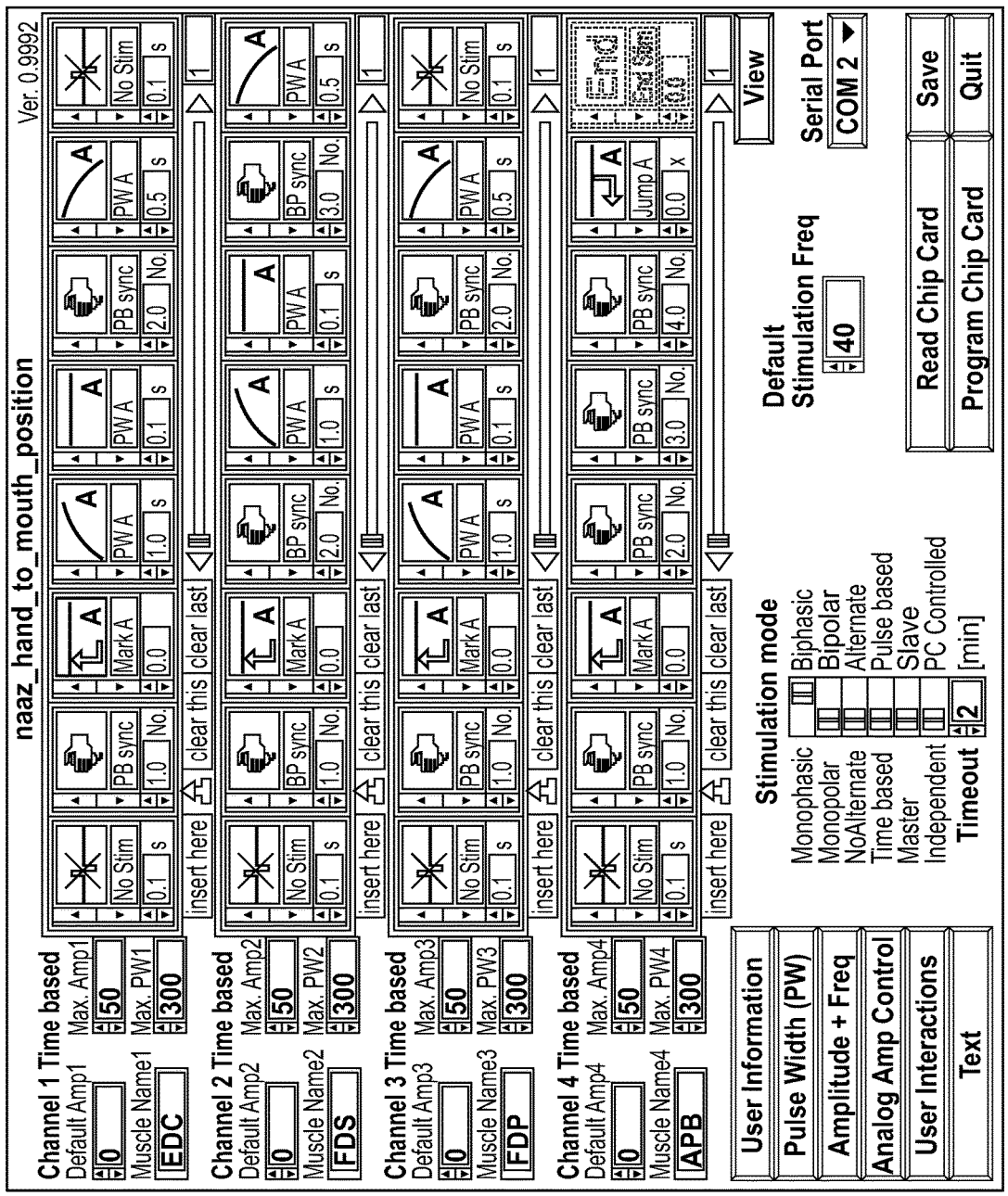

The protocol progression was shown, for the 3 steps of the protocol, in FIG. 37. Pulse amplitudes, pulse durations and ramp times are shown in FIG. 38.

Parameters and protocol progression were as follows:
Parameters:
Parameters:
 Pulse Duration: 400 μsec
 Max Amplitude: 30 mA (the amplitude range can be much smaller pending which stimulator is used)
 Ramp time: Ramp up 1 sec and ramp down 0.5 sec
 Pulse frequency: 40 Hz
 Channels used: Channels 1-3
Placement of the Electrodes—Muscles that May be Stimulated:

Channels 1 and 3 were used to produce the hand to mouth movement of the proximal upper extremity, i.e., flexion of shoulder and flexion of the elbow respectively. Channel 1 was used to stimulate forward shoulder flexors, i.e., anterior deltoid, and Channel 3 was used to stimulate elbow flexors, i.e., biceps. Channel 2 may or may not be used based on patient ability to extend elbow voluntarily, if used then Channel 2 produced elbow extension by stimulating the elbow extensors, i.e., triceps.
 Channel 1 stimulated shoulder flexor, i.e. anterior deltoid. This will position the shoulder in flexion and place the arm forward in front of the body.
 Channel 2 stimulated elbow extensor, i.e., triceps. This will make the shoulder extend.
 Channel 3 stimulated elbow flexor, i.e., biceps. This will in combination with Channel 1 fully flex the arm i.e. flex the elbow and reinforce flexion of the shoulder generating hand to mouth movement.
Program:
 Push button 1: (a) Channels 1 and 3 were activated—Hand to mouth movement
 Push button 2: (b) Channels 1 and 3 were decreased and simultaneously Channel 2 was activated (if Channel 2 is used) to assist with elbow extension to return the arm back to neutral position.
 Push button 3: (c) Channel 2 was decreased, the arm will fully relax and the protocol will be brought to the beginning.
 The protocol was repeated as necessary or desired.
 The subsequent push of the push button will initiate the sequence as discussed at the beginning of the paragraph, i.e., it will start with Push button 1 (a).
 Type of Movement Produced: (a) Shoulder flexion and elbow flexion (push button 1), (b) followed by shoulder extension to neutral and elbow extension (push button 2), and (c) full relaxation of the arm (push button 3).
Protocol 12a and 12b
 12a—Extensor Communis Opening+Palmar Grasp Using Thenar Eminence—Late SCI and Stroke (Open/Close/Open)
 12b—Extensor Communis Opening+Palmar Grasp Using Median Nerve—Late SCI and Stroke (Open/Close/Open).

This protocol provided training for grasping of large and heavier objects such as pop cans, jars, books, tennis balls, etc.

Figure 39:
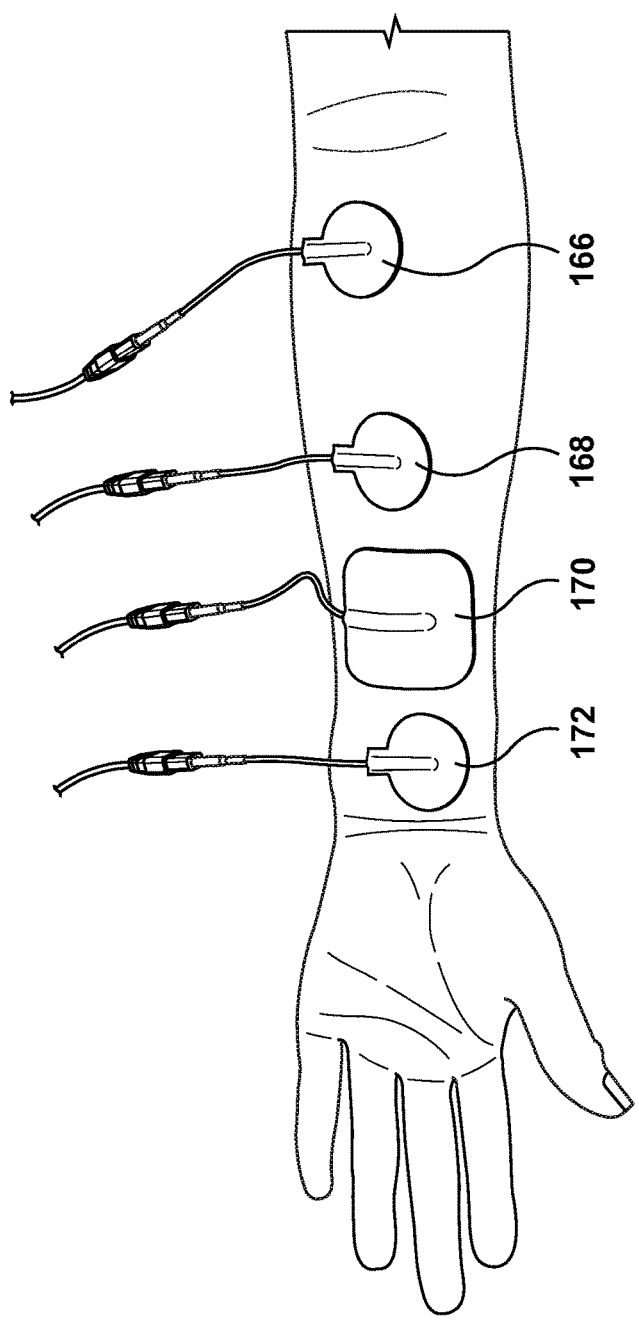
Figure 40:
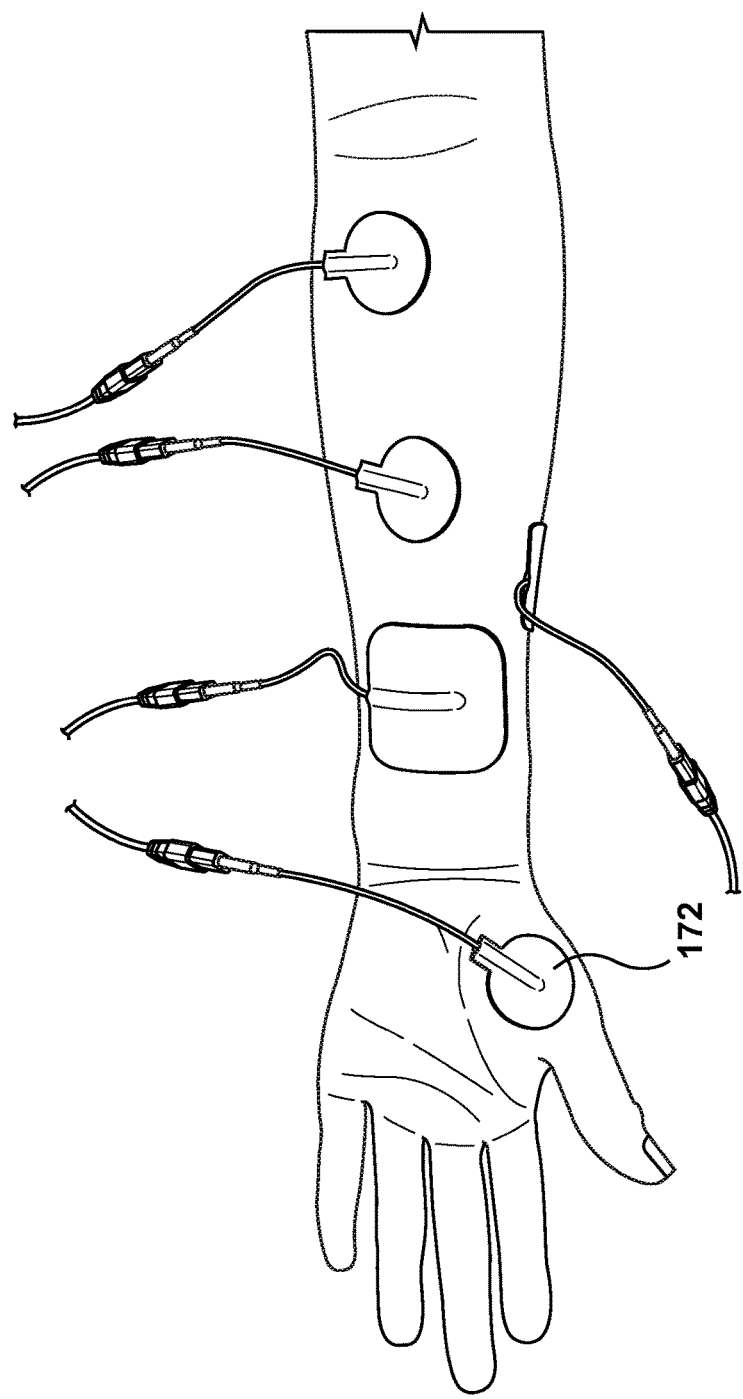

For this protocol, electrode placement for Flexor Digitorum Superficialis and Profundus muscle and Median nerve for Opponens Pollicis Brevis can be seen in FIG. 39. 166 and 168 are the 2.5 cm in diameter cathode (i.e., delivery electrode) for Flexor Digitorum Superficialis and Profundus, i.e. channel 6 and channel 7. 172 is the cathode (delivery electrode) for the Median nerve i.e. channel #8. Electrode size for electrodes 6,7 and 8 is 2.5 cm diameter. 170 is the 5×5 cm$^2$ anode for channels 6,7, and 8. Alternate placement for 172 can be shown at FIG. 40.

Figure 41:
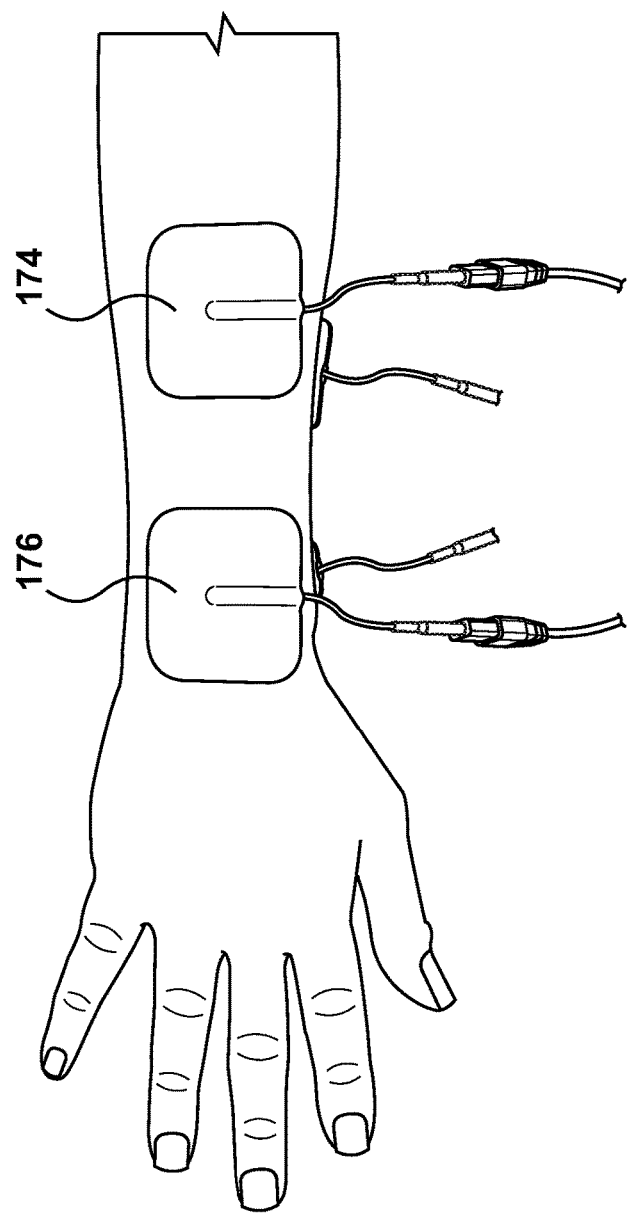

Placement of electrodes for Extensor Digitorum communis, Extensor carpi radialis, Extensor carpi ulnaris muscles can be seen in FIG. 41. 174 is the 5×5 cm$^2$ cathode (delivery electrode) for Extensor Digitorum communis, Extensor carpi radialis, Extensor carpi ulnaris, i.e. channel 5. 176 is the 5×5 cm$^2$ anode (return electrode) for channel 5.

Figure 42:
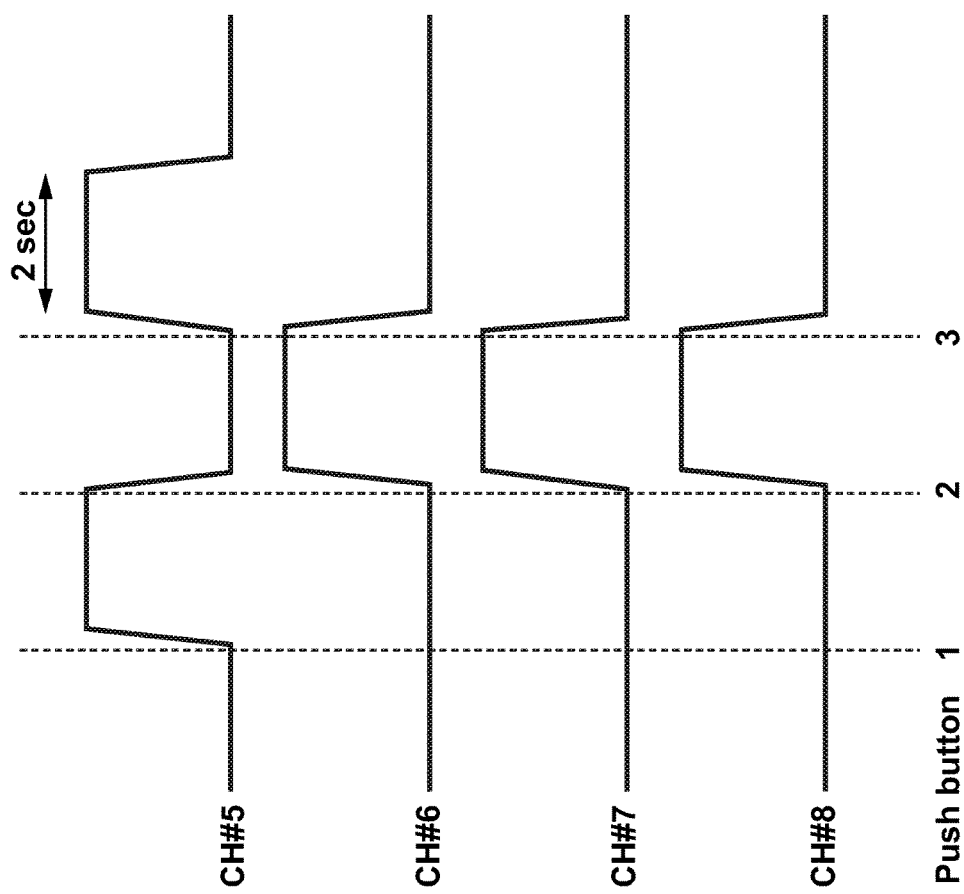

The protocol progression was shown, for the 3 steps of the protocol, in FIG. 42.

Parameters and protocol progression were as follows:
Parameters:
 Pulse Duration: 400 μsec
 Max Amplitude: 30 mA (the amplitude range can be much smaller pending which stimulator is used)
 Ramp time: Ramp up 1 sec and ramp down 0.5 sec
 Pulse frequency: 40 Hz
 Channels used: Channels 5-8
Placement of the Electrodes—Muscles that May be Stimulated:

Channel 5 was used to produce hand opening, Channels 6 and 7 were used to produce finger flexion and Channel 8 was used to produce thumb opposition.
 Channel 5 was used to produce hand opening and stimulated the long finger extensors, i.e., extensor digitorum communis and was placed over the dorsal aspect of the forearm.
 Channels 6 and 7 were used to produce hand closing and stimulated long finger flexors, i.e., flexor digitorum superficialis and flexor digitorum profundus and were be placed over the ventral aspect of the forearm.
 Channel 8 was used to produce opposition of the thumb and will stimulate thumb oppositor, i.e., opponens pollicis brevis and can be placed either over the median nerve just proximal to the wrist joint or over the Thenar eminence of the hand.
Program:
 Push button 1: (a) Channel 5 was activated—finger extension, i.e., hand opening
 Push button 2: (b) Channel 5 was decreased and Channels 6-8 were activated simultaneously to produce palmar grip
 Push button 3: (c) Channels 6-8 were decreased and simultaneously Channel 5 was activated, stay contracted for 2 sec and was then decreased—This produced hand opening for 2 seconds and relaxation of the hand.
 The protocol was repeated as necessary or desired.
 The subsequent push of the push button will initiate the sequence as discussed at the beginning of the paragraph, i.e., it will start with Push button 1 (a).
 Type of Movement Produced: (a) Finger extension (push button 1), (b) followed by finger and thumb flexion (push button 2), (c) followed by finger relaxation and hand opening for 2 seconds and later hand relaxation.

Figure 43:
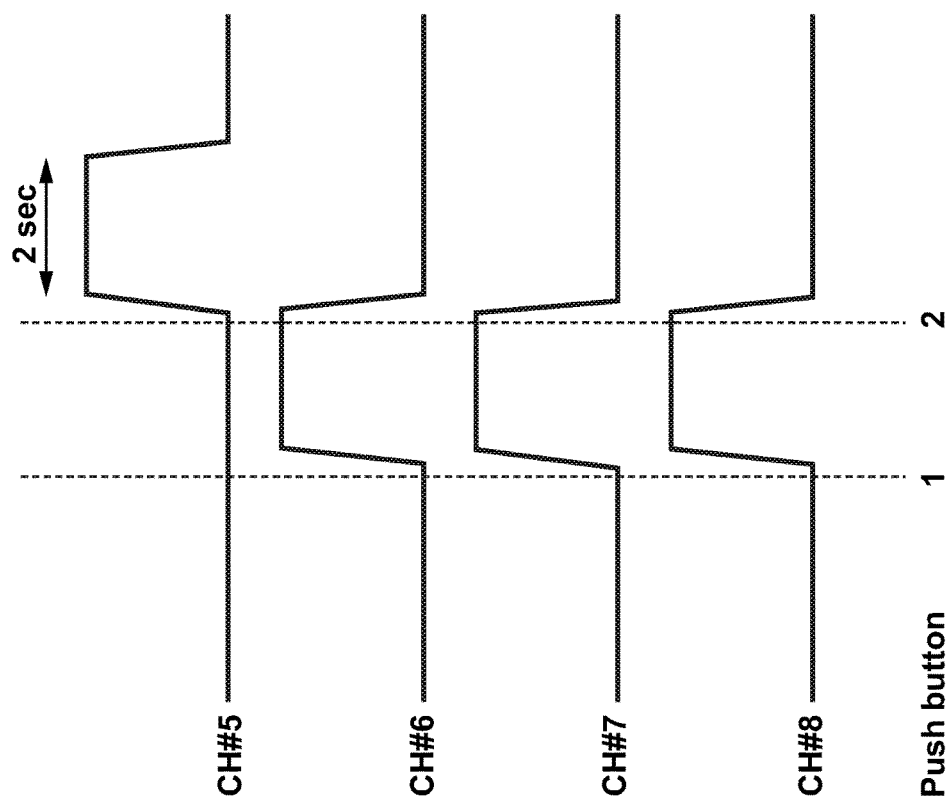

Protocol 13a and 13b—
  13a—Palmar Grasp Using Thenar Eminence+Extensor Communis Opening—SCI (Close/Open)
  13b—Palmar Grasp Using Median Nerve+Extensor Communis Opening—SCI (Close/Open)
  This protocol provided training for grasping of large and heavier objects such as pop cans, jars, books, tennis balls, etc.
  For this protocol, Electrode placement for Flexor Digitorum Superficialis and Profundus muscle and Median nerve for Opponens Pollicis Brevis can be seen in FIG. 39. 166 and 168 are the 2.5 cm in diameter cathode (i.e., delivery electrode) for Flexor Digitorum Superficialis and Profundus, i.e. channel 6 and channel 7. 172 is the 2.5 cm in diameter cathode (delivery electrode) for the Median nerve, i.e. channel 8. 170 is the 5×5 cm² anode for channels 6,7, and 8. Alternate placement for 172 can be shown at FIG. 40.
  Placement of electrodes for Extensor Digitorum communis, Extensor carpi radialis, Extensor carpi ulnaris muscles can be seen in FIG. 41. 174 is the 5×5 cm² cathode (delivery electrode) for Extensor Digitorum communis, Extensor carpi radialis, Extensor carpi ulnaris, i.e. channel 5. 176 is the 5×5 cm² anode (return electrode) for channel 5.
  The protocol progression was shown, for the 3 steps of the protocol, in FIG. 43.
  Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 5-8
Placement of the Electrodes—Muscles that May be Stimulated:
  Channel 5 was used to produce hand opening, Channels 6 and 7 were used to produce finger flexion and Channel 8 was used to produce thumb opposition.
    Channel 5 was used to produce hand opening and stimulated the long finger extensors, i.e., extensor digitorum communis and was placed over the dorsal aspect of the forearm.
    Channels 6 and 7 were used to produce hand closing and stimulated long finger flexors, i.e., flexor digitorum superficialis and flexor digitorum profundus and were placed over the ventral aspect of the forearm.
    Channel 8 was used to produce opposition of the thumb and stimulated thumb oppositor, i.e., opponens pollicis brevis and can be placed either over the median nerve just proximal to the wrist joint or over the Thenar eminence of the hand.
Program:
  Before pressing a push button the patient placed their hand around the object he/she wanted to grasp. This was a passive, over or around the object sliding motion. Once the hand and fingers were in passive grasp position the protocol progressed.
  Push button 1: (a) Channels 6-8 were activated simultaneously to produce palmar grip
  Push button 2: (b) Channels 6-8 decreased and simultaneously Channel 5 was activated, stay activated (i.e. the hand would stay contracted) for 2 sec and then was decreased—This produced hand opening for 2 seconds and relaxation of the arm
  The protocol was repeated as necessary or desired.

Figure 44:
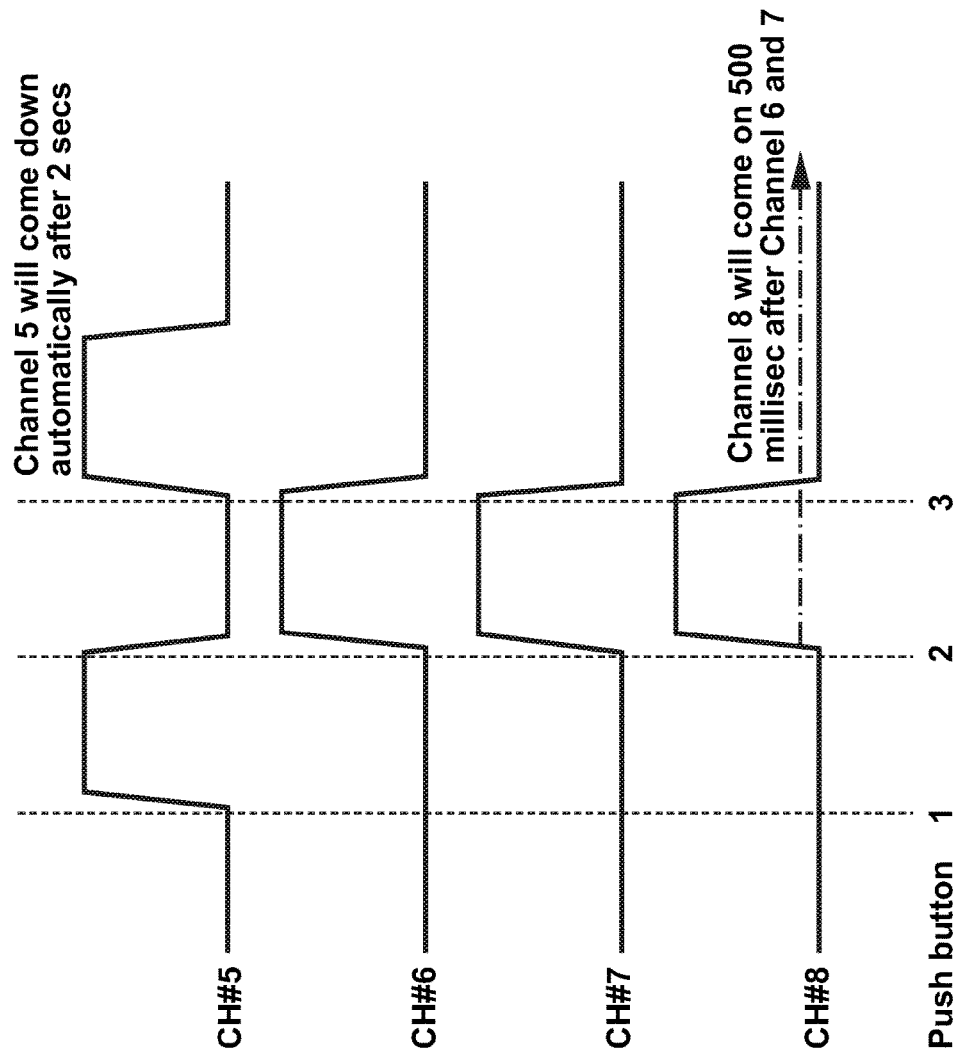

The subsequent push of the push button will initiate the sequence as discussed at the beginning of the paragraph, i.e., it will start with Push button 1 (a).
  Type of Movement Produced: (a) Finger flexion combined with thumb opposition, and (b) followed by finger relaxation and hand opening for 2 seconds and later hand relaxation.
Protocol 14a and 14b—
  14a. Extensor Communis Opening+Lateral Pinch Grasp Using Thenar Eminence—Late SCI and Stroke (Open/Close/Open)
  14b. Extensor Communis Opening+Lateral Pinch Grasp Using Median Nerve—Late SCI and Stroke (Open/Close/Open)
  This protocol provided training for grasping of thin objects such as a paper sheet, a key, zip lock bag, etc.
  For this protocol, electrode placement for Flexor Digitorum Superficialis and Profundus muscle and Median nerve for Opponens Pollicis Brevis can be seen in FIG. 39. 166 and 168 are the 2.5 cm in diameter cathode (i.e., delivery electrode) for Flexor Digitorum Superficialis and Profundus, i.e. channel 6 and channel 7. 172 is the 2.5 cm in diameter cathode (delivery electrode) for the Median nerve, i.e. channel 8. 170 is the 5×5 cm² anode for channels 6,7, and 8. Alternate placement for 172 can be shown at FIG. 40.
  Placement of electrodes for Extensor Digitorum communis, Extensor carpi radialis, Extensor carpi ulnaris muscles can be seen in FIG. 41. 174 is the 5×5 cm² cathode (delivery electrode) for Extensor Digitorum communis, Extensor carpi radialis, Extensor carpi ulnaris, i.e. channel 5. 176 is the 5×5 cm² anode (return electrode) for channel 5.
  The protocol progression was shown, for the 3 steps of the protocol, in FIG. 44.
  Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 5-8
Placement of the Electrodes—Muscles that May be Stimulated:
  Channel 5 was used to produce hand opening, Channels 6 and 7 were used to produce finger flexion and Channel 8 was used to produce thumb flexion.
    Channel 5 was used to produce hand opening and stimulated the long finger extensors, i.e., extensor digitorum communis and was placed over the dorsal aspect of the forearm.
    Channels 6 and 7 were used to produce hand closing and stimulated long finger flexors, i.e., flexor digitorum superficialis and flexor digitorum profundus and were placed over the ventral aspect of the forearm.
    Channel 8 was used to produce flexion of the thumb and stimulated thumb flexors, i.e., flexor pollicis brevis and could be placed either over the median nerve just proximal to the wrist joint or over the Thenar eminence of the hand.
Program:
  Push button 1: (a) Channel 5 was activated—finger extension, i.e., hand opening
  Push button 2: (b) Channel 5 was decreased and Channels 6-7 were activated simultaneously. 500 millisec following activation of Channels 6 -7, Channel 8 was activated bringing thumb in flexion—This produced lateral pinch grip Push button 3: (c) Channels 6-8 were decreased and simultaneously Channel 5 was activated, stay activated for 2 sec and was then decreased—This produced hand opening for 2 seconds and relaxation of the hand.

The protocol was repeated as necessary or desired.

The subsequent push of the push button will initiate the sequence as discussed at the beginning of the paragraph, i.e., it will start with Push button 1 (a).

Type of Movement Produced: (a) Finger extension (push button 1), (b) followed by finger flexion followed by thumb flexion (push button 2), (c) followed by finger relaxation and hand opening for 2 seconds and later hand relaxation.

Protocol 15a and 15b—
  15.a—Lateral Pinch Grasp Using Thenar Eminence+Extensor Communis Opening—SCI (Close/Open)
  15.b—Lateral Pinch Grasp Using Median Nerve+Extensor Communis Opening—SCI (Close/Open)

This protocol provided training for grasping of thin objects such as a paper sheet, a key, zip lock bag, etc.

For this protocol, electrode placement was identical to protocols 14a and 14b, respectively.

Figure 45:
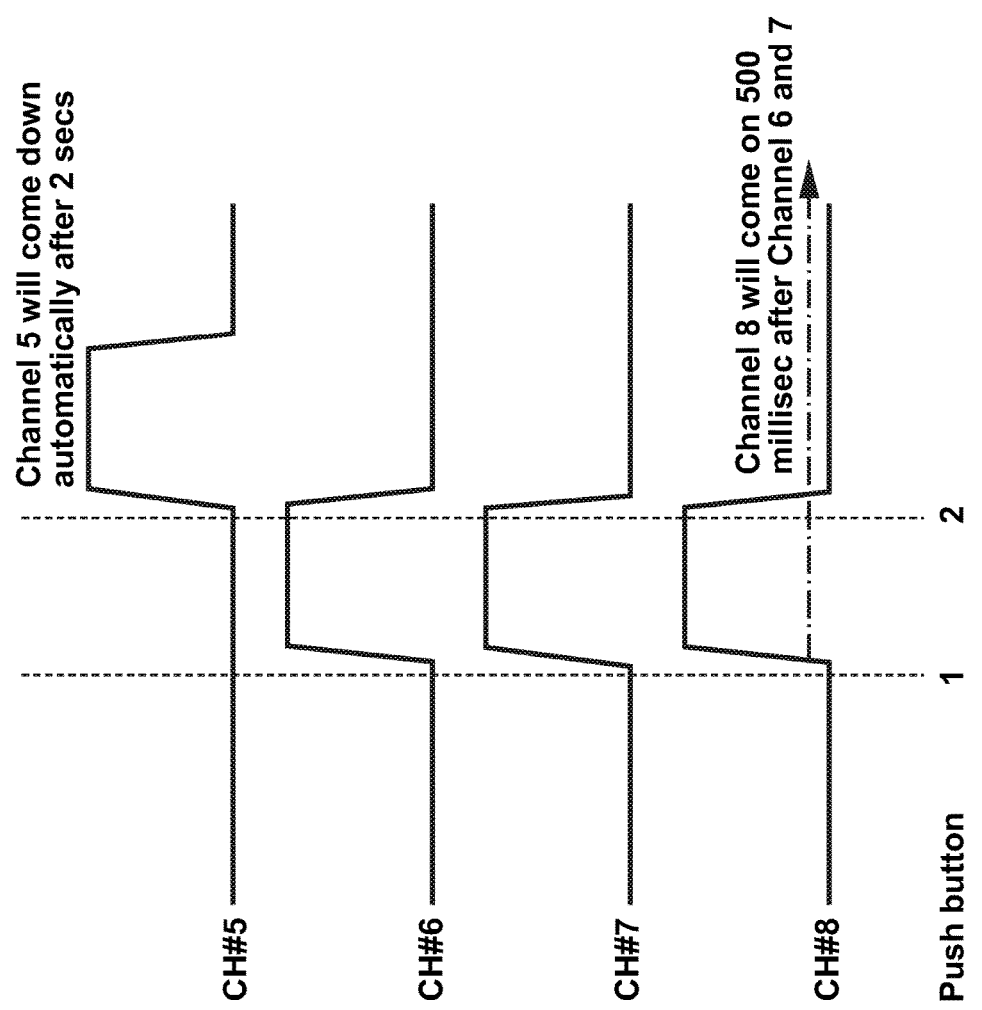

The protocol progression was shown, for the 3 steps of the protocol, in FIG. 45.

Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 5-8

Placement of the Electrodes—Muscles that May be Stimulated:
  Channel 5 was used to produce hand opening, Channels 6 and 7 were used to produce finger flexion and Channel 8 was used to produce thumb flexion.
    Channel 5 was used to produce hand opening and stimulated the long finger extensors, i.e., extensor digitorum communis and was placed over the dorsal aspect of the forearm.
    Channels 6 and 7 were used to produce hand closing and stimulated long finger flexors, i.e., flexor digitorum superficialis and flexor digitorum profundus and was placed over the ventral aspect of the forearm.
    Channel 8 was used to produce flexion of the thumb and stimulated thumb flexors, i.e., flexor pollicis brevis and could be placed either over the median nerve just proximal to the wrist joint or over the Thenar eminence of the hand.

Program:
  Before pressing a push button the patient should place the hand around the object he/she wants to grasp. This can be a passive, over or around the object sliding motion. Once the hand and fingers are in passive grasp position proceed with the protocol.
  Push button 1: (a) Channels 6-7 were activated simultaneously. 500 millisec following Channels 6-7 activation Channel 8 was activated bringing thumb in flexion—this produced lateral pinch grip
  Push button 2: (b) Channels 6-8 were decreased and simultaneously Channel 5 was activated, remain activated for 2 sec and then was decreased—This produced hand opening for 2 seconds and relaxation of the arm The protocol was repeated as necessary or desired.

The subsequent push of the push button will initiate the sequence as discussed at the beginning of the paragraph, i.e., it will start with Push button 1 (a).

Type of Movement Produced: (a) Finger flexion followed by thumb flexion, and (b) followed by finger relaxation and hand opening for 2 seconds and later hand relaxation.

Protocol 16a and 16b
  16.a Extensor Communis Opening+Pinch Grasp Using Thenar Eminence—Late SCI and Stroke (Open/Close/Open)
  16.b Extensor Communis Opening+Pinch Grasp Using Median Nerve —Late SCI and Stroke (Open/Close/Open)

In this protocol smaller objects are manipulated using this type of grip like a pencil or a dice (by stimulating flexor digitorum superficialis) or a peg (by stimulating the dorsal interossei) etc.

Figure 46:
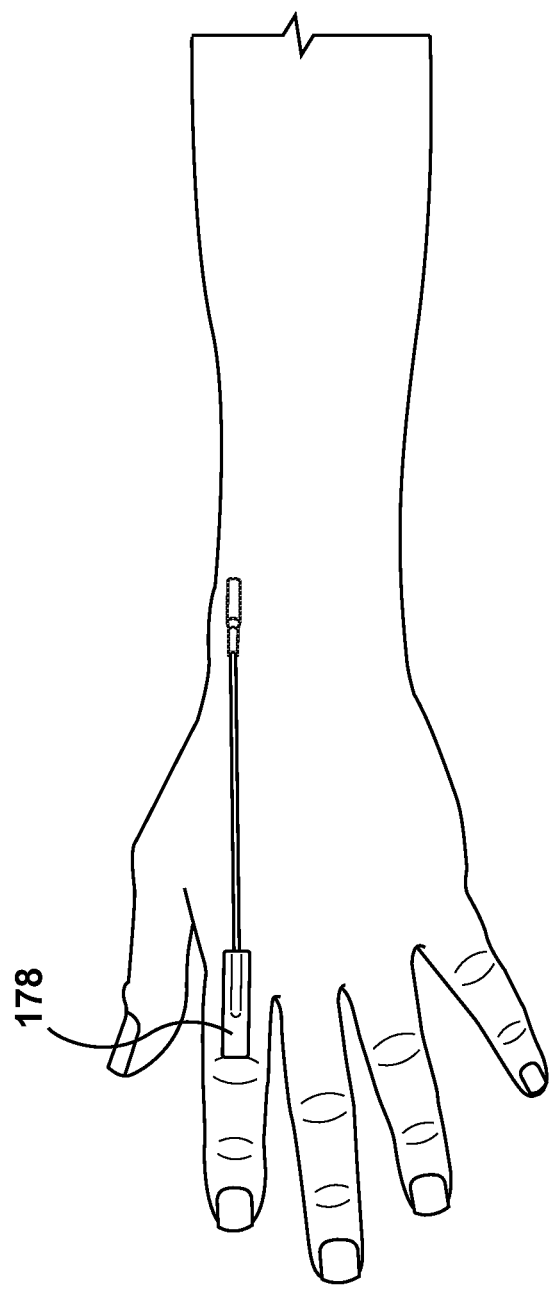
Figure 47:
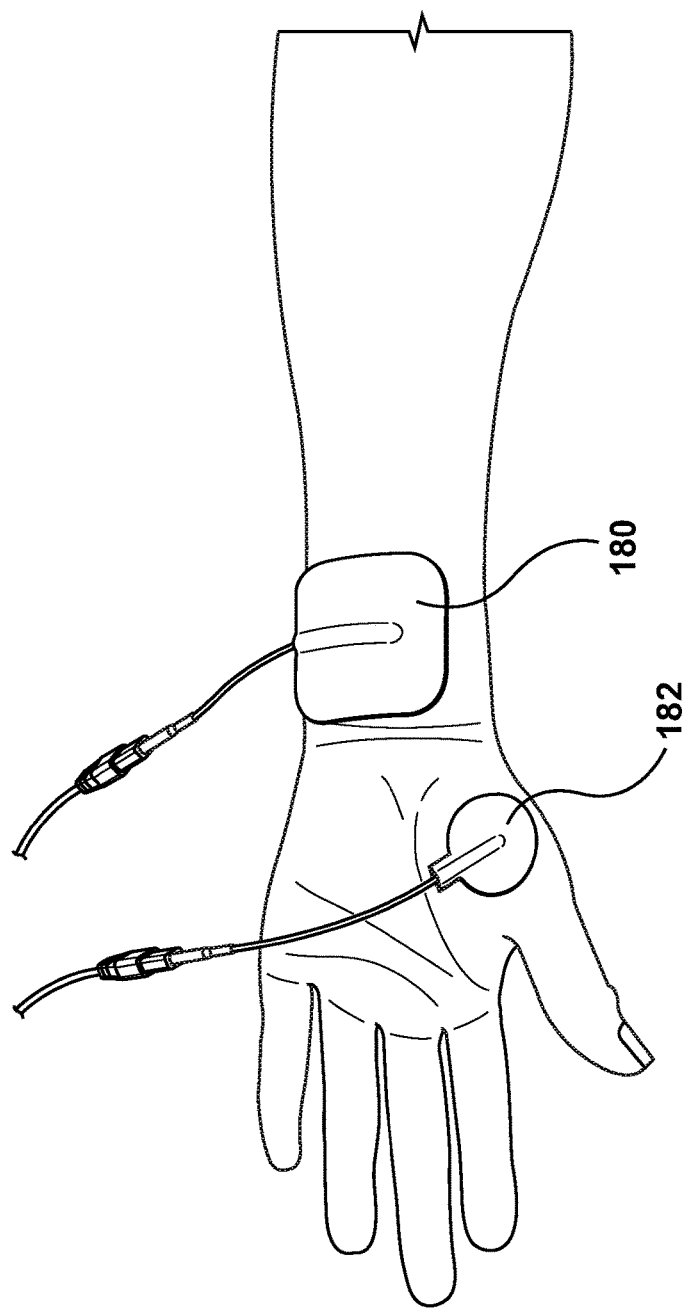
Figure 48:
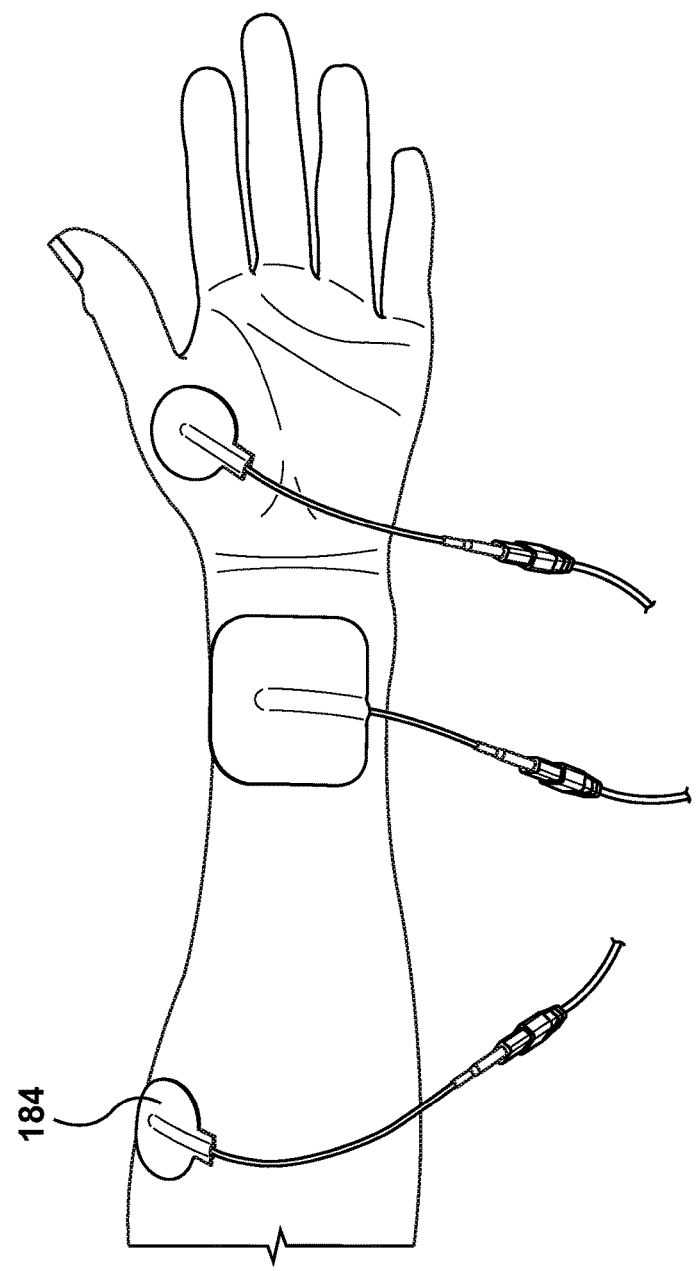

For this protocol, placement of electrode for the 1$^{st}$ Lumbrical muscle is shown in FIG. 46. Electrode 178 is placed over the dorsal aspect of the 1$^{st}$ phalanx of the index finger (Channel 6) and is the delivery electrode. Electrode size is 2×1 cm. Placement of electrodes for Opponens Pollicis is shown in FIG. 47. 180 is the 5×5 cm$^2$ return electrode for 1$^{st}$ Lumbrical muscle and Opponens Pollicis Brevis muscle (channels 6 and 7). 182 is the delivery electrode for Opponens Pollicis Brevis (channel 7). Electrode size is 2.5 cm diameter. An alternate position for electrode 178 is shown in FIG. 48 as 184. Placement of electrodes for Extensor Digitorum Communis can be seen as FIG. 49, with 186 the 5×5 cm$^2$ delivery electrode for channel 5. 188 is the 5×5 cm$^2$ return electrode for channel 5.

Figure 50:
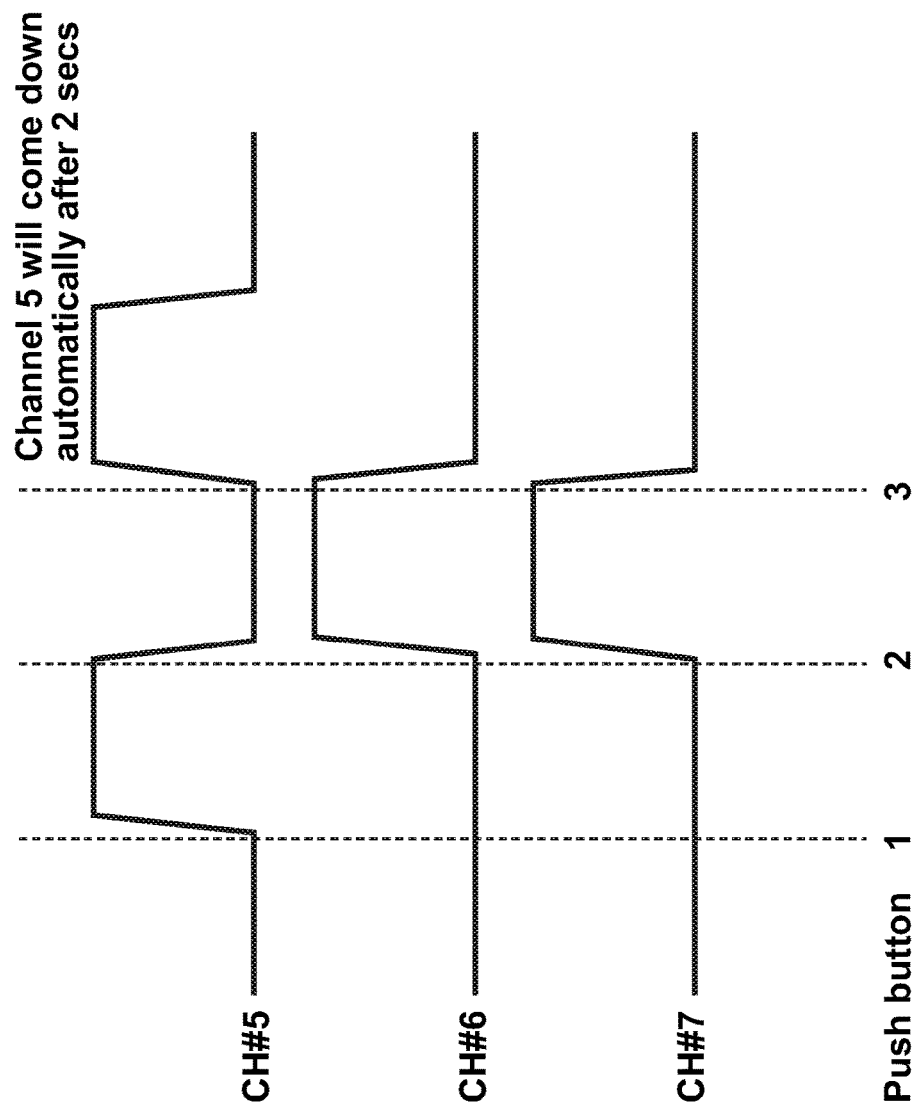

The protocol progression was shown, for the 3 steps of the protocol, in FIG. 50.

Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 5-7

Placement of the Electrodes—Muscles that May be Stimulated:
  Channel 5 was used to produce hand opening, Channels 6 and 7 were used to produce pulp to pulp pinch where Channel 6 was used to produce flexion of the index finger and Channel 7 was used to produce opposition of the thumb.
    Channel 5 was used to produce hand opening and stimulated the long finger extensors, i.e., extensor digitorum communis and was placed over the dorsal aspect of the forearm.
    Channel 6 was used to produce flexion of the index finger. This was achieved by either stimulating the 1$^{st}$ Lumbrical which resulted in flexion at the metacarpophalangeal and extension at the interphalangeal of the index finger or alternatively by stimulating the lateral part of Flexor Digitorum Superficialis which resulted in index finger metacarpophalangeal joint and interphalangeal joint flexion.
    Channel 7 was used to produce opposition of the thumb and stimulated thumb oppositors, i.e., opponens pollicis brevis and can be placed either over the median nerve just proximal to the wrist joint or over the Thenar eminence of the hand.

Program:
  Push button 1: (a) Channel 5 was activated—finger extension, i.e., hand opening
  Push button 2: (b) Channel 5 was decreased and Channels 6-7 were activated simultaneously bringing the index finger in flexion and the thumb in opposition to the index finger.

Push button 3: (c) Channels 6-7 were decreased and simultaneously Channel 5 was activated, staying activated for 2 sec and will then decrease—This produced hand opening for 2 seconds and relaxation of the arm The protocol was repeated as necessary or desired.

The subsequent push of the push button will initiate the sequence as discussed at the beginning of the paragraph, i.e., it will start with Push button 1 (a).

Type of Movement Produced: (a) Index finger flexion along with thumb opposition, and (b) followed by finger relaxation and hand opening for 2 seconds and later hand relaxation.

Protocol 17a and 17b 17.a Pinch Grasp Using Thenar Eminence+Extensor Communis Opening—SCI (Close/Open)

17.b Pinch Grasp Using Median Nerve+Extensor Communis Opening—SCI (Close/Open)

In this protocol smaller objects are manipulated using this type of grip like a pencil or a dice (by stimulating flexor digitorum superficialis) or a peg (by stimulating the dorsal interossei) etc.

For this protocol, placement of electrode for the 1$^{st}$ Lumbrical muscle is shown in FIG. 46. Electrode 178 is placed over the dorsal aspect of the 1$^{st}$ phalanx of the index finger (Channel 6) and is the delivery electrode. Electrode size is 2×1 cm$^2$. Placement of electrodes for Opponens Pollicis is shown in FIG. 47. 180 is the 5×5 cm$^2$ return electrode for 1$^{st}$ Lumbrical muscle and Opponens Pollicis Brevis muscle (channels 6 and 7. 182 is the delivery electrode for Opponens Pollicis Brevis (channel 7). Electrode size is 2.5 cm diameter. An alternate position for electrode 178 is shown in FIG. 48 as 184. Placement of electrodes for Extensor Digitorum Communis can be seen as FIG. 49, with 186 the 5×5 cm$^2$ delivery electrode for channel 5. 188 is the 5×5 cm$^2$ return electrode for channel 5.

Figure 51:
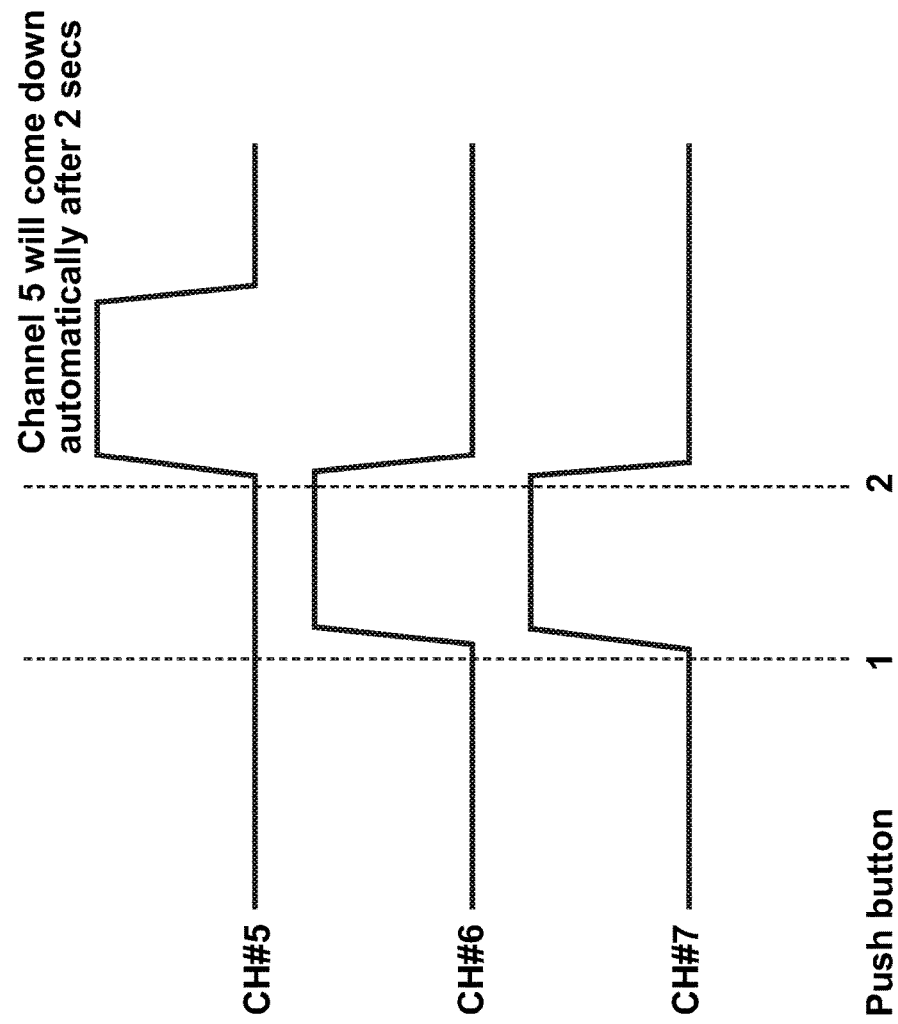

The protocol progression was shown, for the 2 steps of the protocol, in FIG. 51.

Parameters and protocol progression were as follows:
Parameters:
Pulse Duration: 400 μsec
Max Amplitude: 30 mA (the amplitude range can be much smaller pending which stimulator is used)
Ramp time: Ramp up 1 sec and ramp down 0.5 sec
Pulse frequency: 40 Hz
Channels used: Channels 5-7
Placement of the Electrodes—Muscles that May be Stimulated:

Channel 5 was used to produce hand opening, Channels 6 and 7 were used to produce pulp to pulp pinch where channel 6 was used to produce flexion of the index finger and channel 7 was used to produce opposition of the thumb.

Channel 5 was used to produce hand opening and stimulated the long finger extensors, i.e., extensor digitorum communis and was placed over the dorsal aspect of the forearm.

Channel 6 was used to produce flexion of the index finger. This was achieved by either stimulating the 1$^{st}$ Lumbrical which resulted in flexion at the metacarpophalangeal and extension at the interphalangeal of the index finger or alternatively by stimulating the lateral part of Flexor Digitorum Superficialis which resulted in index finger metacarpophalangeal joint and interphalangeal joint flexion.

Channel 7 was used to produce opposition of the thumb and stimulated thumb oppositors, i.e., opponens pollicis brevis and could be placed either over the median nerve just proximal to the wrist joint or over the Thenar eminence of the hand.

Program:
Before pressing a push button the patient was directed to place their hand around the object he/she wanted to grasp. Once the hand and fingers were in passive grasp position, the protocol progressed.

Push button 1: (a) Channels 6-7 were activated simultaneously, bringing the index finger in flexion and the thumb in opposition to the index finger.

Push button 2: (b) Channels 6-7 were decreased and simultaneously Channel 5 was activated, stayed activated for 2 sec and then decreased—This produced hand opening for 2 seconds and relaxation of the arm The protocol was repeated as necessary or desired.

The subsequent push of the push button will initiate the sequence as discussed at the beginning of the paragraph, i.e., it will start with Push button 1 (a).

Type of Movement Produced: (a) Index finger flexion along with thumb opposition, and (b) followed by finger relaxation and hand opening for 2 seconds and later hand relaxation.

Protocol 18—Hand Opening and Lumbrical Grip

This protocol was used to train for decreasing finger flexor tone in the hand and for grasping and manipulating objects using a lumbrical grip e.g. grasping and manipulating a book.

Figure 52:
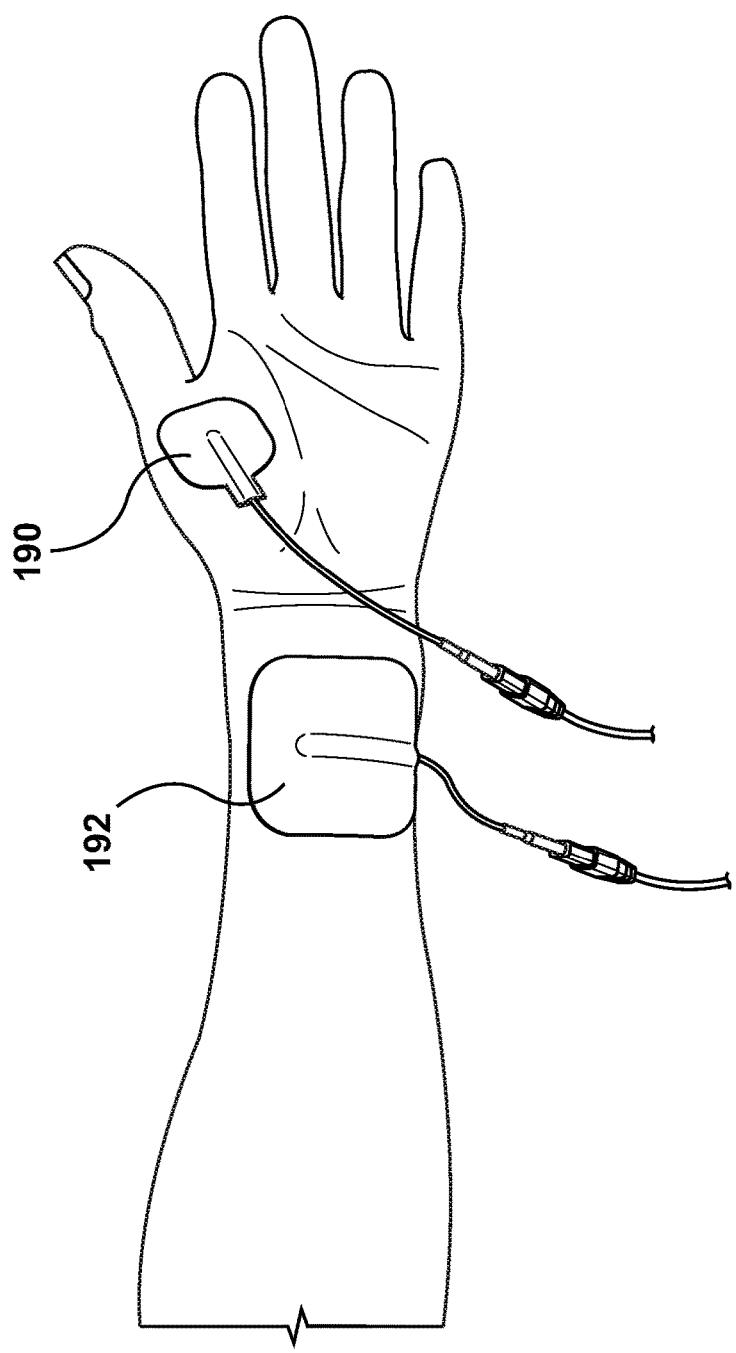
Figure 53:
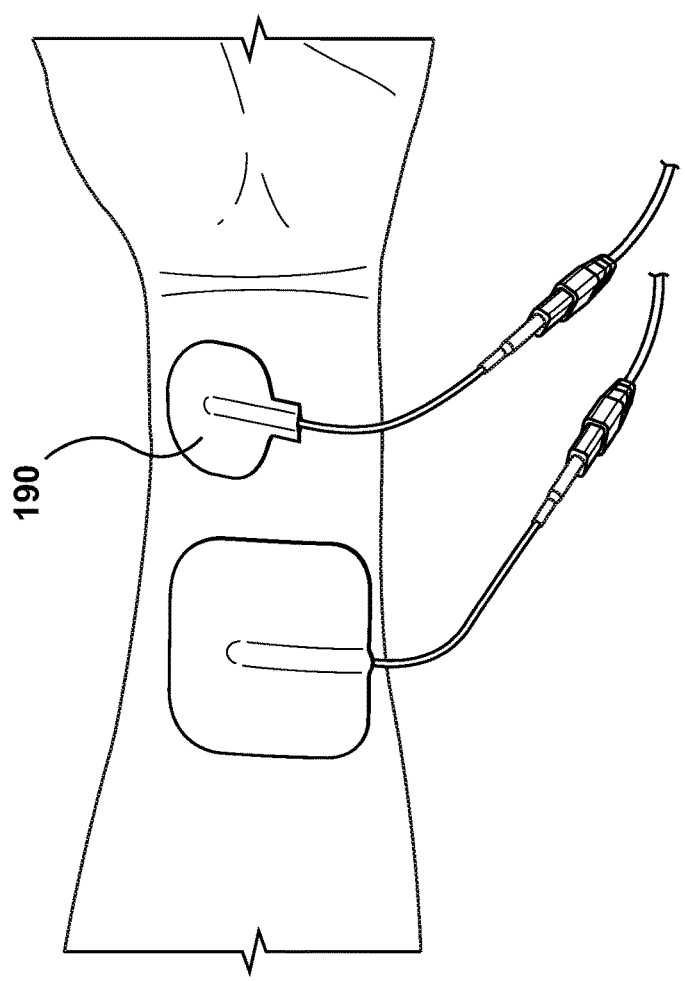

For this protocol, placement of electrode for Opponens Pollicis Brevis was shown in FIG. 52. 190 shows the 2.5 cm diameter cathode (delivery electrode) for Opponens Pollicis Brevis, i.e. Channel #4. 192 shows the 5×5 cm$^2$ anode (return electrode) for Channel 4. Alternate placement for 190 is shown in FIG. 53.

Figure 54:
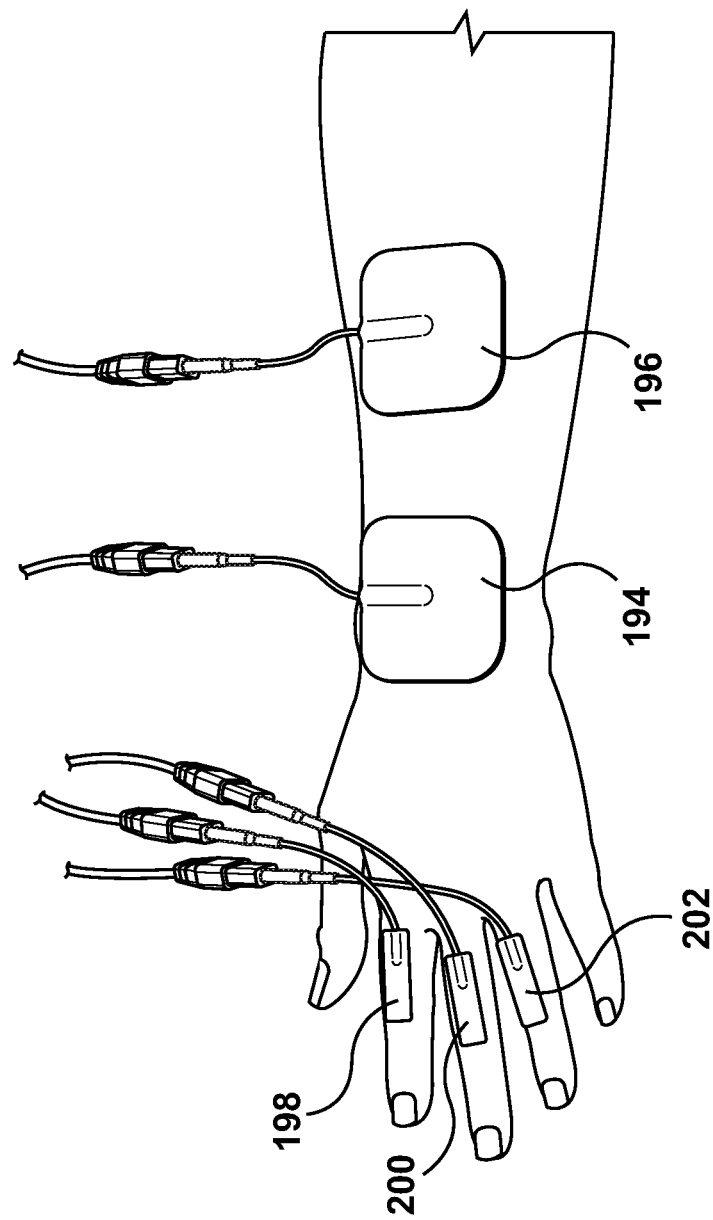

Placement of electrodes for Extensor Digitorum communis, Extensor carpi radialis, Extensor carpi ulnaris and 1$^{st}$-3$^{rd}$ Lumbrical muscles is shown in FIG. 54. 194 is the 5×5 cm$^2$ cathode (delivery electrode) for Extensor Digitorum communis, Extensor carpi radialis, Extensor carpi ulnaris, i.e. channel 5. 196 is the 5×5 cm$^2$ anode (return electrode) for Channels 5-8. 198, 200 and 202 are the cathode (delivery electrodes) for 1$^{st}$, 2$^{nd}$ and 3$^{rd}$ Lumbrical muscles, respectively, i.e. channels 6, 7 and 8 respectively. Electrode size is 2×1 cm$^2$.

Figure 55:
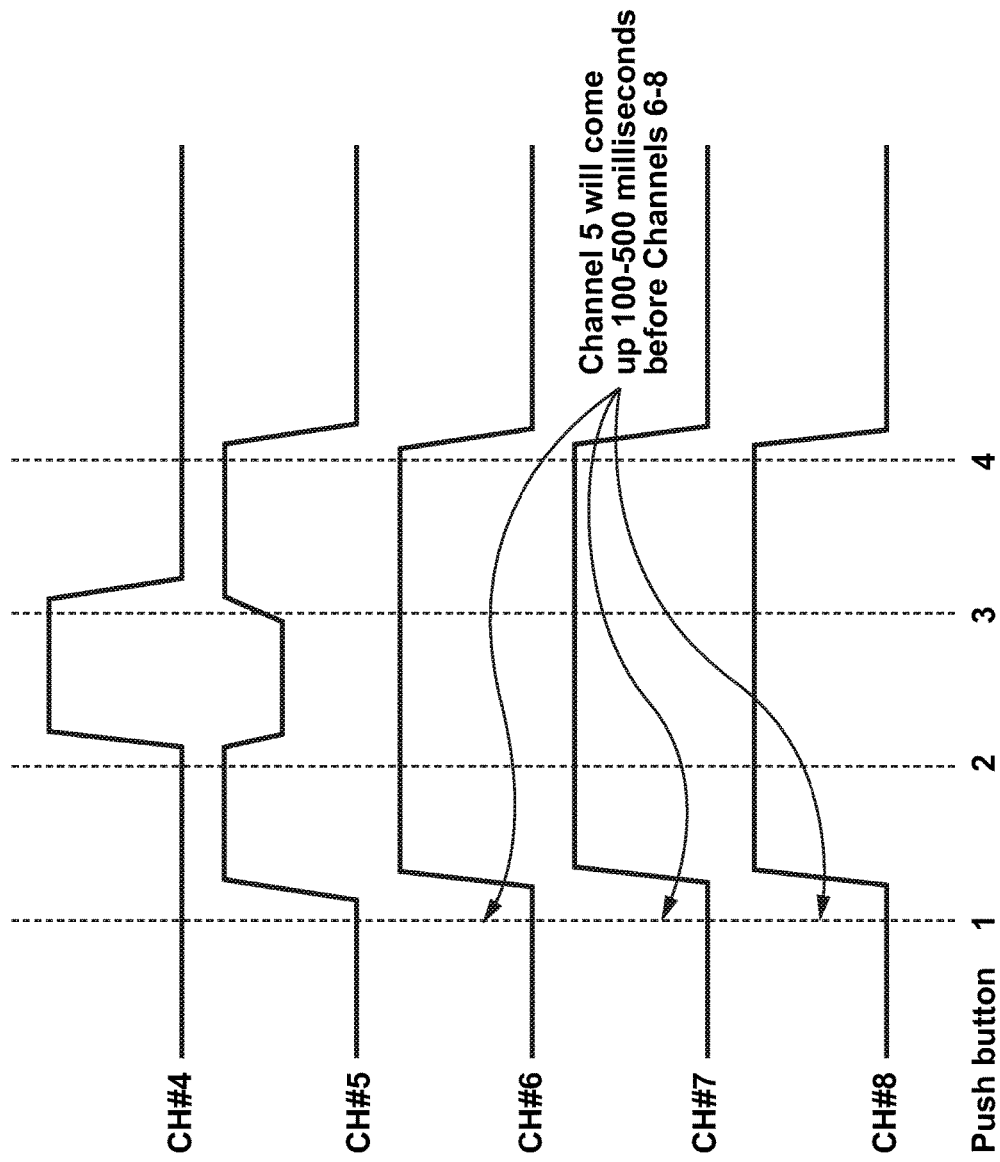

The protocol progression was shown, for the 4 steps of the protocol, in FIG. 55.

Parameters and protocol progression were as follows:
Parameters:
Pulse Duration: 400 μsec
Max Amplitude: 30 mA (the amplitude range can be much smaller pending which stimulator is used)
Ramp time: Ramp up 1 sec and ramp down 0.5 sec
Pulse frequency: 40 Hz
Channels used: Channels 4-8
Placement of the Electrodes—Muscles that May be Stimulated:

Channel 4 was used to place thumb in opposition. Channels 5-8 were used to stimulate wrist and finger extension/flexion muscles in the palm.

Channel 4 stimulated thumb opposition, i.e., thenar eminence of the hand, or on the ventral aspect of the forearm just proximal to the wrist to stimulate the opponens pollicis.

Channel 5 stimulated wrist and finger extensors, i.e. extensor digitorum communis and/or extensor digitorum, extensors carpi radialis, and extensor carpi ulnaris. Channel 5 starts 100-500 milliseconds before Channels 6-8.

Channel 6-8 stimulated the lumbrical muscles to allow finger extension and flexion at the IP joints, i.e., lumbrical muscles (I, II, III, and IV), electrodes will be placed over dorsal aspect of the first phalanx of index, middle and ring finger.

Program:

Push button 1: (a) Channel 5 was activated and 100-500 milliseconds later Channels 6-8 are activated—This activated finger extensors following which lumbrical muscles were activated to produce full finger extension with fanning.

Push button 2: (b) Simultaneously, Channel 5 was decreased to ½ or ⅓ of the initial stimulation pulse duration and Channel 4 was activated, while Channels 6-8 were constantly active—As the wrist and finger extension comes down the lumbrical stimulation generated lumbrical L-shape flexion. At the same time the thumb was placed in opposition Push button 3: (c) Channel 4 was decreased and Channel 5 was increased (back to full amplitude), while Channels 6-8 were constantly active—This relaxed the thumb and activated finger extensors with lumbrical muscles that produced full finger extension with fanning.

Push button 4: (d) Channels 5-8 were decreased—The hand moved to a relax state.

The protocol was repeated as necessary or desired.

The subsequent push of the push button will initiate the sequence as discussed at the beginning of the paragraph, i.e., it will start with Push button 1 (a).

Type of Movement Produced: Hand opening and hand closing (Lumbrical Grasp).

Protocol 19a and 19b—

19.a Lumbrical and Extensor Communis Opening+Lumbrical Grip+Palmar Grasp Using Thenar Eminence 19.b Lumbrical and Extensor Communis Opening+Lumbrical Grip+Palmar Grasp Using Median Nerve This protocol was used to train for decreasing finger flexor tone in the hand and for grasping and manipulating objects using a lumbrical grip e.g. grasping and manipulating a book.

For this protocol, electrode placement for Flexor Digitorum Superficialis and Profundus muscle and Median nerve for Opponens Pollicis Brevis can be seen in FIG. 39. 166 and 168 are the 2.5 cm diameter cathode (delivery electrode) for Flexor Digitorum Superficialis and Profundus, i.e. channel 2 and channel 3. 172 is the 2.5 cm diameter cathode (delivery electrode) for the Median nerve, i.e. channel 4. 170 is the anode for channels 2, 3, and 4 and electrode size is 5×5 cm². Alternate placement for 172 can be shown at FIG. 40.

Placement of electrodes for Extensor Digitorum communis, Extensor carpi radialis, Extensor carpi ulnaris and $1^{st}$-$3^{rd}$ Lumbrical muscles is shown in FIG. 54. 194 is the 5×5 cm² cathode (delivery electrode) for Extensor Digitorum communis, Extensor carpi radialis, Extensor carpi ulnaris i.e. channel 5. 196 is the 5×5 cm² anode (return electrode) for Channels 4-7. 198, 200 and 202 are the 2×1 cm² cathode (delivery electrodes) for $1^{st}$, $2^{nd}$ and $3^{rd}$ Lumbrical muscles, respectively, i.e. channels 6, 7 and , respectively.

Figure 56:
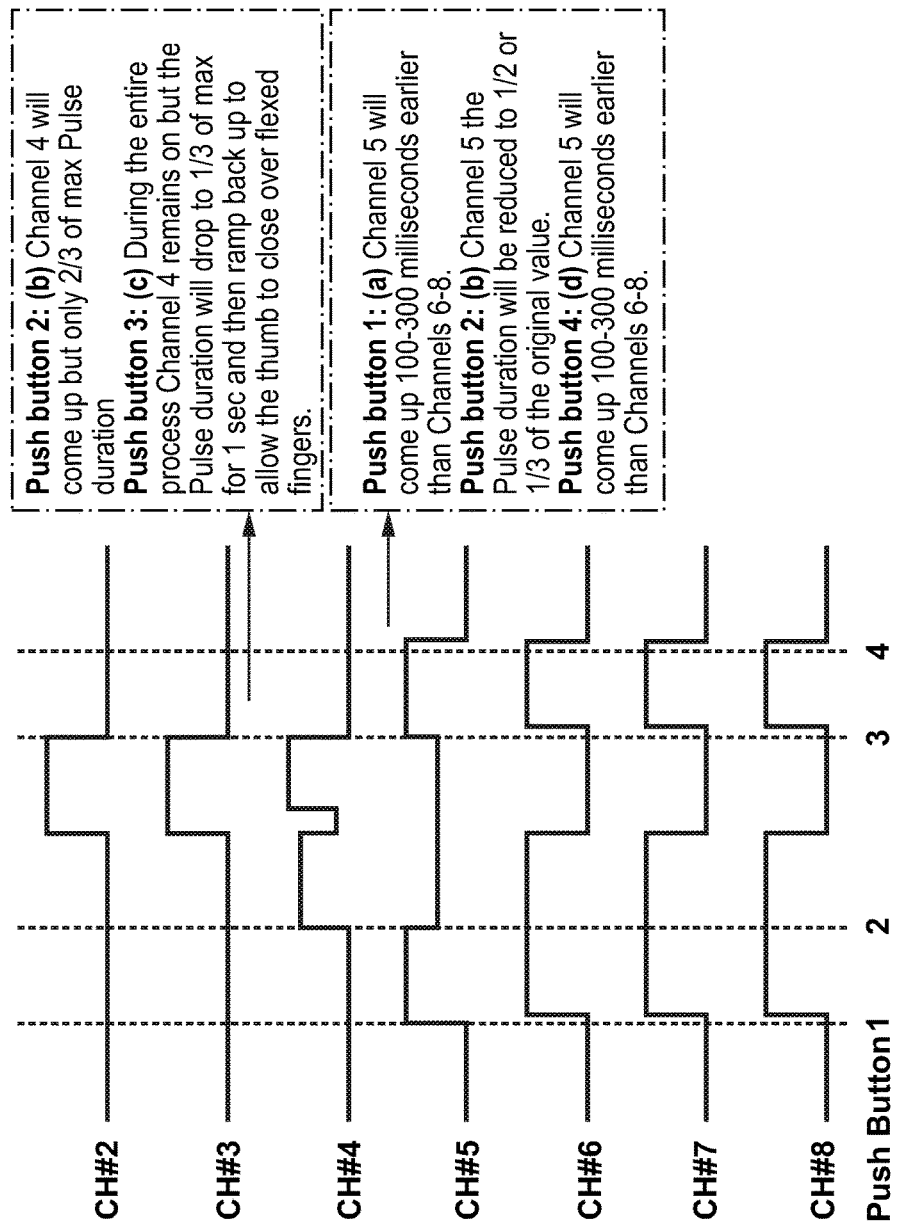

The protocol progression was shown, for the 4 steps of the protocol, in FIG. 56.

Parameters and protocol progression were as follows:

Parameters:
Pulse Duration: 400 μsec
Max Amplitude: 30 mA (the amplitude range can be much smaller pending which stimulator is used)
Ramp time: Ramp up 1 sec and ramp down 0.5 sec
Pulse frequency: 40 Hz
Channels used: Channels 2-8

Placement of the Electrodes—Muscles that May be Stimulated:

Channels 2 and 3 were used to stimulate finger flexors. Channel 4 was used to place thumb in opposition. Channels 5-8 was used to stimulate wrist and finger extension/flexion muscles in the palm.

Channels 2 and 3 stimulated finger flexors, i.e., flexor digitorum superficialis and flexor digitorum profundus.

Channel 4 was used to produce opposition of the thumb and stimulated thumb oppositors, i.e., opponens pollicis brevis and could be placed either over the median nerve just proximal to the wrist joint or over the Thenar eminence of the hand.

Channel 5 stimulated wrist and finger extensors, i.e., extensor digitorum communis and/or extensor digitorum, extensors carpi radialis, and extensor carpi ulnaris. Channel 5 started 100-500 milliseconds before Channels 6-8.

Channels 6-8 stimulated the lumbrical muscles to allow finger extension and flexion at the IP joints, i.e., lumbrical muscles (I, II, III, and IV), electrodes were placed over dorsal aspect of the first phalanx of index, middle and ring finger.

Program:

Push button 1: (a) Channel 5 was activated and 100-500 milliseconds later Channels 6-8 were activated—This, in turn, activated finger extensors following which lumbrical muscles were activated to produce full finger extension with fanning.

Push button 2: (b) Simultaneously, for Channel 5 the Pulse duration was reduced by about ⅓ to ½ and Channel 4 was activated, but with only about ⅔ of its maximum pulse duration—As the wrist and finger extensions came down the lumbrical stimulation generated lumbrical L-shape flexion. At the same time the thumb was placed in gentle opposition.

The moment lumbrical L-shape flexion was reached, (after 1 second) Channels 5-8 were reduced and Channels 2 and 3 activated and simultaneously Channel 4 ramped up from ⅔ to maximum Pulse duration to allow the thumb to close over flexed fingers. Lumbrical muscles were not activated by the FES anymore but the flexor digitorum superficialis and flexor digitorum profundus contracted to generate full finger flexion.

Push button 3: (c) Channels 2-4 were reduced. Channel 5 was increased and 100-500 milliseconds later Channels 6-8 were increased—This relaxed thumb and finger flexors, immediately after that, finger extensors were active, following which lumbrical muscles were activated to produce full finger extension with fanning.

Push button 4: (d) Channels 5-8 were reduced and the hand relaxed.

The protocol was repeated as necessary or desired.

The subsequent push of the push button will initiate the sequence as discussed at the beginning of the paragraph, i.e., it will start the protocol from Push button 1 (a).

Type of Movement Produced: Hand opening and hand closing (Palmar+Lumbrical Grasp)

Note: In stroke patients it was determined that the time period between Push button 2 and Push button 4 events should be short—just sufficient that the grasp was executed properly for 10-15 seconds, and not longer than that. This was used to decrease finger flexors' tone. Emphasis in this protocol with stroke subjects was on hand opening. In other words Push button 4 to Push button 5 time period and Push button 1 to Push button 2 were long (30-40 seconds or longer).

Protocol 20—Extensor Communis Opening+Tripod Grasp Using Thenar Eminence—Late SCI and Stroke (Open/Close/Open).

This protocol was used to train on manipulation of smaller objects using this type of grip, such as a pencil or a larger diameter peg. The protocol may be used to train functional activities such as writing.

Figure 57:
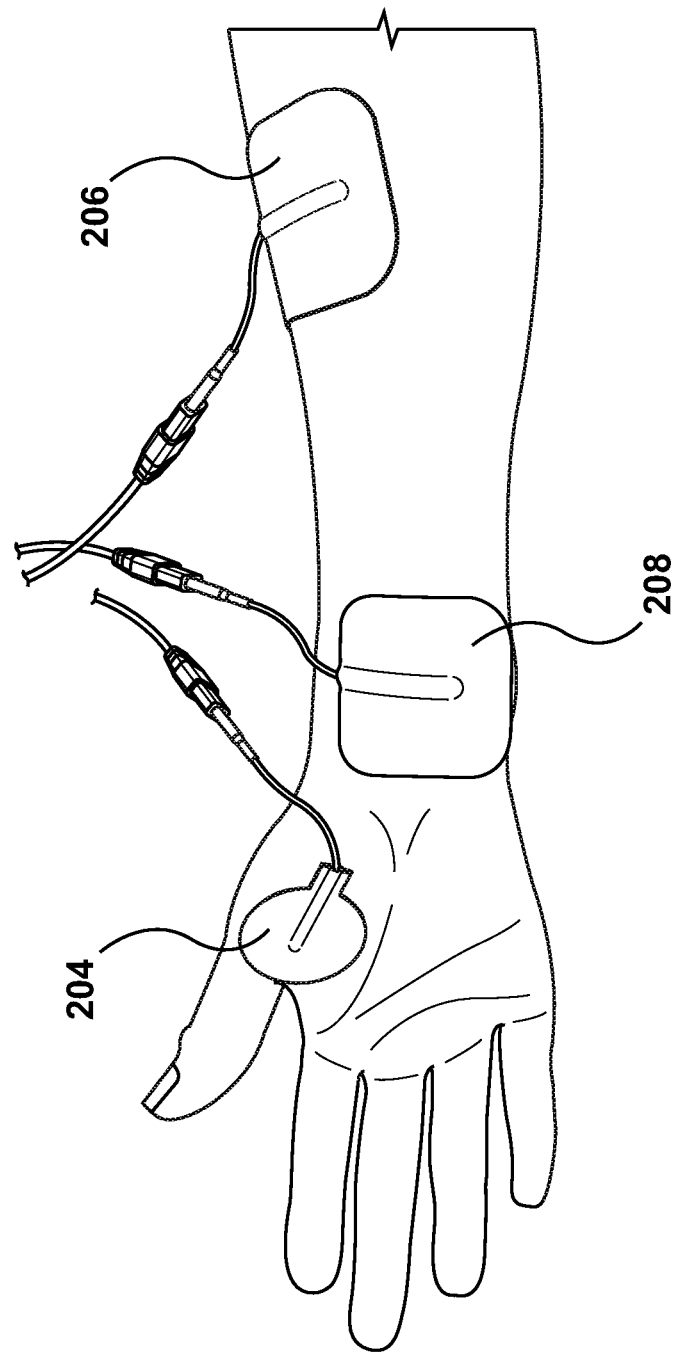

For this protocol, Placement of electrodes for Opponens Pollicis Brevis and Flexor Digitorum Superficialis muscles is shown in FIG. 57. 204 is the 2.5 diameter cathode, i.e. the delivery electrode for Opponens Pollicis Brevis muscle, i.e. Channel 8. 206 is the 5×5 cm$^2$ cathode, i.e. the delivery electrode for Flexor Digitorum Superficialis, i.e. Channel 6. 208 is the 5×5 cm$^2$ anode, i.e. the return electrode for Channels 6-8.

Figure 58:
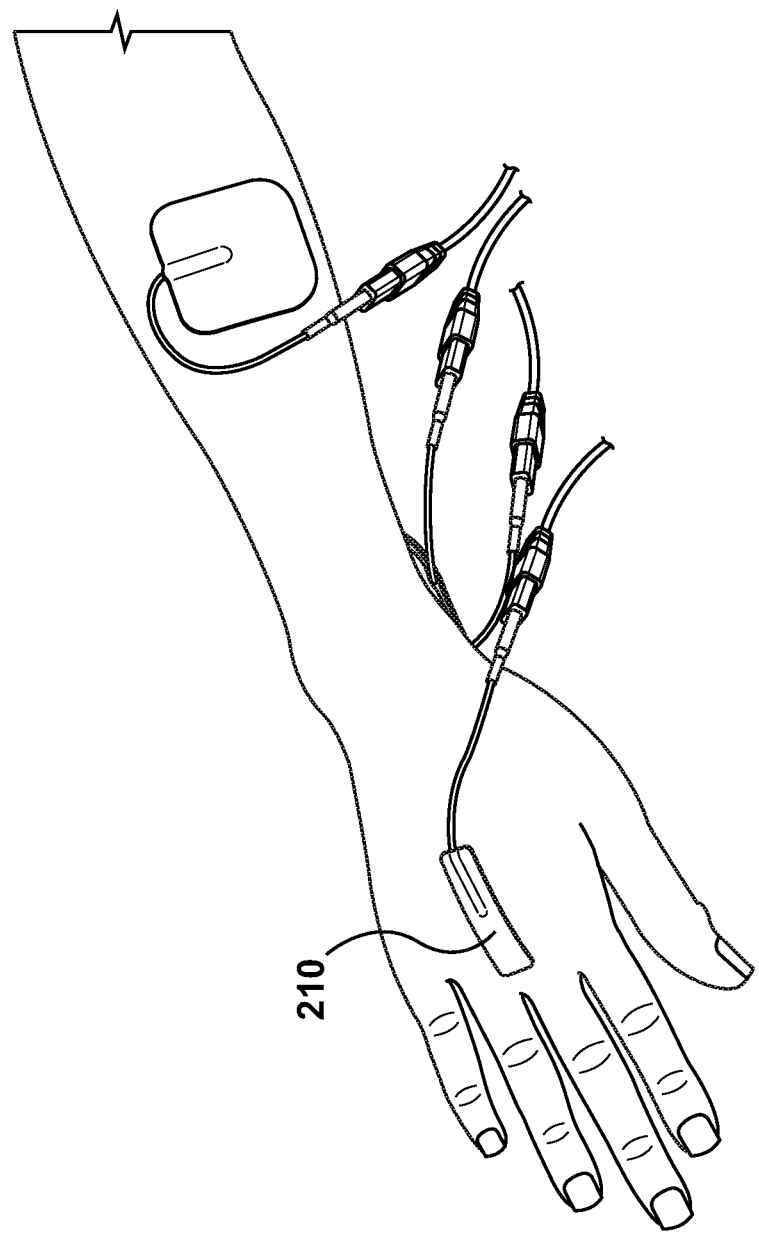

Placement of electrode for the 2$^{nd}$ dorsal interrosseous muscle is shown in FIG. 58. 210 is the 2×1 cm$^2$ cathode, i.e. the delivery electrode for the 2$^{nd}$ dorsal interrosseous muscle, i.e. Channel 7.

Figure 49:
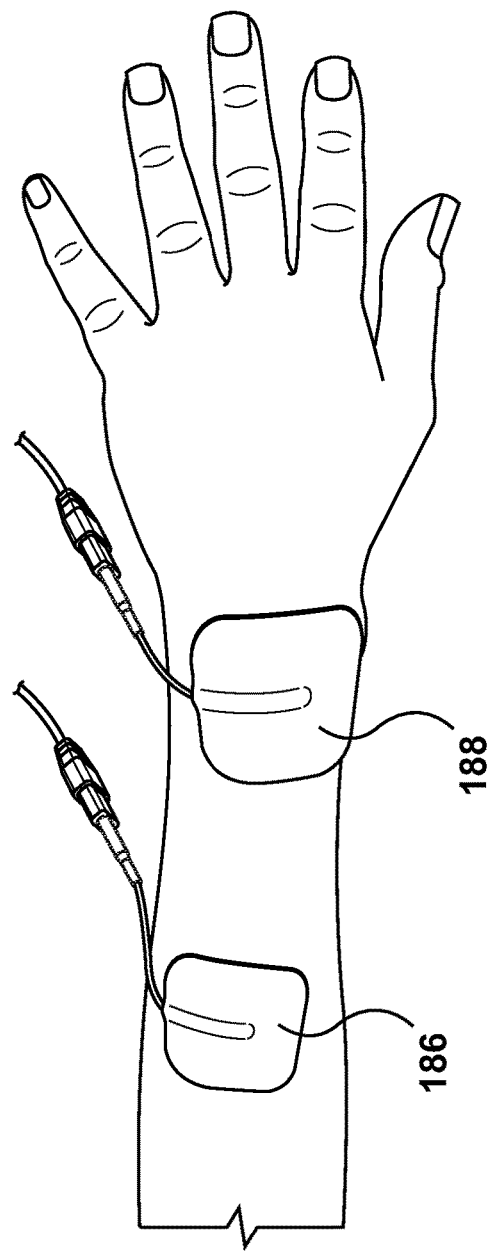

Placement of electrodes for Extensor Digitorum Communis can be seen as FIG. 49, with 186 the 5×5 cm$^2$ delivery electrode for channel 5. 188 is the 5×5 cm$^2$ return electrode for channel 5.

Figure 59:
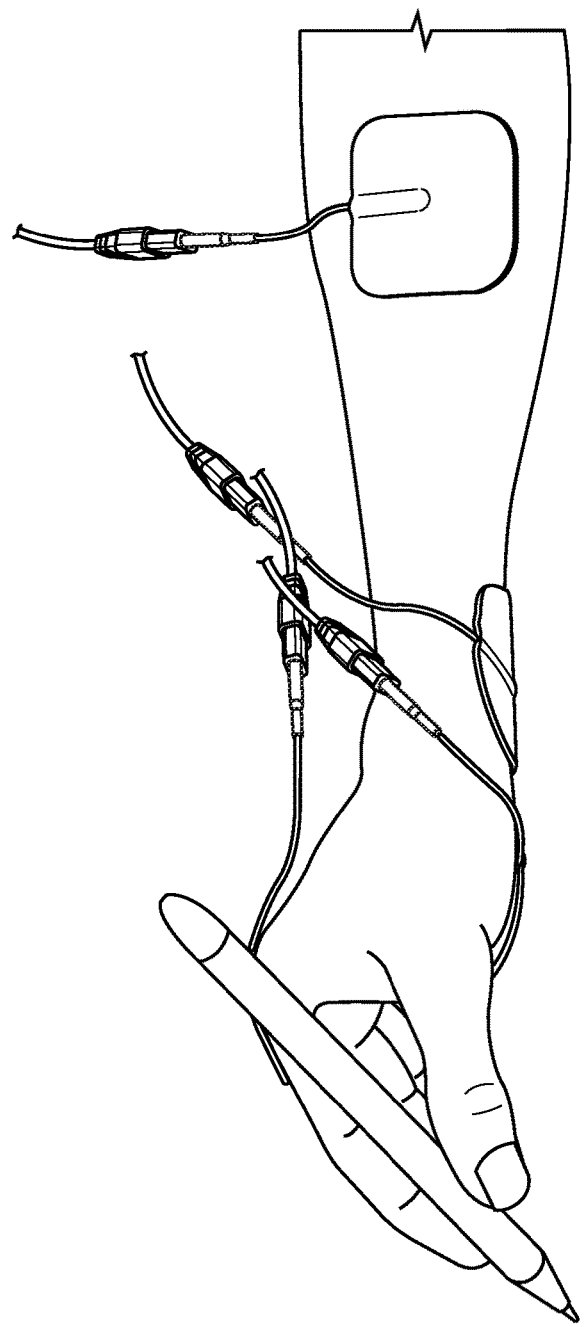

FIG. 59 shows the tripod grip.

Figure 60:
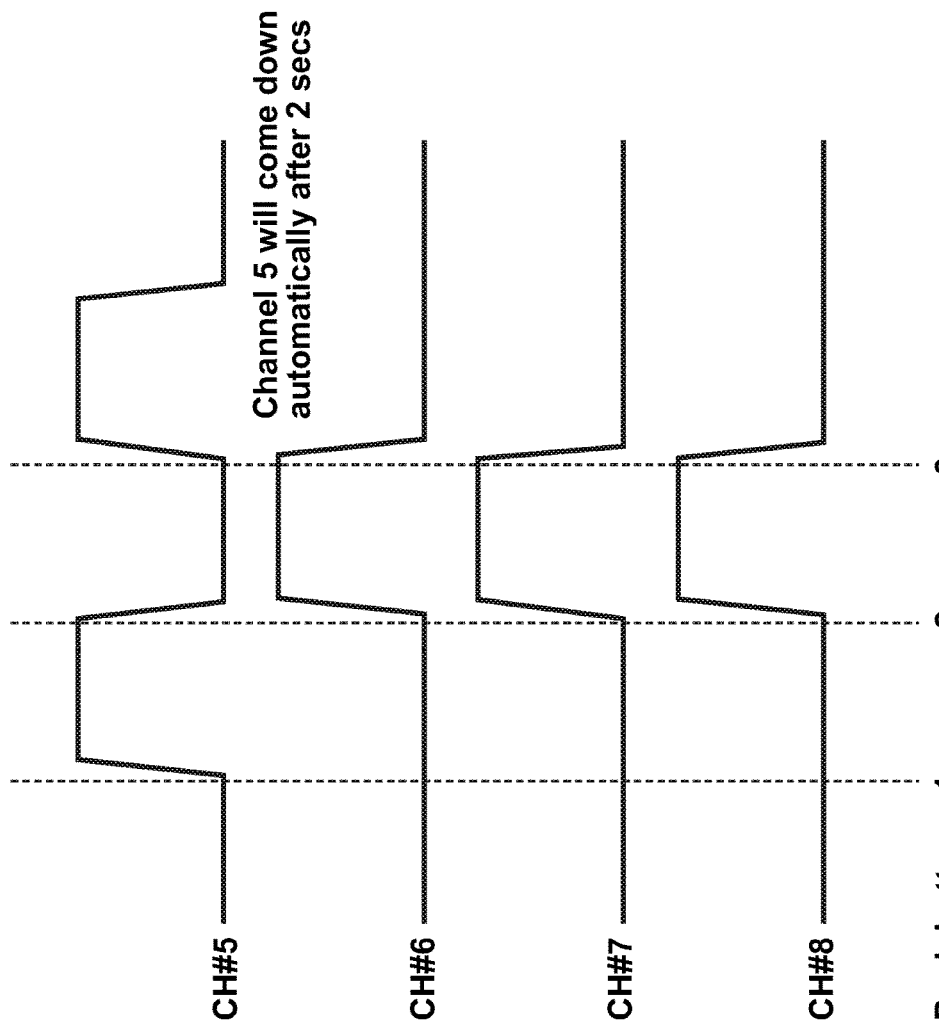

The protocol progression was shown, for the 3 steps of the protocol, in FIG. 60.

Parameters and protocol progression were as follows:
Parameters:
 Pulse Duration: 400 μsec
 Max Amplitude: 30 mA (the amplitude range can be much smaller pending which stimulator is used)
 Ramp time: Ramp up 1 sec and ramp down 0.5 sec
 Pulse frequency: 40 Hz
 Channels used: Channels 5-8
Placement of the Electrodes—Muscles that May be Stimulated:
 Channel 5 was used to produce hand opening, Channels 6-8 were used to produce a tripod grip where Channel 6 is used to produce flexion of the index and middle finger, Channel 7 was used to bring the middle finger in contact with the index finger and Channel 8 was used to produce opposition of the thumb against the flexed index and middle finger.
  Channel 5 was used to produce hand opening and stimulated the long finger extensors, i.e., extensor digitorum communis and was placed over the dorsal aspect of the forearm.
  Channel 6 was used to produce flexion of the index and middle finger and stimulated the lateral portion of the Flexor Digitorum Superficialis and was placed over the ventral aspect of the forearm.
  Channel 7 was used to bring the middle finger in contact with the index finger and stimulated the 2$^{nd}$ dorsal interrosseous muscle and was placed over the dorsal aspect of the hand.
  Channel 8 was used to bring the thumb in opposition to the flexed index and middle finger and stimulated Opponens Pollicis Brevis and was placed either on the Thenar eminence of the hand.

Program:
 Push button 1: (a) Channel 5 was activated—finger extension, i.e., hand opening
 Push button 2: (b) Channel 5 was reduced and Channels 6-8 was activated, simultaneously bringing the index and middle finger in flexion and in contact with one another and the thumb in opposition to the flexed fingers.
 Push button 3: (c) Channels 6-8 were reduced and simultaneously Channel 5 was activated, stay contracted for 2 sec and was then reduced—This produces hand opening for 2 seconds followed by relaxation of the hand.

The protocol was repeated as necessary or desired.

The subsequent push of the push button will initiate the sequence as discussed at the beginning of the paragraph, i.e., it will start with Push button 1 (a).

Type of Movement Produced: (a) Index and middle finger flexion and approximation along with thumb opposition, and (b) followed by finger relaxation and hand opening for 2 seconds and later hand relaxation.

Protocol 21—Two Finger Lateral Pinch

This protocol was used to train for holding and manipulating thinner objects such as cigarettes, credit cards, paper, etc., using a lateral pinch grip.

Figure 61:
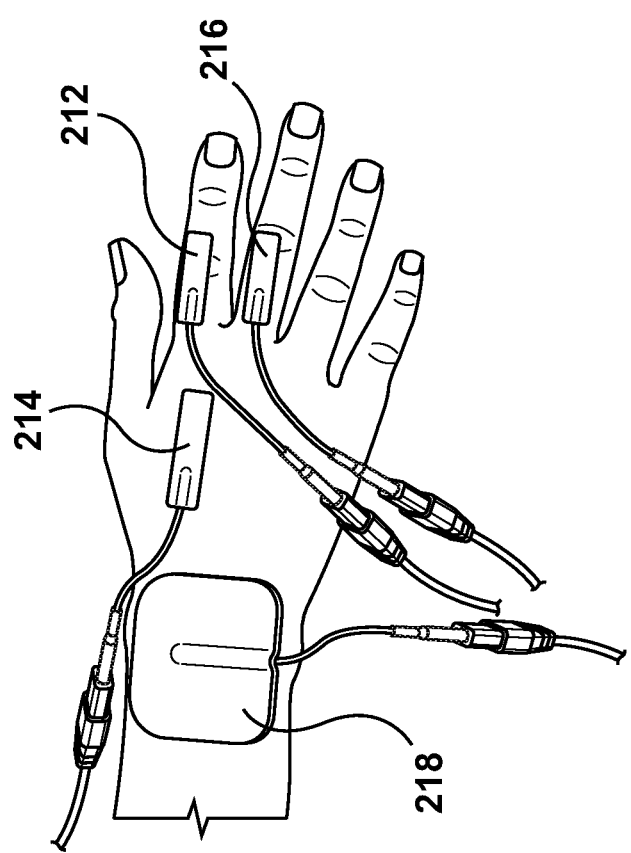

For this protocol, Placement of electrodes for 1$^{st}$ and 2nd Lumbrical muscles and 2$^{nd}$ Dorsal interrosseous muscle is shown in FIG. 61. 214 is the 2×1 cm$^2$ cathode, i.e. the delivery electrode for the 2$^{nd}$ Dorsal Interrosseous muscle (Channel 8). 212 is the 2×1 cm$^2$ cathode, i.e. the delivery electrode for the 1$^{st}$ Lumbrical muscle (Channel 6). 216 is the 2×1 cm$^2$ cathode, i.e. the delivery electrode for the 2$^{nd}$ Lumbrical muscle (Channel 7). 218 is the 5×5 cm$^2$ anode, i.e. the return electrode for Channels 5-8.

Placement of electrodes for Extensor Digitorum Communis can be seen as FIG. 49, with 186 the 5×5 cm$^2$ delivery electrode for channel 5. 188 is the 5×5 cm$^2$ return electrode for channel 5.

Figure 62:
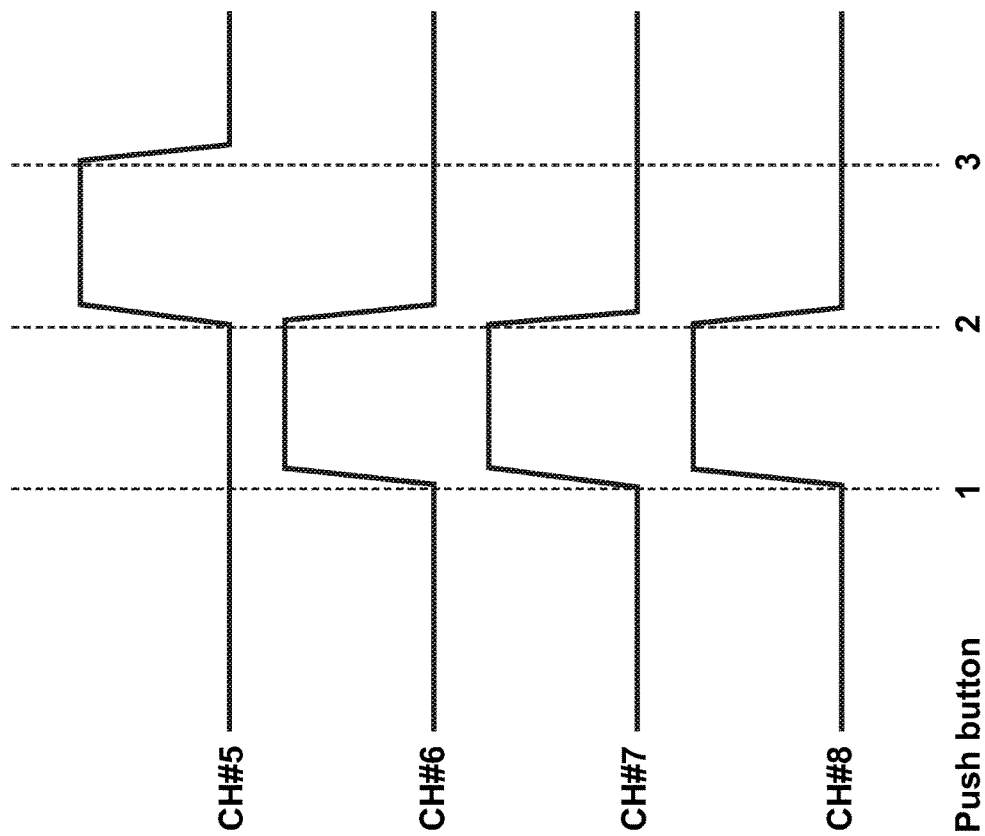

The protocol progression was shown, for the 3 steps of the protocol, in FIG. 62.

Parameters and protocol progression were as follows:
Parameters:
 Pulse Duration: 400 μsec
 Max Amplitude: 30 mA (the amplitude range can be much smaller pending which stimulator is used)
 Ramp time: Ramp up 1 sec and ramp down 0.5 sec
 Pulse frequency: 40 Hz
 Channels used: Channels 5-8
Placement of the Electrodes—Muscles that May be Stimulated:
 Channel 5 was used to produce hand opening, Channels 6-8 were used to produce two finger lateral pinch grip where Channels 6 and 7 were used to produce index and middle finger metacarpophalangeal flexion and interphalangeal extension and stimulated 1$^{st}$ and 2$^{nd}$ Lumbrical muscles and Channel 8 was used to bring the index and middle finger in contact with one another and stimulated the 2$^{nd}$ dorsal interrosseous muscle.
  Channel 5 was used to produce hand opening and stimulated the long finger extensors, i.e., extensor digitorum communis and will be placed over the dorsal aspect of the forearm.
  Channel 6 was used to produce flexion of the index finger at the metacarpophalangeal joint and extension at the interphalangeal joint and stimulated the 1$^{st}$ Lumbrical muscle and was placed over the dorsal aspect of the first phalanx of the index finger.

Channel 7 was used to produce flexion of the middle finger at the metacarpophalangeal joint and extension at the interphalangeal joint and stimulated the $2^{nd}$ Lumbrical muscle and was placed over the dorsal aspect of the first phalanx of the middle finger.

Channel 8 was used to approximate the index and middle fingers and stimulated the $2^{nd}$ dorsal interrosseous muscle and was placed over the dorsum of the hand.

Program:

Push button 1: (a) Channels 6-8 were activated simultaneously bringing the index and middle finger in flexion at the metacarpophalangeal joints and in extension at the interphalangeal joints and in contact with one another.

Push button 2: (b) Channels 6-8 were reduced and simultaneously Channel 5 was activated—finger extension, i.e., hand opening.

Push button 3: (c) Channel 5 was reduced and the hand moved back to a relaxed state.

The protocol was repeated as necessary or desired.

The subsequent push of the push button will initiate the sequence as discussed at the beginning of the paragraph, i.e., it will start with Push button 1 (a).

Type of Movement Produced: (a) Index and middle finger flexion at the MCP and extension at the IP, and (b) followed by complete hand opening (c) followed by hand relaxation.

Protocols 22a and 22b 22.a Palmar Grasp Using Thenar Eminence+Lumbrical and Extensor Communis Opening 22.b Palmar Grasp Using Median Nerve+Lumbrical and Extensor Communis Opening This protocol was used to decrease finger flexor tone in the hand and to grasp and manipulate objects using a palmar grip, e.g. a book or a pop can.

For this protocol, electrode placement for Flexor Digitorum Superficialis and Profundus muscle and Median nerve for Opponens Pollicis Brevis can be seen in FIG. 39. 166 and 168 are the 2.5 diameter cathode (delivery electrode) for Flexor Digitorum Superficialis and Profundus, i.e. channel 2 and channel 3. 172 is the 2.5 diameter cathode (delivery electrode) for the Median nerve, i.e. channel 4. 170 is the 5×5 cm² anode for Channels 2,3 and 4. Alternate placement for 172 can be shown at FIG. 40.

Placement of electrodes for Extensor Digitorum communis, Extensor carpi radialis, Extensor carpi ulnaris and $1^{st}$-$3^{rd}$ Lumbrical muscles is shown in FIG. 54. 194 is the 5×5 cm² cathode (delivery electrode) for Extensor Digitorum communis, Extensor carpi radialis, Extensor carpi ulnaris i.e. channel 5. 196 is the 5×5 cm² anode (return electrode) for Channels 4-7. 198, 200 and 202 are the 2×1 cm² cathode (delivery electrodes) for $1^{st}$, $2^{nd}$ and $3^{rd}$ Lumbrical muscles, respectively, i.e. channels 6, 7 and 8, respectively.

The protocol progression was shown, for the 4 steps of the protocol, in FIG. 63.

Parameters and protocol progression were as follows:

Parameters:

Pulse Duration: 400 μsec

Max Amplitude: 30 mA (the amplitude range can be much smaller pending which stimulator is used)

Ramp time: Ramp up 1 sec and ramp down 0.5 sec

Pulse frequency: 40 Hz

Channels used: Channels 2-8

Placement of the Electrodes—Muscles that May be Stimulated:

Channels 2 and 3 were used to stimulate finger flexors. Channel 4 was used to place thumb in opposition. Channels 5-8 were used to stimulate wrist and finger extension/flexion muscles in the palm.

Channels 2 and 3 stimulated finger flexors, i.e., flexor digitorum superficialis and flexor digitorum profundus.

Channel 4 was used to produce opposition of the thumb and stimulated thumb oppositor, i.e., opponens pollicis brevis and could be placed either over the median nerve just proximal to the wrist joint or over the Thenar eminence of the hand.

Channel 5 stimulated wrist and finger extensors, i.e., extensor digitorum communis and/or extensor digitorum, extensors carpi radialis, and extensor carpi ulnaris. Channel 5 started 100-500 milliseconds before Channels 6-8.

Channels 6-8 stimulated the lumbrical muscles to allow finger extension and flexion at the IP joints, i.e., lumbrical muscles (I, II, III, and IV), electrodes will be placed over dorsal aspect of the first phalanx of index, middle and ring finger.

Program:

Before pressing a push button the patient placed their hand around the object he/she wanted to grasp. This could be a passive, over the object sliding motion. Once the hand and fingers were in passive grasp position the protocol was initiated.

Push button 1: (a) Channels 2-4 were activated—The flexor digitorum superficialis and flexor digitorum profundus will contract to generate proper finger flexion. Finger flexion was accompanied by the thumb which was placed in opposition.

Push button 2: (b) Channels 2-4 were decreased. Channel 5 was activated and 100-500 milliseconds later Channels 6-8 were activated—This relaxed thumb and the finger flexors, immediately after that finger extensors were active, following which lumbrical muscles were activated to produce full finger extension with fanning.

Push button 3: (c) Channels -8 were decreased—The hand relaxed.

The protocol was repeated as necessary or desired.

The subsequent push of the push button will initiate the sequence as discussed at the beginning of the paragraph, i.e., it will start the protocol from Push button 1 (a).

Type of Movement Produced: Hand opening and hand closing (Finger flexion+Lumbrical hand opening).

Protocol 23a and 23b 23.a—BILATERAL Palmar Grasp Using Thenar Eminence+Extensor Communis Opening—SCI (Close/Open)

23.b—BILATERAL Palmar Grasp Using Median Nerve+Extensor Communis Opening—SCI (Close/Open)

The protocol was used to train for bilateral grasping of large and heavier objects such as pop cans, jars, books, tennis balls, etc.

For this protocol, electrode placement for Flexor Digitorum Superficialis and Profundus muscle and Median nerve for Opponens Pollicis Brevis can be seen in FIG. 39. 166 and 168 are the 2.5 diameter cathode (delivery electrode) for Flexor Digitorum Superficialis and Profundus i.e. channel 2 or 6 (one for each arm) and channel 3 or 7 (one for each arm). 172 is the 2.5 diameter cathode (delivery electrode) for the Median nerve, i.e. channel 4 or 8 (one for each arm). 170 is the 5×5 cm² anode for channels 2, 3, and 4, or, on the other hand, 6, 7, and 8. Alternate placement for 172 can be shown at FIG. 40.

Placement of electrodes for Extensor Digitorum communis, Extensor carpi radialis, Extensor carpi ulnaris muscles can be seen in FIG. 41. 174 is the 5×5 cm² cathode (delivery electrode) for Extensor Digitorum communis, Extensor carpi radialis, Extensor carpi ulnaris, i.e. channel 1 or 5 (one for each arm). 176 is the 5×5 cm² anode (return electrode) for Channel 1 or 5 (one for each arm).

Parameters and protocol progression were as follows:
Parameters:
  Pulse Duration: 400 μsec
  Max Amplitude: 30 mA (the amplitude range can be much smaller pending which stimulator is used)
  Ramp time: Ramp up 1 sec and ramp down 0.5 sec
  Pulse frequency: 40 Hz
  Channels used: Channels 1-4 for RIGHT HAND and Channels 5-8 for LEFT HAND Placement of the Electrodes—Muscles that May be Stimulated:
Right Hand:
  Channel 1 was used to produce RIGHT HAND opening, Channels 2 and 3 were used to produce RIGHT HAND finger flexion and Channel 4 was used to produce RIGHT HAND thumb opposition.
    Channel 1 was used to produce RIGHT HAND opening and stimulated the long finger extensors, i.e., extensor digitorum communis and was placed over the dorsal aspect of the forearm.
    Channels 2 and 3 were used to produce RIGHT HAND closing and stimulated long finger flexors, i.e., flexor digitorum superficialis and flexor digitorum profundus and were placed over the ventral aspect of the forearm.
    Channel 4 was used to produce opposition of the RIGHT HAND thumb and stimulated thumb oppositor, i.e., opponens pollicis brevis and could be placed either over the median nerve just proximal to the wrist joint or over the Thenar eminence of the hand.
Left Hand:
  Channel 5 was used to produce LEFT HAND opening, Channels 6 and 7 were used to produce LEFT HAND finger flexion and Channel 8 was used to produce LEFT HAND thumb flexion.
    Channel 5 was used to produce LEFT HAND opening and stimulated the long finger extensors, i.e., extensor digitorum communis and was placed over the dorsal aspect of the forearm.
    Channels 6 and 7 were used to produce LEFT HAND closing and stimulated long finger flexors, i.e., flexor digitorum superficialis and flexor digitorum profundus and were placed over the ventral aspect of the forearm.
    Channel 8 was used to produce opposition of the LEFT HAND thumb and stimulated thumb oppositor, i.e., opponens pollicis brevis and could be placed either over the median nerve just proximal to the wrist joint or over the Thenar eminence of the hand.

The potential electrode placement for Channels 1-4 and 5-8 are shown as described above. In order not to replicate figures both for left and right hand, the same figures can be used for both hands. Placement of the electrodes for Channel 1 is equivalent to electrode placement for Channel 5. Similarly Channels 2, 3 and 4 are equivalent to Channels 6, 7 and 8, respectively.
Program:
Right Hand (Push Button #1):
  Before pressing push button #1 the patient placed their hand around the object he/she wanted to grasp. This could be a passive, over or around the object sliding motion. Once the hand and fingers were in passive grasp position protocol was initiated.
    Push button #1—pressing 1: (a) Channels 2-4 were initiated simultaneously to produce palmar grip
    Push button #1—pressing 2: (b) Channels 2-4 decreased and simultaneously Channel 1 was initiated, stayed contracted for 2 sec and then decreased. This produces hand opening for 2 seconds and relaxation of the arm
  The subsequent push of the push button will initiate the sequence as discussed at the beginning of the paragraph, i.e., it will start with Push button #1—pressing 1 (a).
Left Hand (Push Button #2):
  Before pressing push button #2 the patient placed their hand around the object he/she wanted to grasp. This could be a passive, over or around the object sliding motion. Once the hand and fingers were in passive grasp position the protocol was initiated.
    Push button #2—pressing 1: (a) Channels 6-8 were initiated simultaneously to produce palmar grip
    Push button #2—pressing 2: (b) Channels 6-8 were decreased and simultaneously Channel 5 was initiated, stayed contracted for 2 sec and then decreased. This produces hand opening for 2 seconds and relaxation of the arm
  The subsequent push of the push button will initiate the sequence as discussed at the beginning of the paragraph, i.e., it will start with Push button #2—pressing 1 (a).
  Type of Movement Produced: (a) Bilateral but separate finger flexion combined with thumb opposition, and (b) followed by finger relaxation and hand opening for 2 seconds and later hand relaxation.
Protocol 24a-24b
  24.a BILATERAL Lateral Pinch Grasp Using Thenar Eminence+Extensor Communis Opening—SCI (Close/Open)
  24.b BILATERAL Lateral Pinch Grasp Using Median Nerve+Extensor Comunis Opening—SCI (Close/Open)
  Protocol 24a and 24b were identical to protocols 15a and 15b, except that the protocol was bilateral i.e. both hands were utilized, as described in protocol 23.

The invention claimed is:

1. A method for functional electrical stimulation therapy comprising the steps of:
  a. stimulating at least one finger extensor muscle;
  b. stimulating at least one lumbricalis muscle using an electrical pulse;
  c. relaxing at least one lumbricalis muscle; and
  d. relaxing at least one finger extensor muscle;
  wherein steps a-d are repeated at least 5 times.

2. The method of claim 1 further comprising a stimulation of at least one interossei muscle of the same hand.

3. The method of claim 1 further comprising stimulation of at least one thumb flexor muscle of the same hand.

4. The method of claim 1 further comprising stimulation of at least one dorsal interrosseous muscle of the same hand.

5. The method of claim 2 wherein the stimulation of the at least one lumbricalis muscle and the at least one interossei muscle comprises:
  placing at least one electrode on a proximal phalanx of a finger, proximal to a metacarpopharangeal joint, on said hand;
  placing return electrode on the proximal and posterior part of a wrist on said hand; and
  passing an electric current through the at least one electrode to the return electrode.

6. The method of claim 1 further comprising:
  e. relaxation of the at least one finger extensor muscle; and
  f. stimulation of the at least one finger extensor muscle;

wherein steps e. and f. are performed between steps b. and c. and accordingly repeated at least 5 times.

7. The method of claim 1 further comprising:
e. relaxation of the at least one finger extensor muscle;
f. stimulation of at least one finger flexor muscle;
g. relaxation of the at least one lumbricalis muscle;
h. stimulation of the at least one lumbricalis muscle;
i. relaxation of at least one finger flexor muscle; and
j. stimulation of the at least one finger extensor muscle;
wherein steps e-j are performed between steps b. and c. and accordingly repeated at least 5 times.

8. The method of claim 1 further comprising:
e. relaxation of the at least one finger extensor muscle;
f. stimulation of at least one thumb flexion muscle;
g. relaxation of the at least one thumb flexion muscle; and
h. stimulation of the at least one finger extensor muscle;
wherein steps e-h are performed between steps b. and c. and accordingly repeated at least 5 times.

9. The method of claim 1 further comprising:
e. relaxation of the at least one finger extensor muscle; and
f. stimulation of the at least one finger extensor muscle;
wherein steps e. and f. are performed between steps b. and c. and accordingly repeated at least 5 times.

10. The method of claim 1, wherein the electrical pulse has an amplitude capable of producing desired muscle contractions for carrying out movement and tasks in physiologically accurate manner.

11. The method of claim 4, wherein the stimulation of at least one dorsal interrosseous muscle of the same hand includes
a. placing at least one cathode electrode on a posterior part of the hand between two metacarpals, on said hand;
b. placing an anode on the proximal and anterior part of a wrist on said hand; and
c. passing an electric current through the at least one electrode to the anode.

* * * * *

UNITED STATES PATENT AND TRADEMARK OFFICE
CERTIFICATE OF CORRECTION

| | |
|---|---|
| PATENT NO. | : 9,616,224 B2 |
| APPLICATION NO. | : 14/411200 |
| DATED | : April 11, 2017 |
| INVENTOR(S) | : Abdulkadir Bulsen, Naaz Ankur Desai and Mulos Popovic |

It is certified that error appears in the above-identified patent and that said Letters Patent is hereby corrected as shown below:

On the Title Page

Item (72), Inventors:, that portion of the section reading:
-Abudulkadir Bulsen, Scarborough (CA)-
Should be changed to read:
-Abdulkadir Bulsen, Scarborough (CA)-

Signed and Sealed this
First Day of August, 2017

Joseph Matal
*Performing the Functions and Duties of the*
*Under Secretary of Commerce for Intellectual Property and*
*Director of the United States Patent and Trademark Office*